(12) United States Patent
Bush et al.

(10) Patent No.: US 6,638,711 B1
(45) Date of Patent: Oct. 28, 2003

(54) METHODS FOR IDENTIFYING AN AGENT THAT INHIBITS OXYGEN-DEPENDENT HYDROGEN PEROXIDE FORMATION ACTIVITY BUT DOES NOT INHIBIT SUPEROXIDE-DEPENDENT HYDROGEN PEROXIDE FORMATION

(75) Inventors: Ashley I. Bush, Somerville, MA (US); Xudong Huang, Andover, MA (US); Craig S. Atwood, Brecksville, OH (US); Rudolph E. Tanzi, Hull, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/560,883

(22) Filed: Apr. 28, 2000

Related U.S. Application Data

(63) Continuation-in-part of application No. 09/380,704, filed as application No. PCT/US98/04683 on Mar. 11, 1998.
(60) Provisional application No. 60/131,579, filed on Apr. 29, 1999.

(51) Int. Cl.$^7$ .......................... C12Q 1/00; G01N 33/48; G01N 33/20; C07K 2/00
(52) U.S. Cl. ................... 435/4; 436/80; 436/84; 436/127; 530/350
(58) Field of Search .................. 435/7.1, 7.7, 7.8, 435/7.9, 27, 4, 7.92; 436/501, 504, 904, 63, 80, 84; 514/2; 530/300, 350

(56) References Cited

U.S. PATENT DOCUMENTS

| | | | |
|---|---|---|---|
| 4,419,365 A | 12/1983 | McLachlan | 424/320 |
| 5,110,493 A | 5/1992 | Cherng-Chyi et al. | 514/413 |
| 5,242,932 A | 9/1993 | Gandy et al. | 514/313 |
| 5,310,936 A | 5/1994 | Regtop et al. | 548/501 |
| 5,357,636 A | 10/1994 | Dresdner, Jr. et al. | 2/161.7 |
| 5,373,021 A | 12/1994 | Marangos | 514/483 |
| 5,466,680 A | 11/1995 | Rudy | 514/57 |
| 5,523,295 A | 6/1996 | Fasman | 514/63 |
| 5,688,516 A | 11/1997 | Raad et al. | 424/409 |
| 5,688,651 A | 11/1997 | Solomon | 435/7.1 |
| 5,705,401 A | 1/1998 | Masters et al. | 436/518 |
| 5,707,821 A | 1/1998 | Rydel et al. | 435/18 |
| 5,721,106 A | 2/1998 | Maggio et al. | 435/7.8 |
| 5,927,283 A | 7/1999 | Abraham et al. | 128/898 |
| 5,980,914 A | 11/1999 | Gerolymatos | 424/400 |
| 5,994,323 A | 11/1999 | Gerolymatos | 514/52 |
| 6,001,852 A | 12/1999 | Gerolymatos | 514/311 |

FOREIGN PATENT DOCUMENTS

| | | |
|---|---|---|
| DE | 40 04 978 A1 | 8/1991 |
| WO | WO 92/18111 | 10/1992 |
| WO | WO 93/10459 | 5/1993 |
| WO | WO 93/24451 | 12/1993 |
| WO | WO 94/04167 | 3/1994 |
| WO | WO 94/27594 | 12/1994 |
| WO | WO 95/31199 | 11/1995 |
| WO | WO 96/07096 | 3/1996 |
| WO | WO 96/12544 | 5/1996 |
| WO | WO 96/28471 | 9/1996 |
| WO | WO 96/39144 | 12/1996 |
| WO | WO 97/01559 | 1/1997 |
| WO | WO 97/04794 | 2/1997 |
| WO | WO 97/09976 | 3/1997 |
| WO | WO 97/36885 | 10/1997 |
| WO | WO 98/06403 | 2/1998 |
| WO | WO 98/40071 | 9/1998 |
| WO | WO 99/09981 | 3/1999 |
| WO | WO 99/18432 | 4/1999 |

OTHER PUBLICATIONS

Aisen et al. 2002. Neurology, vol. 58: 1050–1054. Randomized pilot study of nimesulide treatment in Alzheimer's disease.*

Rosler et al. 1998. J Neural transm Suppl. vol. 54: 211–219. Free radicals in Alzheimer's dementia: currently available therapeutic strategies.*

Gutierrez–Correa, J. and A.O.M. Stoppani, Free Rad. Res. 22(3): 239–250 (Mar. 1995) (publisher: Harwood Academic Publishers GmbH).

Lodemann, E., Naturwissenschaften 66(9): 462–466 (Sep. 1979) (publisher: Springer–Verlag).

Sue, Y.–J. et al., Annals of Emergency Medicine 24(4): 709–712 (Oct. 1994) (publisher: American College of Emergency Physicians).

Atwood, C.S. et al., "Role of Free Radicals and Metal Ions in the Pathogenesis of Alzheimer's Disease," in *Metal Ions in Biological Systems*, Sigel, A. and Sigel H., eds., vol. 36, Ch. 10, Marcel Dekker, Inc., New York, pp. 309–364 (1999).

McKeon–O'Mally, C., et al., "Potential Therapeutic Targets for Alzheimer's Disease," *Emerging Therapeutic Targets* 2:157–179, Ashley Publications Ltd. (Feb. 1998).

Assaf, S.Y and Chung, S.–H., "Release of endogenous $Zn^{2+}$ from brain tissue during activity," *Nature* 308:734–736 (Apr. 1984).

Atwood, C.S. et al., "Copper–Mediated Aggregation And Polymerization of Aβ," *Soc. Neurosci. Abstr.* 23:1883 (Oct. 1997).

Atwood, C.S., et al., "Dramatic aggregation of Alzheimer abeta by Cu(II) is induced by conditions representing physiological acidosis," *J. Biol. Chem.* 273:12817–12826 (1998).

Bacon, P.A. et al., "Rheumatoid Disease, Amyloidosis and its Treatment with Penicillamine," *Eur. J. Rheum. Inflamm.* 2:70–74 (1979).

(List continued on next page.)

*Primary Examiner*—Elizabeth Kemmerer
*Assistant Examiner*—Bridget E. Bunner
(74) *Attorney, Agent, or Firm*—Sterne, Kessler, Goldstein & Fox, P.L.L.C.

(57) ABSTRACT

The invention relates to methods for identifying candidate pharmacological agents to be used in the treatment and/or prevention of Alzheimer's disease and/or related pathological conditions.

9 Claims, 22 Drawing Sheets

OTHER PUBLICATIONS

Barrow, C.J., and Zagorski, M.G., "Solution Structures of β Peptide and Its Constituent Fragments: Relation to Amyloid Deposition," *Science* 253:179–182 (Jul. 1991).

Barrow, C.J., et al., "Solution Conformations and Aggregational Properties of Synthetic Amyloid β–Peptides of Alzheimer's Disease," *J. Mol. Biol.* 225:1075–1093 (Jun. 1992).

Basun, H., et al., "Metals and trace elements in plasma and cerebrospinal fluid in normal ageing and Alzheimer's disease," *J. Neural. Transm. [P–D Sect.]* 3:231–258 (1991).

Beal, M. F., "Energy, Oxidation Damage, and Alzheimer's Disease: Clues to the Underlying Puzzle," *Neurobiol. Aging* 15:S171–S174 (1994).

Behl, C., e al., "Hydrogen Peroxide Mediates Amyloid β Protein Toxicity," *Cell* 77:817–827 (Jun. 1994).

Biaglow, J.E. and Kachur, A.V., "The Generation of Hydroxyl Radicals in the Reaction of Molecular Oxygen with Polyphosphate Complexes of Ferrous Ion," *Radiation Res.* 148:181–187 (Aug. 1997).

Boado, R.J. et al., "Drug Delivery of Antisense Molecules to the Brain for Treatment of Alzheimer's Disease and Cerebral AIDS," *J. Pharm. Sci.* 87(11):1308–1315 (Nov. 1998).

Borman, S., "Diverse Strategies Emerge For Diagnosing Alzheimer's Disease," *Chem. Eng. News* 272:33–34 (Jun. 1996).

Brown, D.R., et al. "Normal prion protein has an activity like that of superoxide dismutase," *Biochem. J.* 344:1–5 (Nov. 1999).

Bruce, A.J. et al., "β–Amyloid toxicity ini organotypic hippocampal cultures: Protection by EUK–8, a synthetic catalytic free radical scavenger," *Proc. Natl. Acad. Sci. USA* 93:2312–2316 (Mar. 1996).

Bruijn, L.I., et al., "ALS–Linked SOD1 Mutant G85R Mediates Damage to Astrocytes and Promotes Rapidly Progressive Disease with SOD1–Containing Inclusions," *Neuron.* 18:327–338 (Feb. 1997).

Burdick, D., et al., "Assembly and Aggregation Properties of Synthetic Alzheimer's A4/β Amyloid Peptide Analogs," *J. Biol. Chem.* 267:546–554 (Jan. 1992).

Burns, J.A., et al., "Selective Reduction of Disulfides by Tris(2–carboxyethyl)phosphine," *J. Org. Chem.* 56:2648–2650 (Apr. 1991).

Busciglio, J., and Yankner, B.A., "Apoptosis and increased generation of reactive oxygen species in Down's Syndrome neurons in vitro," *Nature* 378:776–779 (Dec. 1995).

Bush, A.I., et al., "A Novel Zinc(II) Binding Site Modulates the Function of the βA4 Amyloid Protein Precursor of Alzheimer's Disease," *J. Biol. Chem.* 268:16109–16112 (Aug. 1993).

Bush, A.I., et al., "Alzheimer Aβ functions as a superoxide antioxidant in vitro and in vivo," *Soc. Neurosci. Abstr.* 25:14 (Oct. 1999).

Bush, A.I., et al., "Modulation of Aβ Adhesiveness and Secretase Site Cleavage by Zinc," *J. Biol. Chem.* 269:12152–12158 (Apr. 1994).

Bush, A.I., et al., "The Amyloid β–Protein Precursor and Its Mammalian Homologues," *J. Biol. Chem.* 269:26618–26621 (Oct. 1994).

Bush, A.I., et al., "Rapid Induction of Alzheimer Aβ Amyloid Formation by Zinc," *Science* 265:1464–1467 (Sep. 1994).

Bush, A.I., et al., Response to "Zinc and Alzheimer's Disease," *Science* 268:1920–1923 (Jun. 1995).

Butterfield, D.A., et al., "β–Amyloid Peptide Free Radical Fragments Initiate Synaptosomal Lipoperoxidation in a Sequence–Specific Fashion: Implications to Alzheimer's Disease," *Biochem. Biophys. Res. Commun.* 200:710–715 (Apr. 1994).

Butterfield, D.A., et al., "Aβ(25–35) Peptide Displays $H_2O_2$–Like Reactivity Towards Aqueous $Fe^{2+}$, Nitroxide Spin Probes, and Synaptosomal Membrane Proteins," *Life. Sci.* 58:217–228 (1996).

Ceballos–Picot, I., et al., "Peripheral Antioxidant Enzyme Activities And Selenium In Elderly Subjects And In Dementia Of Alzheimer's Type–Place Of The Extracellular Glutathione Peroxidase," *Free Radic. Biol. Med.* 20:579–587 (1996).

Chan, C.-W., et al., "Anti–apoptotic action of Alzheimer Aβ," *Alzheimer's Reports* 2:113–119 (Mar. 1999).

Cherny, R.A. et al., "The Aggregation of Aβ in Human Brain is Mediated by Zinc," *Soc. for Neurosci. Abstracts* 23:534 (Oct. 1997).

Cherny, R.A., et al., "Aqueous Dissolution of Alzheimer's Disease Aβ Amyloid Deposits by Biometal Depletion," *J. Biol. Chem.* 274:23223–23228 (1999).

Chong, Y.-H., and Suh, Y.-H., "Aggregation of amyloid precursor proteins by aluminum in vitro," *Brain Research* 670:137–141 (Jan. 1995).

Cohen, A.S., "Amyloidosis," *Arthritis and Allied Conditions—A Textbook of Rheumatology*, D.J. McCarty, ed., Lea and Febiger, Philadelphia, pp. 1273–1293 (1989).

Colaco, C.A.L.S., et al., "The role of the Maillard reaction in other pathologies: Alzheimer's disease," *Nephrol. Dial. Transplant.* 11(Suppl. 5):7–12 (1996).

Connor, J.R. et al., "A Histochemical Study of Iron, Transferrin, and Ferritin in Alzheimer's Diseased Brains," *J. Neurosci. Res.* 31:75–83 (Jan. 1992).

Connor, J.R. et al., "Ceruloplasmin levels in the human superior temporal gyrus in aging and Alzheimer's disease," *Neurosci. Lett.* 159:88–90 (Sep. 1993).

Coyle, J.T., and Puttfarcken, P., "Oxidative Stress, Glutamate, and Neurodegenerative Disorders," *Science* 262:689–695 (Oct. 1993).

Crapper, McLachlan, D.R. et al., "Intramuscular desferrioxamine in patients with Alzheimer's disease," *Lancet* 337:1304–1308 (Jun. 1991).

Cuajungco, M.P. and Lees, G.J., "Zinc and Alzheimer's disease: is there a direct link?" *Brain Res. Rev.* 23:219–236 (Apr. 1997).

Dedman, D.J. et al., "Iron and aluminum in relation to brain ferritin in normal individuals and Alzheimer's –disease and chronic renal–dialysis patients," *Biochem J.* 287:509–514 (1992).

Hensley, K et al., "A model for beta–amyloid aggregation and neurotoxicity based on free radical generation by the peptide: Relevance to Alzheimer disease," *Proc. Natl. Acad. Sci. U.S.A.* 91:3270–3274 (Apr. 1994).

Hensley, K et al., "Brain Regional Correspondence Between Alzheimer's Disease Histopathology and Biomarkers of Protein Oxidation," *J. of Neurochem.* 65:2146–2156 (Nov. 1995).

Hensley, K., et al., "Reactive Oxygen Species as Causal Agents in the Neurotoxicity of the Alzheimer's Disease–Associated Amyloid Beta Peptide," *Ann N. Y. Acad. Sci.* 786:120–134 (1996).

Hesse, L., et al., "The βA4 amyloid precursor protein binding to copper," *FEBS Lett. 349*:109–116 (Jul. 1994).

Hilbich, C., et al. "Aggregation and Secondary Structure of Synthetic Amyloid βA4 Peptides of Alzheimer's Disease," *J. Mol. Biol. 218*:149–163 (Mar. 1991).

Hilbich, C. et al., "Substitutions of Hydrophobic Amino Acids Reduce the Amyloidogenicity of Alzheimer's Disease βA4 Peptides," *J. Mol. Biol. 228*:460–473 (Nov. 1992).

Hsu, J.M., et al., "Zinc deficiency and incorporation of 14C–labeled methionine into tissue proteins in rats," *J. Nutr. 99*:425–432 (1969).

Huang, X. et al., "Zinc–induced Alzheimer's Aβ1–40 Aggregation Is Mediated by Conformational Factors," *J. Biol. Chem. 272*:26464–26470 (Oct. 1997).

Huang, X., et al., "The Aβ Peptide of Alzheimer's Disease Directly Produces Hydrogen Peroxide through Metal Ion Reduction," *Biochemistry 38*:7609–7616 (Jun. 1999).

Ida, N., et al., "Analysis of Heterogeneous βA4 Peptides in Human Cerebrospinal Fluid and Blood by a Newly Developed Sensitive Western Blot Assay," *J. Biol. Chem. 271*:22908–22914 (Sep. 1996).

Jarrett, J.T., et al., "The Carboxy Terminus of the β Amyloid Protein Is Critical for the Seeding of Amyloid Formation: Implications for the Pathogenesis of Alzheimer's Disease," *Biochem. 32*:4693–4697 (May 1993).

Jarrett, J.T., and Lansbury, Jr., P.T., "Amyloid Fibril Formation Requires a Chemically Discriminating Nucleation Event: Studies of an Amyloidogenic Sequence from the Bacterial Protein OsmB," *Biochem. 31*:12345–12352 (Dec. 1992).

Johnston, E.M. et al., "Conservation of the sequence of the Alzheimer's disease amyloid peptide in dog, polar bear, and five other mammals by cross–species polymerase chain reaction analysis," *Mol. Brain Res. 10*:299–305 (Jul. 1991).

Joshi, J.G., "Iron and Aluminum Homeostasis in Neural Disorders," *Environ. Health Persp. 102*:207–213 (1994).

Kang, J. et al., "The precursor of Alzheimer's disease amyloid A4 protein resembles a cell–surface receptor," *Nature 325*:733–736 (Feb. 1987).

Kawahara, M. et al., "Alzheimer's Disease Amyloid β–Protein Forms $Zn^{2+}$ –Sensitive Cation–Selective Channels Across Excised Membrane Patches from Hypothalamic Neurons," *Biophys. J. 73*:67–75 (Jul. 1997).

Kennard, M.L. et al., "Serum levels of the iron binding protein p97 are elevated in Alzheimer's disease," *Nat. Med. 2*:1230–1235 (Nov. 1996).

Kidani, Y. et al., "Mass spectrometry of 5–chloro–7–iodo–8–quinolinol metal chelates," *Jpn. Analyst 23*:1375–1378 (1974).

Kirschner, D.A. et al., "Synthetic peptide homologous to β protein from Alzheimer disease forms amyloid–like fibrils in vitro," *Proc. Natl. Acad. Sci. USA 84*:6953–6957 (Oct. 1987).

Kirschenbaum, K., and Daggett, V., "pH–Dependent Conformations of the Amyloid β(1–28) Peptide Fragment Explored Using Molecular Dynamics," *Biochem. 34*:7629–7639 (Jun. 1995).

Kisilevsky, R., "Amyloidosis: A Familiar Problem in the Light of Current Pathogenetic Developments," *Lab. Invest. 49*:381–390 (Oct. 1983).

Kisilevsky, R., "Inflammation–Associated Amyloidogenesis," *Mol. Neurobiol. 8*:65–66 (Feb. 1994).

Koh, J.Y., and Choi, D.W., "Quantitative determination of glutamate mediated cortical neuronal injury in cell culture by lactate dehydrogenase efflux assay," *J. Neurosci. Meth. 20*:83–90 (May 1987).

Kotaki, H., et al., "Intestinal Absorption and Metabolism of Clioquinol in the Rat," *J. Pharm. Dyn. 6*:881–887 (Nov. 1983).

Kuo, Y.–M., et al., "High Levels of Circulating Aβ42 Are Sequestered by Plasma Proteins in Alzheimer's Disease," *Biochem. Biophys. Res. Commun. 257*:787–791 (Apr. 1999).

Kuo, Y.–M., et al., "Water–Soluble Aβ (N–40, N–42) Oligomers in Normal and Alzheimer Disease Brains," *J. Biol. Chem. 271*:4077–4081 (Feb. 1996).

Landers, J.W., and Zak, B., "Determination of Serum Copper and Iron in a Single Small Sample," *Am. J. Clin. Pathol. 29*:590–592 (Jun. 1958).

Lindeman, R.D., et al., "Myocardial zinc metabolism in experimental myocardial infarction," *J. Lab. Clin. Med. 81*:194–204 (Feb. 1973).

Linert, W. et al., "Dopamine, 6–hydroxydopamine, iron, and dioxygen—their mutual interaction and possible implication in the development of Parkinson's disease," *Biochim. Biophys. Acta1316*:160–168 (Aug. 1996).

Lockhart B.P. et al., "Inhibitors of free radical formation fail to attenuate direct beta–amyloid$_{25-35}$ peptide–mediated neurotoxicity in rat hippocampal cultures," *J. Neurosci. Res. 39*:494–505 (Nov. 1994).

Lohr, J.B., "Oxygen Radicals and Neuropsychiatric Illness," *Arch. Gen. Psychiatry 48*:1097–1106 (Dec. 1991).

Lovell, M.A., et al., "Copper, iron and zinc in Alzheimer's disease senile plaques," *J. Neurol. Sci. 158*:47–52 (Jun. 1998).

Maggio, J.E., et al., "Zinc and Alzheimer's Disease," *Science 268*:1920–1921 (Jun. 1995).

Mantyh, P.W., et al. "Aluminum, Iron, and Zinc Ions Promote Aggregation of Physiological Concentrations of β–Amyloid Peptide," *J. Neurochem. 61*:1171–1174 (Sep. 1993).

Markesbery, W.R. and Ehmann, W.D., "Brain Trace Elements in Alzheimer Disease," Chapter 22 in *Alzheimer Disease*, Terry, R.D. et al., eds., Raven Press, Ltd., New York (1994).

Markesbery, W.R., "Oxidative Stress Hypothesis in Alzheimer's Disease," *Free Rad. Biol. Med. 23*:134–147 (1997).

Martins, R.N., et al., "Increased Cerebral Glucose–6–Phosphate Dehydrogenase Activity in Alzheimer's Diseases May Reflect Oxidative Stress," *J. Neurochem. 46*:1042–1045 (Apr. 1986).

Masters, C.L., et al., "Amyloid plaque core protein in Alzheimer disease and Down syndrome," *Proc. Natl. Acad. Sci. USA 82*:4245–4249 (Jun. 1985).

Masters, C. L. et al., "Neuronal origin of a cerebral amyloid: neurofibrillary tangles of Alzheimer's disease contain the same protein as the amyloid of plaque cores and blood vessels," *EMBO J. 4*:2757–2763 (Nov. 1985).

Maury, C.P.J., "Biology of Disease: Molecular Pathogenesis of β–Amyloidosis in Alzheimer's Disease and Other Cerebral Amyloidoses," *Lab. Invest. 72*:4–16 (Jan. 1995).

McGeer, P.L., and McGeer, E.G., "The inflammatory response system of brain: implications for therapy of Alzheimer and other neurodegenerative diseases," *Brain Res. Rev.* 21:195–218 (Sep. 1995).

Mecocci, P., M.D. et al., "Oxidative Damage to Mitochondrial DNA Shows Marked Age–dependent Increases in Human Brain," *Ann. Neurol.* 34:609–616 (Oct. 1993).

Menkin, V., "Studies on Inflammation. X. The Cytological Picture of an Inflammatory Exudate in Relation to its Hydrogen Ion Concentration," *Am. J. Pathol.* 10:193–210 (Mar. 1934).

Michikawa, M., et al., "Oxygen Radical–Induced Neurotoxicity in Spinal Cord Neuron Cultures," *J. Neurosci. Res.* 37:62–70 (Jan. 1994).

Milanino, R., et al., "Copper and the Inflammatory Process," *Advances in Inflammation Research* 1:281–291 (1979).

Moir, R.D. et al., "Relative Increase in Alzheimer's Disease of Soluble Forms of Cerebral Aβ Amyloid Protein Precursor Containing the Kunitz Protease Inhibitory Domain," *J. Biol. Chem.* 273:5013–5019 (Feb. 1998).

Mok, S.S., et al., "A Novel Metalloprotease in Rat Brain Cleaves the Amyloid Precursor Protein of Alzheimer's Disease Generating Amyloidogenic Fragments," *Biochemistry* 36:156–163 (Jan. 1997).

Kang, J., et al., "The precursor of Alzheimer's disease amyloid A4 protein resembles a cell–surface receptor," *Nature* 325:733–736 (Feb. 1987).

Multhaup, G., et al., "Interaction between the zinc(II) and the heparin binding site of the Alzheimer's disease βA4 amyloid precursor protein (APP)," *FEBS Lett.* 355:151–154 (Nov. 1994).

Multhaup, G., et al., "The Amyloid Precursor Protein of Alzheimer's Disease in the Reduction of Copper(II) to Copper(I)," *Science* 271:1406–1409 (Mar. 1996).

Münch, G., et al., "Advanced glycation endproducts in ageing and Alzheimer's disease," *Brain Res. Rev.* 23:134–143 (Feb. 1997).

Nakada, T., and Kwee, I.L., "Guanidinoethane sulfate: brain pH alkaline shifter," *NeuroReport* 4:1035–1038 (Aug. 1993).

Nunomura, A., et al., "RNA Oxidation Is a Prominent Feature of Vulnerable Neurons in Alzheimer's Disease," *J. Neurosci.* 19:1959–1964 (Mar. 1999).

Okada, H. et al., "Effects of Metal–Containing Drugs Taken Simultaneously with Clioquinol Upon Clinical Features of SMON," *J. Toxicol. Sci.* 9:327–341 (1984).

Owen, C.A., Jr., "Uptake of $^{67}$Cu by Ceruloplasmin In Vitro (38878)," *Proc. Soc. Exp. Biol. Med.* 149:681–682 (Jul. 1975).

Padmanabhan, G., et al., "Clioquinol," in:*Analytical Profiles of Drug Substances*, vol. 18, Florey, K., eds., Academic Press, Inc.:San Diego, CA, pp. 57–90 (1989).

Pepys, M.B. and Baltz, M.L., "Acute Phase Proteins with Special Reference to C–Reactive Protein and Related Proteins (Pentaxins) and Serum Amyloid A Protein," in *Advances in Immunology*, vol. 34, pp. 141–212 (1983).

Pérez, A.A. et al., "Alzheimer Amyloids Aβ1–40 and Aβ1–42 are Differentially Degraded by Insulin Degrading Enzyme (IDE) From Human Brain," *Soc. Neurosci. Abstracts* 23:821 (Oct. 1997).

Peters, G., and Rodgers, M.A.J., "Single–Electron Transfer from NADH Analogues to Singlet Oxygen," *Biochim. Biophys. Acta* 637:43–52 (Aug. 1981).

Pierce, J.E.S., et al., "Immunohistochemical Characterization of Alterations in the Distribution of Amyloid Precursor Proteins and β–Amyloid Peptide after Experimental Brain Injury in the Rat," *J. Neurosci.* 16:1083–1090 (Feb. 1996).

Potempa, L.A., et al., "Effect of Divalent Metal Ions and pH upon the Binding Reactivity of Human Serum Amyloid P Component, a C–reactive Protein Homologue, for Zymosin," *J. Biol. Chem.*260:12142–12147 (Oct. 1985).

Raby, C.A., et al., "Traumatic Brain Injury Increases β–Amyloid Peptides 1–42 in Cerebrospinal Fluid," *J. Neurochem.* 71:2505–2509 (Dec. 1998).

Richardson, J.S., et al., "On the Possible Role of Iron–Induced Free Radical Peroxidation in Neural Degeneration in Alzheimer's Disease," *Ann. N.Y. Acad. Sci.* 648:326–327 (1992).

Roberts, G.W., et al., "βA4 amyloid protein deposition in brain after head trauma," *Lancet* 338:1422–1423 (Dec. 1991).

Robinson, S.R. et al., "Most amyloid plaques contain ferritin–rich cells," *Alzheimer's Res.* 1:191–196 (1995).

Rogers, J., et al., "Clinical trial of indomethacin in Alzheimer's disease," *Neurology* 43:1609–1611 (Aug. 1993).

Roher, A.E., et al., "Morphology and Toxicity of Aβ–(1–42) Dimer Derived from Neuritic and Vascular Amyloid Deposits of ALzheimer's Disease," *J. Biol. Chem.* 271:20631–20635 (Aug. 1996).

Rosen, D., et al., "Mutations in Cu/Zn superoxide dismutase gene are associated with familial amyotrophic lateral sclerosis," *Nature* 362:59–62 (Mar. 1993).

Rumble, B. et al., "Amyloid A4 Protein and Its Precursor in Down's Syndrome and Alzheimer's Disease," *New Eng. J. of Med.* 320:1446–1452 (Jun. 1989).

Sadowski, M. et al., "Astrocyte and microglia reaction in Alzheimer's disease in the hippocampal formation—a quantitative analysis," *Alzheimer's Res.* 1:71–76 (1995).

Sano, M., et al., "A Controlled Trial of Selegiline, Alpha–Tocopherol, or Both as Treatment for Alzheimer's Disease," *N.Engl. J. Med.* 336:1216–1222 (Apr. 1997).

Sayre, L.M., "Alzheimer's Precursor Protein and the Use of Bathocuproine for Determining Reduction of Copper(II)," *Science* 274:1933–1934 (Dec. 1996).

Schnabel, J., "New Alzheimer's Therapy Suggested," *Science* 260:1719–1720 (Jun. 1993).

Schrader–Fischer, G., and Pagnetto, P.A., "Effect of alkalizing agents on the process of the β–amyloid precursor protein," *Brain Research* 716:91–100 (Apr. 1996).

Schubert, D., and Chevion, M., "The Role of Iron in Beta Amyloid Toxicity," *Biochem. Biophsy. Res. Commun.* 216:702–707 (Nov. 1995).

Selkoe, D.J., "Cell Biology of the Amyloid β–Protein Precursor and the Mechanism of Alzheimer's Disease," *Ann. Rev. Cell Biol.* 10:373–403 (1994).

Seubert, P. et al., "Isolation and quantification of soluble Alzheimer's β–peptide from biological fluids," *Nature* 359:325–327 (Sep. 1992).

Shiraki, H., "Neuropathological aspects of the etiopathogenesis of subacute myelo–optico–neuropathy (SMON)," in *Handbook of Clinical Neurology. Intoxications of the Nervous System Part II*, Vinken, P. J. and Bruyn, G. W., eds., North–Holland Publishing Company, Amsterdam, Holland, pp. 141–198 (1979).

Shivers, B.D. et al., "Alzheimer's disease amyloidogenic glycoprotein: expression pattern in rat brain suggests a role in cell contact," *EMBO J.* 7:1365–1370 (1988).

Shoji, M. et al., "Production of the Alzheimer Amyloid β Protein by Normal Proteolytic Processing," *Science* 258:126–129 (Oct. 1992).

Sisodia, S.S. et al., "Cellular and molecular biology of Alzheimer's disease and animal models," *Neurodegenerative Diseases* 5:59–68 (Feb. 1995).

Skinner, M. et al., "Observations on the amyloid–degrading activity of serum and its relationship to human neutrophil elastase," *Trans. Assoc. Am. Phys.* 96:437–443 (1983).

Smalheiser, N.R., and Swanson, D.R., "Indomethacin and Alzheimer's disease," *Neurology* 46:583 (Feb. 1996).

Smith, C. et al., "The molecular pathology of Alzheimer's disease: are we any closer to understanding the neurodegenerative process?," *Neuropathol. Appl. Neurobiol.* 20:322–338 (Aug. 1994).

Smith, M.A., et al., "Radical Ageing in Alzheimer's disease," *Trends Neurosci.* 18:172–176 (Apr. 1995).

Smith, M. A., et al., "Oxidative damage in Alzheimer's," *Nature* 382:120–121 (Jul. 1996).

Smith M.A., et al., "Iron accumulation in Alzheimer disease is a source of redox–generated free radicals," *Proc. Natl. Acad. Sci. U.S.A.* 94:9866–9868 (Sep. 1997).

Sobue, I., "Clinical aspects of subacute myelo–optico–neuropathy (SMON)," in *Handbook of Clinical Neurology. Intoxications of the Nervous System Part II*, Vinken, P. J. and Bruyn, G. W., eds., North–Holland Publishing Company, Amsterdam, Holland, pp. 115–139 (1979).

Soto, C. et al., "β–sheet breaker peptides inhibit fibrillogenesis in a rat brain model of amyloidosis: Implications for Alzheimer's therapy," *Nature Med.* 4:822–826 (Jul. 1998).

Soto, C., et al., "Structural Determinants of the Alzheimer's Amyloid β–Peptide," *J. Neurochem.* 63:1191–1198 (Oct. 1994).

Soto, C. et al., "Inhibition of Alzheimer's Amyloidosis by Peptides That Prevent β–Sheet Conformation," *Biochem. Biophys. Res. Comm.* 226:672–680 (Sep. 1996).

Stankovic, A., and Mitrovic, D.R., "Aluminum Salts Stimulate Luminol–Enhanced Chemiluminescence Production by Human Neutrophils," *Free Rad. Res. Comms.* 14:47–55 (1991).

Suzuki, N., et al., "An Increased Percentage of Long Amyloid β–Protein Secreted by Familial Amyloid β–Protein Precursor ($\beta APP_{717}$) Mutants," *Science* 264:1336–1340 (May 1994).

Tanzi, R.E. et al., "The Wilson disease gene is a copper transporting ATPase with homology to the Menkes disease gene," *Nat. Gen.* 5:344–350 (Dec. 1993).

Tanzi, R.E. et al., "Amyloid β Protein Gene: cDNA, mRNA Distribution, and Genetic Linkage Near the Alzheimer Locus," *Science* 235:880–884 (Feb. 1987).

Tamura, Z., "Clinical Chemistry of Clioquinol," *Jpn. J. Med. Sci. Biol.* 28:69–77 (1975).

Tateishi, J. et al., "Strain–differences in dogs for neurotoxicity of clioquinol," *Lancet* 1:1289–1290 (Jun. 1972).

Tateishi, J. et al., "Myeloneuropathy in dogs induced by iodoxyquinoline," *Neurology* 22:702–709 (Jul. 1972).

Tateishi, J. et al., "Autoradiographic Distribution of $^{131}$I–Clioquinol in Canine and Feline," *Folia Psychiatrica et Neurologica Japonica* 26:159–164 (1972).

Tateishi, J. et al., "Experimental Myelo–optic Neuropathy Induced by Clioquinol," *Acta neuropath. (Berl.)*, 24:304–320 (1973).

Tateishi, J. et al., "Neurotoxicity of Clioquinol. Part III: Autoradiographic Distribution of Radioactive Clioquinol in Several Species of Animals," *Psychiat. Neurol. Jap.* 75:187–196 (1973).

Tateishi, J. et al., "Neurotxicity of Clioquinol in Laboratory Animals," *Lancet* 2:1095 (Nov. 1972).

Teller, J.K., et al., "Presence of soluble amyloid β–peptide precedes amyloid plaque formation in Down's Syndrome," *Nature Med.* 2:93–95 (Jan. 1996).

Terhune, M.W., and Sandstead, H.H., "Decreased RNA Polymerase Activity in Mammalian Zinc Deficiency," *Science* 177:68–69 (Jul. 1972).

Terry, R.D., et al., "Physical Basis of Cognitive Alterations in Alzheimer's Disease: Synapse Loss Is the Major Correlate of Cognitive Impairment," *Ann. Neurol.* 30:572–580 (Oct. 1991).

Thomas, T., et al., "β–Amyloid–mediated vasoactivity and vascular endothelial damage," *Nature* 380:168–171 (Mar. 1996).

Tomiyama, T., et al., "Rifampicin Prevents the Aggregation and Neurotoxicity of Amyloid β Protein In Vitro," *Biochem. Biophys. Res. Comm.* 204:76–83 (Oct. 1994).

Tomiyama, T., et al., "Inhibition of Amyloid β Protein Aggregation and Neurotoxicity by Rifampicin," *J. Biol. Chem.* 271:6839–6844 (Mar. 1996).

Thompson, C.M. et al., "Regional Brain Trace–Element Studies in Alzheimer's Disease," *NeuroToxicol.* 9:1–7 (1988).

Tomski, S.J., and Murphy, R.M., "Kinetics of Aggregation of Synthetic β–Amyloid Peptide," *Arch. Biochem. Biophys.* 294:630–638 (May 1992).

Treuhaft, P.S., and McCarty, D.J., "Synovial Fluid pH, lactate, Oxygen and Carbon Dioxide Partial Pressure in Various Joint Diseases," *Arth. Rheum.* 4:475–484 (Jul.–Aug. 1971).

Uchida, K. and Kawakishi, S., "Identification of oxidized Histidine Generated at the Active Site of Cu,Zn–Superoxide D Dismutase Exposed to $H_2O_2$. Selective Generation of 2–Oxo–Histidine At The Histidine 118," *J. Biol. Chem.* 269:2405–2410 (Jan. 1994).

Van Nostrand, W.E, "Zinc (II) Selectively Enhances the Inhibition of Coagulation Factor XIa by Protease Nexin–2/ Amyloid β–Protein Precursor," *Thrombosis Res.* 78:43–53 (Apr. 1995).

Warren, P.J. et al., "The Distribution of Copper in Human Brain," *Brain.* 83:709–717 (1960).

Weismann, K., and Knudsen, L., "Effects of Penicilliamine and Hydroxyquinole on Absorption of Orally Ingested $^{65}$Zinc in the Rat," *J. Invest. Dermatol.* 71:242–244 (Oct. 1978).

Wolozin, B., et al., "Participation of presenilin 2 in Apoptosis: Enhanced Basal Activity Conferred by an Alzheimer Mutation," *Science* 274:1710–1713 (Dec. 1996).

Wood, S.J., et al., "Physical, Morphological and Functional Differences between pH 5.8 and 7.4 Aggregates of the Alzheimer's Amyloid Peptide Aβ," *J. Mol. Biol.* 256:870–877 (Mar. 1996).

Yankner, B.A., et al., "Neurotrophic and Neurotoxic Effects of Amyloid β Protein: Reversal by Tachykinin Neuropeptides," *Science* 250:279–282 (Oct. 1990).

Yates, C.M., et al., "Enzyme Activities in Relation to pH and Lactate in Postmortem Brain in Alzheimer–Type and Other Dementias," *J. Neurochem.* 55:1624–1630 (Nov. 1990).

Yim, M.B., et al., "A gain–of–function of an amyotrophic lateral sclerosis–associated Cu,Zn–superoxide dismutase mutant: An enhancement of free radical formation due to a decrease in $K_m$ for hydrogen peroxide," *Proc. Natl. Acad. Sci. USA* 93:5709–5714 (Jun. 1996).

Zagorski, M.G., and Barrow, C.J., "NMR Studies of Amyloid β–Peptides: Proton Assignments, Secondary Structure, and Mechanism of an α–Helix→β–Sheet Conversion for a Homologous, 28–Residue, N–Terminal Fragment," *Biochemistry* 31:5621–5631 (Jun. 1992).

Cardelli, M.B., et al., "Chelation Therapy: Unproved Modality in the Treatment of Alzheimer–Type Dementia," *J. Am. Geriatr. Soc.* 33:548–551, American Geriatric Society (1985).

Ishii, T., and Bannai, S., "The Synergistic Action of the Copper Chelator Bathocuproine Sulphonate and Cysteine in Enhancing Growth of L1210 Cells In Vitro," *J. Cell. Physiol.* 125:151–155, Alan R. Liss, Inc. (1985).

Kruck, T.P.A., et al., "Suppression of deferoxamine mesylate treatment–induced side effects by coadministration of isoniazid in a patient with Alzheimers's disease subject to aluminum removal by ionspecific chelation," *Clin. Pharmacol. Ther.* 48:439–446, Mosby–Year Book, Inc. (1990).

Merck & Co., Inc., "Trientine," Entry 9579, *The Merck Index: An Encyclopedia of Chemicals, Drugs, and Biologicals, 11th Edition*, Budavari, S., et al., eds., Merck & Co., Inc., Rahway, NJ, p. 1521 (1989).

Van Reyk, D.M., and Dean, R.T., "The Iron–selective Chelator Desferal Can Reduce Chelated Copper," *Free Rad. Res.* 24:55–60, Harwood Academic Publishers GmbH (1996).

* cited by examiner

A

B

SEQUENCE LISTING

```
<160> NUMBER OF SEQ ID NOS:   1

<210> SEQ ID NO 1
<211> LENGTH: 48
<212> TYPE: PRT
<213> ORGANISM: Human amyloid protein precursor
<220> FEATURE:
<221> NAME/KEY: PEPTIDE
<222> LOCATION: (4)..(45)
<223> OTHER INFORMATION: A beta

<400> SEQUENCE: 1

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val Ile Ala Thr Val Ile
        35                  40                  45
```

METHODS FOR IDENTIFYING AN AGENT THAT INHIBITS OXYGEN-DEPENDENT HYDROGEN PEROXIDE FORMATION ACTIVITY BUT DOES NOT INHIBIT SUPEROXIDE-DEPENDENT HYDROGEN PEROXIDE FORMATION

CROSS-REFERENCE TO RELATED APPLICATIONS

This application is a continuation-in-part of U.S. application Ser. No. 09/380,704, filed Sep. 8, 1999 pending, which is the U.S. National Phase application of International Application No. PCT/US98/04683, filed Mar. 11, 1998, which claims priority to U.S. application Ser. No. 08/816,122, filed Mar. 11, 1997, now abandoned.

This application claims the benefit of U.S. Provisional Application No. 60/131,579, filed Apr. 29, 1999.

All of the above-mentioned applications, including the international application, are hereby incorporated by reference in their entirety.

STATEMENT AS TO RIGHTS TO INVENTIONS MADE UNDER FEDERALLY-SPONSORED RESEARCH AND DEVELOPMENT

Part of the work performed during the development of this invention utilized U.S. Government Funds under Grant No. R29AG12686 from the National Institutes of Health. The government may have certain rights in this invention.

BACKGROUND OF THE INVENTION

The neuropathology of Alzheimer's disease (AD) is characterized by marked neocortical Abeta deposition and signs of oxidative stress. Metabolic signs of oxidative stress in the neocortex of AD patients, widespread oxygen radical-mediated brain damage, systemic signs of oxidative stress and the response of antioxidant systems have all been observed in AD (Martins, R. N., et al., *J. Neurochem.* 46:1042–1045 (1986); Smith, M. A., et al., *Nature* 382:120–121 (1996); Ceballos-Picot, I., et al., *Free Radic. Biol. Med.* 20(4):579–87 (1996); Nunomura, A., et al., *J. Neurosci.* 19(6):1959–64 (1999)). In fact, amelioration of oxidation injury maybe the basis for the clinical benefit of vitamin E treatment in AD subjects (Sano, M., et al., *N. Engl. J. Med.* 336:1216–1222 (1997)).

A$\beta$ is a dimer that simultaneously binds Cu and Zn. (Huang, X., et al., *J. Biol. Chem.* 272:26464–26470 (1997); Atwood, C. S., et al., *Journal of Biological Chemistry* 273:12817–12826 (1998); Lovell, M. A., et al., *J. Neurol. Sci.* 158(1):47–52 (1998); Huang, X., et al., *Biochemistry* 38:7609–7616 (1999); Garzon-Rodriguez, W., et al., *J. Biol. Chem.* 272:21037–21044 (1997)). It is released from cells by oxidative stress, but its normal function and role in AD are unclear. Polymers of Abeta (A$\beta$), the 4.3 kD, 39–43 amino acid peptide product of the transmembrane protein, amyloid protein precursor (APP), are the main components extracted from the neuritic and vascular amyloid deposits found in the brains of those afflicted with AD. A$\beta$ deposits are usually most concentrated in regions of high neuronal cell death, and may be present in various morphologies, including amorphous deposits, plaque amyloid, and amyloid congophilic angiopathy (Masters, C. L., et al., *EMBO J.* 4:2757(1985); Masters, C. L., et al., *Proc. Natl. Acad. Sci. USA* 82: 4245 (1985)). A$\beta$ deposits are decorated with inflammatory response proteins. In addition, biochemical markers of severe oxidative stress, such as peroxidation adducts, advanced glycation end-products, and protein crosslinking, are located in close proximity to the deposits.

To date, the cause of A$\beta$ deposits is unknown. However, it is believed that preventing the deposit formation may be a means of treating AD since growing evidence suggests that A$\beta$ deposits are intimately associated with the neuronal demise that leads to dementia in AD. More specifically, genetic studies have strongly implicated the 42 residue form of A$\beta$ (A$\beta_{1-42}$) in the pathogenesis of AD (Maury, C. P. J., *Lab. Investig.* 72:4–16 (1995); Multhaup, G., et al., *Nature* 325:733–736 (1987)). A$\beta_{1-42}$, while a minor component of biological fluids, is highly concentrated in A$\beta$ deposits. This suggests that A$\beta_{1-42}$ is more pathogenic than other neurotoxic A$\beta$ species. See, e.g., Kuo, Y-M., et al., *J. Biol. Chem.* 271:4077–81 (1996); Roher, A. E., et al., *J. Biol. Chem.* 271:20631–20635 (1996).

The systemic deposition of amyloid is usually associated with an inflammatory response (Pepys, M. B. and Baltz, M. L., *Adv. Immunol.* 34:141–212 (1983); Cohen, A. S., in *Arthritis and Allied Conditions*, D. J. McCarty, ed., Lea and Febiger, Philadelphia (1989), pp. 1273–1293; Kisilevsky, R., *Lab. Investig.* 49:381–390 (1983)). For example, serum amyloid A, one of the major acute phase reactant proteins that is elevated during inflammation, is the precursor of amyloid A protein that is deposited in various tissues during chronic inflammation, leading to secondary amyloidosis (Gorevic, P. D., et al., *Ann. NY Acad. Sci.*:380–393 (1982)). An involvement of inflammatory mechanisms has been suggested as contributing to plaque formation in AD (Kisilevsky, R., *Mol. Neurobiol.* 49:65–66 (1994)). Acute-phase proteins such as alpha I -antichymotrypsin and c-reactive protein, elements of the complement system and activated microglial and astroglial cells are consistently found in AD brains.

The mechanism underlying the formation of neurotoxic A$\beta$ amyloid remains unresolved. The overexpression of A$\beta$ alone cannot sufficiently explain amyloid formation, since the concentration of A$\beta$ required for aggregation is not physiologically plausible. Moreover, alterations in the neurochemical environment are required for amyloid formation since the presence of A$\beta_{1-42}$ is normal in biological fluids such as cerebrospinal fluid (CSF) (Shoji, M., *Science* 258: 126 (1992); Golde et al., *Science* 255(5045): 728–730 (1992); Seubert, P. et al., *Nature* 359: 325 (1992); Haass et al., *Nature* 359: 322 (1992)).

Studies into the neurochemical vulnerability of A$\beta$ to form amyloid suggest altered zinc and [H$^+$] homeostasis as the most likely explanations for amyloid formation since A$\beta$ is rapidly precipitated under mildly acidic conditions in vitro (pH 3.5–6.5) (Barrow C. J. & Zagorski M. G., *Science* 253:179–182 (1991); Fraser, P. E., et al., *Biophys. J.* 60:1190–1201 (1991); Barrow, C. J., et al., *J. Mol. Biol.* 225:1075–1093 (1992); Burdick, D., *J. Biol. Chem.* 267:546–554 (1992); Zagorski, M. G. and Barrow, C. J., *Biochemistry* 31:5621–5631 (1992); Kirshenbaum, K. and Daggett, V., *Biochemistry* 34:7629–7639 (1995); Wood, S. J., et al., *J. Mol. Biol.* 256:870–877 (1996)), and since the presence of redox inactive Zn(II) and, to a lesser extent, redox active Cu(II) and Fe(III), markedly increases the precipitation of soluble A$\beta$ (Bush, A. I., et al., *J. Biol. Chem.* 268:16109 (1993); Bush, A. I., et al., *J. Biol. Chem.* 269:12152 (1994); Bush, A. I., et al., *Science* 265:1464 (1994); Bush, A. I., et al., *Science* 268:1921 (1995)). Zinc has an abnormal metabolism in AD and is highly concentrated in brain regions where A$\beta$ aggregates.

However, the complete reversibility of Zn(II)-induced A$\beta_{1-40}$ aggregation in the presence of divalent metal ion chelating agents suggests that zinc binding is a reversible, normal function of Aβ and implicates other neurochemical mechanisms in the formation of Aβ deposits. A process involving irreversible Aβ aggregation, such as the crosslinking of Aβ monomers in the formation of Aβ polymeric species present in amyloid plaques, is thus a more plausible explanation for the formation of neurotoxic Aβ deposits.

The reduction by APP of copper (II) to copper (I) may lead to irreversible Aβ aggregation and crosslinking. More specifically, this reaction may promote an environment that enhances the production of hydroxyl radicals, which may contribute to oxidative stress in AD (Multhaup, G., et al.,*Science* 271:1406–1409 (1996)). A precedent for abnormal Cu metabolism already exists in the neurodegenerative disorders of Wilson's disease and Menkes' syndrome and possibly in familial amyotrophic lateral sclerosis (Tanzi, R. E. et al., *Nature Genetics* 5:344 (1993)).

Although the fundamental pathology, genetic susceptibility and biology associated with AD are becoming clearer, a rational chemical and structural basis for developing effective drugs to prevent or cure the disease remains elusive. While the genetics of AD indicate that the metabolism of Aβ is intimately associated with the pathogenesis of the disease as indicated above, drugs for the treatment of AD have so far focused on "cognition enhancers" which do not address the underlying disease processes.

SUMMARY OF THE INVENTION

The present invention is directed to the identification of agents that can be used to decrease the neurotoxicity of Aβ and the formation of Aβ polymers, and to the use of such agents to develop methods of preventing, treating or alleviating AD and/or the symptoms of AD. More specifically, the present invention is directed to the identification of agents that could be used to treat AD.

Because the ability of Aβ to function as an antioxidant, i.e., to generate $H_2O_2$ from $O_2^-$ may, in many instances, be beneficial, the invention also relates to a method for identifying an agent to be used in the treatment and/or prevention of AD and symptoms thereof, wherein said agent is capable of interfering with the interaction of $O_2$ and Aβ to generate $H_2O_2$ without interfering with the SOD-like activity of Aβ, i.e., the ability of Aβ to function as an antioxidant.

Thus, the invention relates to a method for the identification of an agent to be used in the treatment and/or prevention of AD and/or symptoms thereof, wherein the agent inhibits oxygen-dependent hydrogen peroxide formation activity, but does not inhibit the superoxide-dependent hydrogen peroxide formation, the method comprising:
  (a) adding the agent to an Aβ-containing sample;
  (b) determining whether the agent is capable of inhibiting dissolved oxygen-dependent hydrogen peroxide formation; and
  (c) determining whether the agent is capable of not inhibiting the Aβ-catalyzed superoxide-dependent hydrogen peroxide formation.

In a preferred embodiment, the method of determining whether the agent is capable of not inhibiting the superoxide-dependent hydrogen peroxide formation is conducted using pulse radiolysis or the NBT assay.

In a preferred embodiment, the determination of the ability of the agent to inhibit the Aβ-catalyzed superoxide-dependent hydrogen peroxide formation is made by determining whether Aβ is capable of catalytically producing Cu(I), Fe(II) or $H_2O_2$.

The invention further relates to a method for the identification of an agent to be used in the treatment and/or prevention of AD and/or symptoms thereof, wherein the agent is capable of altering the production of Cu(I) by Aβ, the method comprising:
  (a) adding Cu(II) to a first Aβ sample;
  (b) allowing the first sample to incubate for an amount of time sufficient to generate Cu(I);
  (c) adding Cu(II) to a second Aβ sample, the second sample additionally comprising a candidate pharmacological agent;
  (d) allowing the second sample to incubate for the same amount of time as the first sample;
  (e) determining the amount of Cu(I) produced by the first and second samples; and
  (f) comparing the amount of Cu(I) produced by the first sample to the amount of Cu(I) produced by the second sample;
whereby a difference in the amount of Cu(I) produced by the sample as compared to the second sample indicates that the candidate pharmacological agent has altered the production of Cu(I) by Aβ.

In a preferred embodiment, the amount of Cu(I) present in the first and second samples is determined by
  (a) adding a complexing agent to the first and second samples, wherein the complexing agent is capable of combining with Cu(I) to form a complex compound, wherein the complex compound has an optimal visible absorption wavelength;
  (b) measuring the absorbencies of the first and second samples; and
  (c) calculating the concentration of Cu(I)in the first and second samples using the absorbencies obtained in (b).

In a preferred embodiment, the method is performed in a microtiter plate, and the absorbency measurements are performed by a plate reader.

In a preferred embodiment, two or more different test candidate agents are simultaneously evaluated for an ability to alter the production of Cu(I) by Aβ.

In a preferred embodiment, the first and second Aβ samples are biological samples such as CSF.

The method further relates to the identification of an agent to be used in the treatment and/or prevention of AD and/or symptoms thereof, wherein the agent is capable of altering the production of Fe(II) by Aβ, the method comprising:
  (a) adding Fe(III) to a first Aβ sample;
  (b) allowing the first sample to incubate for an amount of time sufficient to generate Fe(II);
  (c) adding Fe(III) to a second Aβ sample, the second sample additionally comprising a candidate pharmacological agent;
  (d) allowing the second sample to incubate for the same amount of time as the first sample;
  (e) determining the amount of Fe(II) produced by the first and second samples; and
  (f) comparing the amount of Fe(II) present in the first sample to the amount of Fe(II) present in the second sample;
whereby a difference in the amount of Fe(II) present in the first sample as compared to the second sample indicates that the candidate pharmacological agent has altered the production of Fe(II) by Aβ.

In a preferred embodiment, the amount of Fe(II) present in the first and second samples is determined by
  (a) adding a complexing agent to the first and second samples, wherein the complexing agent is capable of combining with Fe(II) to form a complex compound, wherein the complex compound has an optimal visible absorption wavelength;
(b) measuring the absorbencies of the first and second samples; and
(c) calculating the concentration of Fe(II) in the first and second samples using the absorbencies obtained in (b).

In a preferred embodiment, the method is performed in a microtiter plate, and the absorbency measurements are performed by a plate reader.

In a preferred embodiment, two or more different test candidate agents are simultaneously evaluated for an ability to alter the production of Fe(II) by Aβ.

In a preferred embodiment, the first and second Aβ samples are biological samples such as CSF.

The invention further relates to a method for the identification of an agent to be used in the treatment and/or prevention of AD and/or symptoms thereof, wherein the agent is capable of altering the production of $H_2O_2$ by Aβ, the method comprising:
(a) adding Cu(II) or Fe(III) to a first Aβ sample;
(b) allowing the first sample to incubate for an amount of time sufficient to generate $H_2O_2$;
(c) adding Cu(II) or Fe(III) to a second AD sample, the second sample additionally comprising a candidate pharmacological agent;
(d) allowing the second sample to incubate for the same amount of time as the first sample;
(e) determining the amount of $H_2O_2$ produced by the first and second samples; and
(f) comparing the amount of $H_2O_2$ present in the first sample to the amount of $H_2O_2$ present in the second sample;
whereby a difference in the amount of $H_2O_2$ present in the first sample as compared to the second sample indicates that the candidate pharmacological agent has altered the production of $H_2O_2$ by Aβ.

In a preferred embodiment, the Aβ samples of (a) and (b) are a biological fluid such as CSF.

In a preferred embodiment, the determination of the amount of $H_2O_2$ present in the first and second samples is determined by
(a) adding catalase to a first aliquot of the first sample in an amount sufficient to break down all of the $H_2O_2$ generated by the sample;
(b) adding TCEP, in an amount sufficient to capture all of the $H_2O_2$ generated by the samples, to
(i) a first aliquot of the first sample;
(ii) a second aliquot of the first sample; and
(iii) the second sample;
(c) incubating the samples obtained in (b) for an amount of time sufficient to allow the TCEP to capture all of the $H_2O_2$;
(d) adding DTNB to the samples obtained in (c);
(e) incubating the samples obtained in (d) for an amount of time sufficient to generate TMB;
(f) measuring the absorbencies at 412 nm of the samples obtained in (e); and
(g) calculating the concentration of $H_2O_2$ in the first and second samples using the absorbencies obtained in (f).

In a preferred embodiment, the method is performed in a microtiter plate, and the absorbency measurements are performed by a plate reader.

In a preferred embodiment, two or more different test candidate agents are simultaneously evaluated for an ability to alter the production of $H_2O_2$ by Aβ.

The invention further relates to a method for the identification of an agent to be used in the treatment and/or prevention of AD and/or symptoms thereof, wherein the agent is capable of reducing the toxicity of Aβ, the method comprising:
(a) adding Aβ to a first cell culture;
(b) adding Aβ to a second cell culture, the second cell culture additionally containing a candidate pharmacological agent;
(c) determining the level of neurotoxicity of Aβ in the first and second samples; and
(d) comparing the level of neurotoxicity of Aβ in the first and second samples,
whereby a lower neurotoxicity level in the second sample as compared to the first sample indicates that the candidate pharmacological agent has reduced the neurotoxicity of Aβ, and is thereby capable of being used to treat and/or prevent AD and/or symptoms thereof.

In a preferred embodiment, neurotoxicity of Aβ is determined by using an MTT assay, an LDH release assay or a Live/Dead assay, e.g., Live/Dead EukoLight Viability/Cytotoxicity Assay, commercially available from Molecular Probes, Inc. (Eugene, Oreg.).

In a preferred embodiment, the cells are rat cancer cells or rat primary frontal neuronal cells.

The invention further relates to a kit for determining whether an agent is capable of altering the production of Cu(I) by Aβ which comprises a carrier means being compartmentalized to receive in close confinement therein one or more container means wherein
(a) the first container means contains a peptide comprising Aβ peptide;
(b) a second container means contains a Cu(II) salt; and
(c) a third container means contains BC anion.

In a preferred embodiment, the Aβ peptide is present as a solution in an aqueous buffer or a physiological solution, at a concentration from about 10 $\mu$M to about 25 $\mu$M.

The invention further relates to a kit for determining whether an agent is capable of altering the production of Fe(II) by Aβ which comprises a carrier means being compartmentalized to receive in close confinement therein one or more container means wherein
(a) the first container means contains a peptide comprising Aβ peptide;
(b) a second container means contains an Fe(III) salt; and
(c) a third container means contains BP anion.

In a preferred embodiment, the Aβ peptide is present as a solution in an aqueous buffer or a physiological solution, at a concentration from about 10 $\mu$M to about 25 $\mu$M.

The invention further relates to a kit for determining whether an agent is capable of altering the production of $H_2O_2$ by Aβ which comprises a carrier means being compartmentalized to receive in close confinement therein one or more container means wherein
(a) the first container means contains a peptide comprising Aβ peptide;
(b) a second container means contains a Cu(II) salt;
(c) a third container means contains TCEP; and
(d) a fourth container means contains DTNB.

In a preferred embodiment, the Aβ peptide is present as a solution in an aqueous buffer or a physiological solution, at a concentration from about 10 $\mu$M to about 25 $\mu$M.

The invention further relates to a method for the identification of an agent to be used in the treatment and/or prevention of AD and/or symptoms thereof, wherein the agent is capable of inhibiting redox-reactive metal-mediated crosslinking Aβ, the method comprising:

(a) adding a redox-reactive metal to a first Aβ sample;

(b) allowing the first sample to incubate for an amount of time sufficient to allow Aβ crosslinking;

(c) adding the redox-reactive metal to a second Aβ sample, the second sample additionally comprising a candidate pharmacological agent;

(d) allowing the second sample to incubate for the same amount of time as the first sample;

(e) removing an aliquot from each of the first and second samples; and (f) determining presence or absence of crosslinking in the first and second samples, whereby an absence of Aβ crosslinking in the second sample as compared to the first sample indicates that the candidate pharmacological agent has inhibited Aβ crosslinking.

In a preferred embodiment, at (f), a western blot analysis is performed to determine the presence or absence of crosslinking in the first and second samples.

The invention further relates to a method of treating AD and/or symptoms thereof, comprising administering to a patient in need thereof an effective amount of an agent identified by any one or combination of the screening assays described above.

BRIEF DESCRIPTION OF THE FIGURES

FIG. 2A is a graph showing a turbidometric analysis of pH effect on metal ion-induced $Aβ_{1-40}$ aggregation. FIG. 2B is a graph showing the proportion of soluble $Aβ_{1-40}$ remaining in the supernatant after incubation with various metal ions. FIG. 2C is a graph showing the proportion of soluble $Aβ_{1-40}$ remaining in the supernatant after incubation with various metal ions, where high metal ion concentrations were used.

FIG. 4A is a graph showing the proportion of soluble $Aβ_{1-40}$ remaining in the supernatant following incubation at various pHs in PBS±Zn(II). FIG. 4B is a graph showing the proportion of soluble $Aβ_{1-40}$ remaining in the supernatant following incubation at various pHs with different Cu(II)concentrations. FIG. 4C is a graph showing the relative aggregation of nm concentrations of $Aβ_{1-40}$ at pH 7.4 and 6.6 with different Cu(II) concentrations.

FIG. 5A is a graph showing a turbidometric analysis of Cu(II)-induced $Aβ_{1-40}$ aggregation at pH 7.4 reversed by successive cycles of chelator. FIG. 5B is a graph showing a turbidometric analysis of the reversibility of Cu(II)-induced $Aβ_{1-40}$ aggregation as the pH cycles between 7.4 and 6.6.

FIG. 13A illustrates that primary fibroblasts cultured from Tg C100.V717F mice (open circles) were more resistant to increasing concentrations of xanthine oxidase than Tg C100.WT mice fibroblasts (filled circles) (Student's t-test, P<0.01). FIG. 13B illustrates that nanomolar concentrations of synthetic $Aβ_{1-42}$ increased the resistance of Tg C100.WT fibroblasts to superoxide damage (Student's t-test, P<0.01). This effect was comparable to treatment with 50 U/ml SOD1 (Student's t-test, P<0.05).

FIG. 15A shows the effect of $CuAβ_{1-40}$ and $CuZnAβ_{1-40}$ upon the rate of superoxide decay ($k_{obs}$). FIG. 15B shows the effect of $CuAβ_{1-42}$ and $CuZnAβ_{1-42}$ upon the rate of superoxide decay ($k_{obs}$). FIG. 15C shows the dismutase activity ($k_{cat}$) values plotted against corresponding Cu equivalents bound to $Aβ_{1-40}$ (open squares) or $Aβ_{1-42}$ (filled squares), indicating that the $k_{cat}$ is dependent upon peptide-mediated factors, and is not simply proportional to bound Cu equivalents. Values are taken from Table 1. See Example 3.

DETAILED DESCRIPTION OF THE PREFERRED EMBODIMENT

Figure 1:
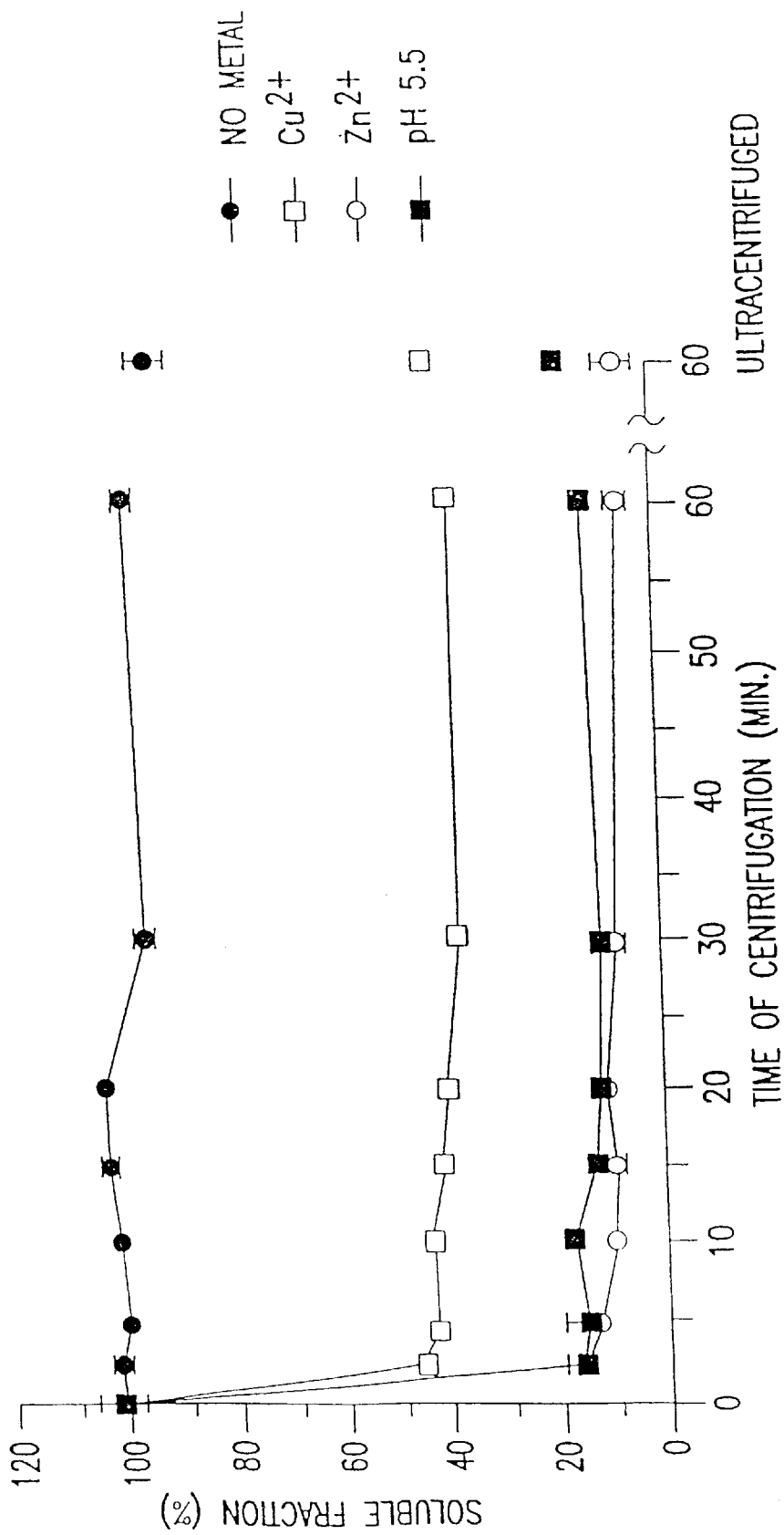
FIG. 1 is a graph showing the proportion of soluble $Aβ_{1-40}$ remaining following centrifugation of reaction mixtures.

The present invention relates to the unexpected discovery that Aβ peptides directly produce oxidative stress through the generation of abundant reactive oxygen species (ROS). The production of ROS occurs by a metal (Cu and/or Fe) dependent, pH-mediated mechanism, wherein Aβ reduces Cu(II) to Cu(I) or Fe(III) to Fe(II). In AD and aged brains, this reaction subsequently produces $H_2O_2$ using dissolved $O_2$ as a substrate (Huang, 1997 #10132; Huang, 1997 #9963) which may reflect a loss of specificity for its normal substrate, $O_2^-$, and lead to the abnormal generation of $H_2O_2$ which may be associated with the aggregation of the peptide. Thus, Aβ may be a superoxide scavenger that becomes corrupted by an excess of its product, $H_2O_2$, causing autooxidative damage and protein accumulation (Atwood, C. S., et al., Soc. Neurosci. Abstr. 23: 1883 (1997)).

Definitions

To provide a clear understanding of the specification and claims, the following definitions are provided.

Aβ peptide is also known in the art as Aβ, β protein, β-A4 and A4. In the present invention, the Aβ peptide may be comprised of peptides $Aβ_{1-39}$, $Aβ_{1-40}$, $Aβ_{1-41}$, $Aβ_{1-42}$ and $Aβ_{1-43}$. In a preferred embodiment, Aβ is selected from the group consisting of $Aβ_{1-39}$, $Aβ_{1-40}$, $Aβ_{1-41}$, $Aβ_{1-42}$, $Aβ_{1-43}$ and mixtures thereof. Even more preferably, Aβ is $Aβ_{1-40}$ or $Aβ_{1-42}$. In a preferred embodiment, Aβ is $Aβ_{1-42}$. The most preferred embodiment of the invention makes use of $Aβ_{1-40}$. However, any of the Aβ peptides may be employed according to the present invention. The sequence of Aβ is found in C. Hilbich et al., J. Mol. Biol. 228:460–473 (1992). While Aβ$_{1-42}$ is a minor soluble species, it is more fibrillogenic, enriched in interstitial Aβ deposits, and overproduced in familial AD (Suzuki, N., et al., *Science* 264:1336–1340 (1994)).

All the redox properties of Aβ$_{1-40}$ (the most abundant form of soluble Aβ) are exaggerated in Aβ$_{1-42}$. The exaggerated redox activity of Aβ$_{1-42}$ and its enhanced ability to generate ROS likely explain its neurotoxic properties. Interestingly, the rat homologue of Aβ, which has 3 substitutions that have been shown to attenuate zinc binding and zinc-mediated aggregation, exhibits less redox activity than its human counterpart. This may explain why the rat is exceptional in that it is the only mammal that does not exhibit amyloid pathology with age. All other mammals analyzed to date possess the human Aβ sequence.

Amyloid, as is commonly known in the art and as is intended in the present specification, is a form of aggregated protein.

Aβ Amyloid is an aggregated Aβ peptide. It is found in the brains of those afflicted with AD and/or Down's Syndrome and may accumulate following head injuries.

Physiological solution as used in the present specification means a solution comprising compounds at physiological pH, about 7.4, which closely represents a bodily or biological fluid, such as CSF, blood, plasma, etc.

Zn(II), Fe(III), Fe(II), Cu(II) and Cu(I), unless otherwise indicated, means salts of the metal, i.e., the metal in any form, soluble or insoluble.

Biological fluid means fluid obtained from a person or animal which is produced by that person or animal. Examples of biological fluids include, but are not limited to, cerebrospinal fluid (CSF), blood, serum and plasma. In the present invention, "biological fluid" includes the entire biological fluid or any fraction of such fluid derived by purification by any means, e.g., ultrafiltration or chromatography.

SOD-like Activity of Aβ Peptides

Figure 12:
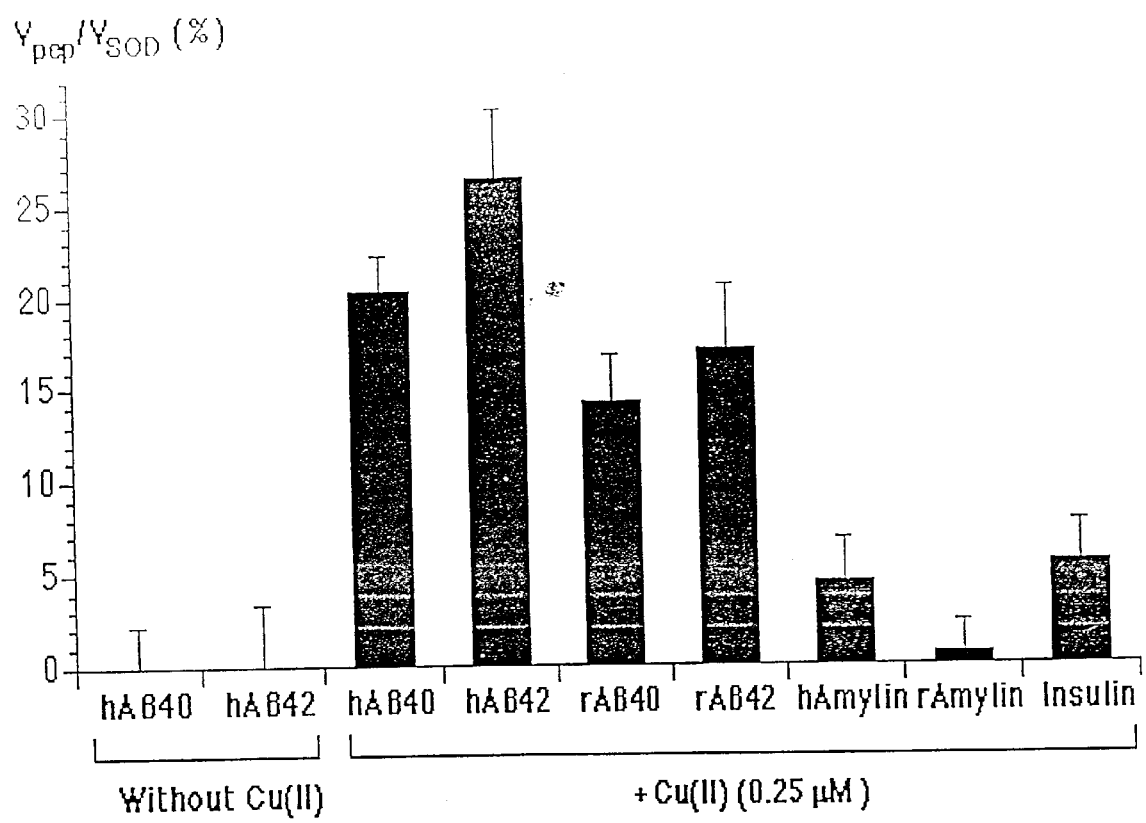
FIG. 12 is a bar graph depicting the anti-superoxide activities of various Aβ polypeptides in vitro.
Figure 13A:
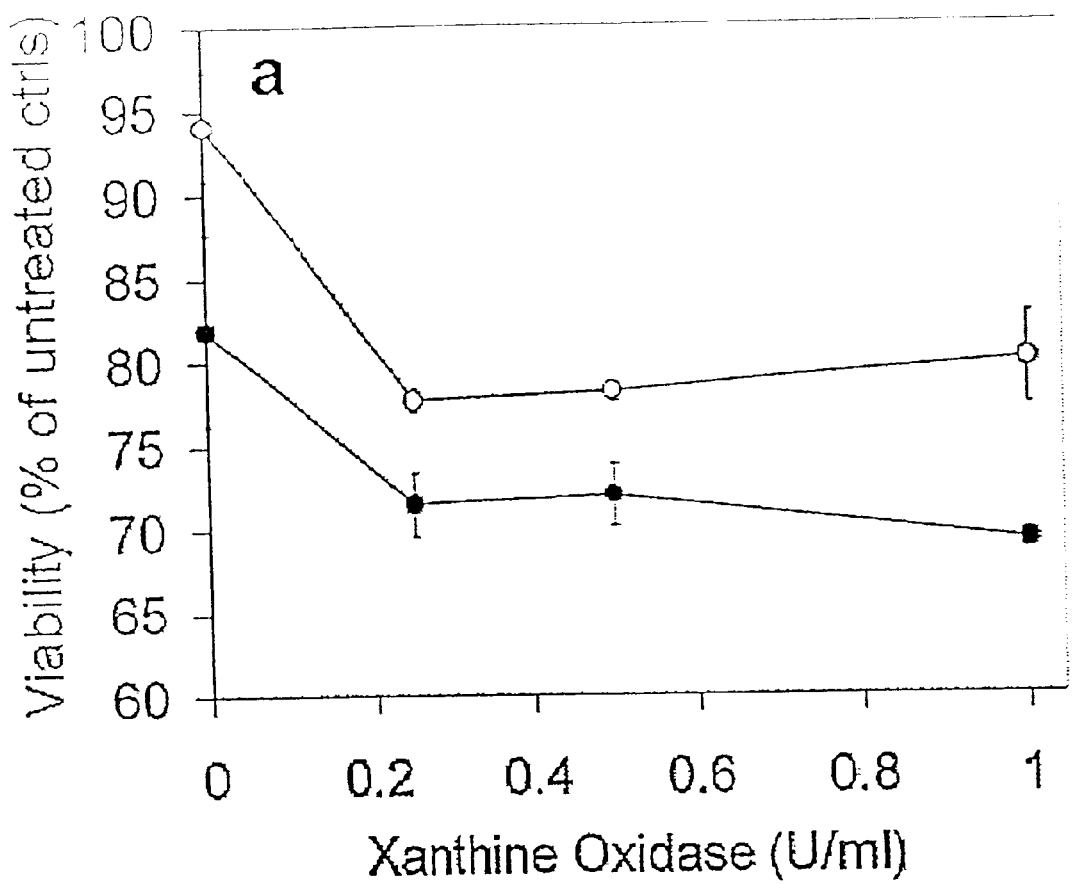
FIGS. 13A and 13B are graphs depicting the effect of superoxide production on the viability of fibroblasts from C100 transgenic mice.
Figure 13B:
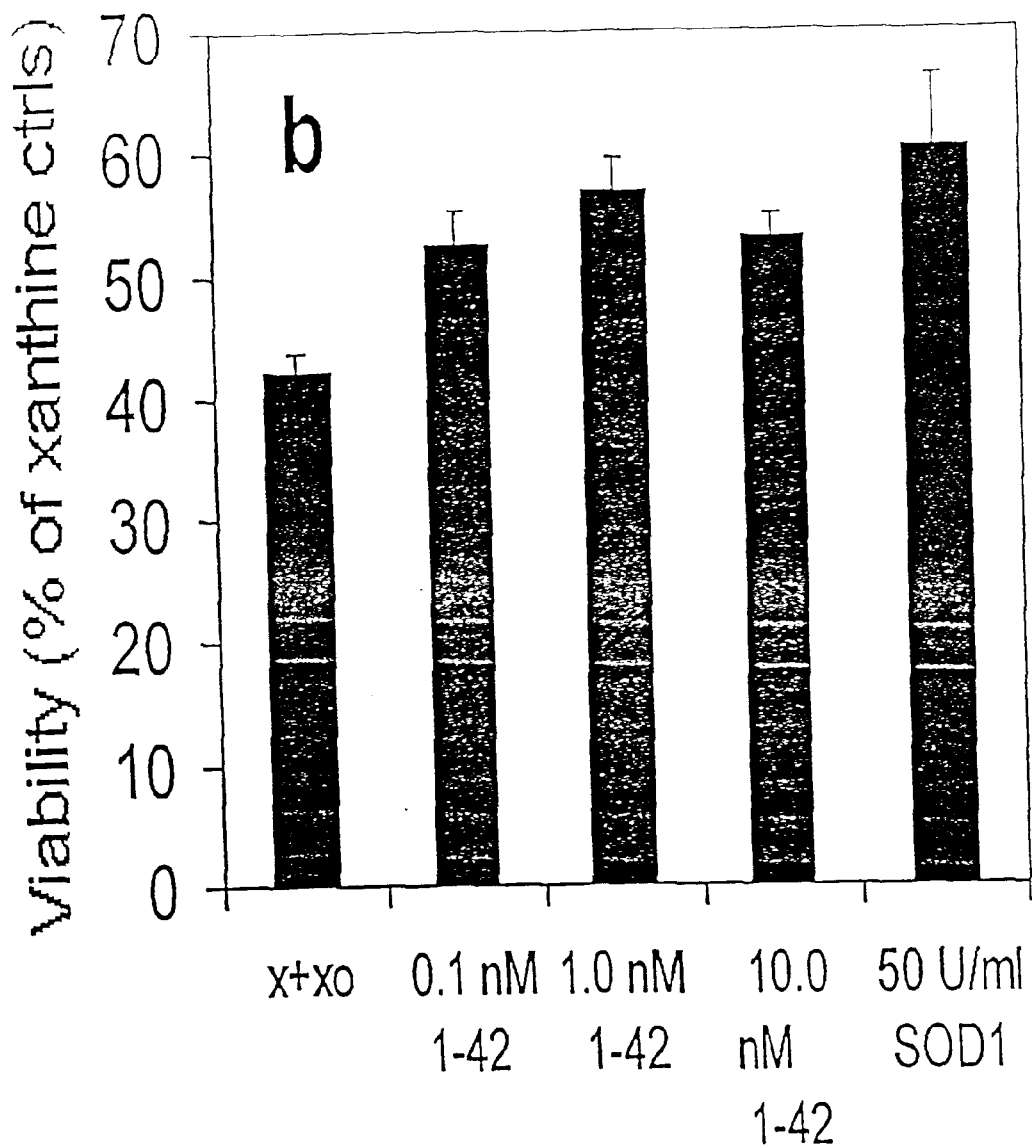

The metal-dependent chemistry of Aβ-mediated superoxide dismutation is reminiscent of the activity of superoxide dismutase (SOD). Superoxide dismutase 1 (SOD1, also known as Cu/Zn SOD), simultaneously binds Cu and Zn, and uses the Cu(II) active site to transfer electrons to superoxide ($O_2^-$), resulting in $H_2O_2$ generation (Uchida, K. and Kawakishi, S., *J. Biol. Chem.* 269:2405–2410 (1994)). Hence, by binding to Cu(II) with high affinity, Aβ might also be able to use $O_2^-$ as a substrate. Example 3 sets forth a test for this possibility by replacing SOD1 with Aβ in a classic assay for superoxide scavenging activity (the NBT assay) (Goldstein, S., et al., *Free Radic Biol Med* 4: 295–303 (1988)) (FIG. 12). Interestingly, mutations of SOD1 cause amyotrophic lateral sclerosis, another neurodegenerative disorder (Rosen, D., et al., *Nature* 364:362 (1993)). SOD1 is predominantly intracellular, whereas Aβ is constitutively found in the extracellular spaces where it accumulates.

The SOD-like activity of Aβ in living systems is currently under investigation, and data so far have revealed that both cell cultures and transgenic animals overexpressing Aβ$_{1-42}$ (due to APP mutation or due to presenilin-1 overexpression) are relatively resistant to superoxide-mediated stressors (Bush, A. I., et al., *Soc. Neurosci. Abstr.* 25: 14 (1999)). These in vivo findings may support a role for Aβ as a superoxide antioxidant, where the generation of the peptide in vivo may be part of a cellular antioxidant response system.

If the physiological function of Aβ is a superoxide antioxidant, then longer forms of Aβ, e.g., 1–42, might be generated as a stronger antioxidant. The data (Example 3) indicate that Aβ$_{1-42}$ appears to be more of an avid scavenger for superoxide than Aβ$_{1-40}$, possibly by virtue of its ability to bind Cu(II) with a higher affinity than Aβ$_{1-40}$. The higher affinity of Aβ$_{1-42}$ for Cu(II) may be mediated by the increased β-sheet content of the longer peptide (Barrow, C. J., et al., *J. Mol. Biol.* 225:1075–1093 (1992)), a common structural feature of redox active Cu(II) binding sites in cuproproteins including SOD1 (Frausto da Silva, J. J. R., and Williams, R. J. P., *The Biological Chemistiy of the Elements*, Clarendon Press, Oxford (1991)). It is hypothesized that the generation of a greater proportion of Aβ$_{1-42}$ may reflect a physiological response to a more severe oxidation stress, which may be why increased Aβ$_{1-42}$ is generated as a response to head injury (Raby, C. A., et al., *J. Neurochem.* 71(6):2505–9 (1998)) or apoptosis associated with familial AD mutations in the presenilins (Wolozin, B., et al., *Science* 274(5293):1710–3 (1996)). This raises the intriguing possibility that increased Aβ$_{1-42}$ generation caused by familial AD mutations perhaps represents a survival response with deleterious long-term consequences and may therefore be an instance of molecular antagonistic pleiotropy. Thus, it is further hypothesized that, like SOD1 (Yim, M. B., et al., *Proc. Natl. Acad. Sci. USA* 93(12): 5709–14 (1996)), Aβ may be an antioxidant in health and a prooxidant in disease. The mixed antioxidant and prooxidant properties of Aβ may explain why histological amyloid deposition correlates poorly with dementia (Terry, R. D., et al., *Ann. Neurol.* 30:572–580 (1991)). Aβ has been regarded as a pro-oxidant at micromolar concentrations where its neurotoxic effects in cell culture experiments are mediated by elevated cellular hydrogen peroxide concentrations (Yankner, B. A., et al., *Science* 250:279–282 (1990); Behl, C., et al., *Cell* 77: 817–827 (1994)). However, the peptide is paradoxically neurotrophic at lower (nanomolar) concentrations (Yankner, B. A., et al., *Science* 250:279–282 (1990)).

Aβ, like SOD1, is a dimeric protein that reversibly binds Cu and Zn with submicromolar affinity and has a weaker affinity for Fe(III) (Bush, A. I., et al., *J. Biol. Chem.* 269:12152–12158 (1994); Bush, A. I., et al., *Science.* 265:1464–1467 (1994); Huang, X., et al, *J. Biol. Chem.* 272:26464–26470 (1997); Atwood, C. S., et al., *Journal of Biological Chemistry* 273:12817–12826 (1998)) which may explain why Cu (approximately 0.4 mM), Zn (approximately 1.0 mM) and Fe (approximately 1.0 mM) are so heavily enriched in Aβ deposits in AD (Lovell, M. A., et al., *J. Neurol Sci* 158(1):47–52 (1998)). Further, Aβ reduces Cu(II) and Fe(III) and it has recently been found that Aβ possesses a strongly positive formal reduction potential (+550 mV vs Ag/AgCl) (Huang et al., submitted).

In view of the ability to bind Cu and Zn and reduce Cu(II) and Fe(III), the $O_2^-$ dismutation behavior of Aβ was studied in the psec time-scale using laser pulse photolysis. These experiments have shown that Aβ exhibits Fe/Cu-dependent SOD-like activity with rate constants of dismutation at approximately $10^8$ M$^{-1}$ sec$^{-1}$, e.g., 2.2×$10^8$ M$^{-1}$ sec$^{-1}$, which are strikingly similar to SOD1. The activity is markedly enhanced by the metallation of the peptide with Zn(II). Hence, Aβ appears to be a good candidate to possess the same function as SOD1. Further, like mutant SOD1 in familial amyotrophic lateral sclerosis, Aβ could be another superoxide scavenger that aggregates in association with neuronal damage. This may explain why oxidative stress causes its release by cells (Frederikse, P. H., et al., *J. Biol. Chem.* 271: 10169 (1996)). However, if Aβ is involved in the reaction to oxidative stress, or if the $H_2O_2$ clearance is compromised at the cellular level, Aβ will accumulate, recruiting more $O_2$ and producing more ROS leading to a vicious cycle and localizing tissue peroxidation damage and protein crosslinking. It appears that as the concentration of Aβ rises, the peptide loses specificity for the superoxide substrate, loses dismutase activity (FIGS. 15A and 15B), and begins to generate hydrogen peroxide from oxygen inappropriately.

Hence, the invention relates to identifying agents that will inhibit the Aβ dependent production of large amounts of toxic hydrogen peroxide ($H_2O_2$) from dissolved oxygen ($O_2$) (the "pro-oxidant" Aβ activity), but will not inhibit the beneficial Aβ dependent activity of converting superoxide ($O_2^-$) to $H_2O_2$, which is then degraded by other cellular enzymes (the antioxidant Aβ activity).

A proposed mechanism for free radical and amyloid formation in AD is explained as follows.

Figure 11:
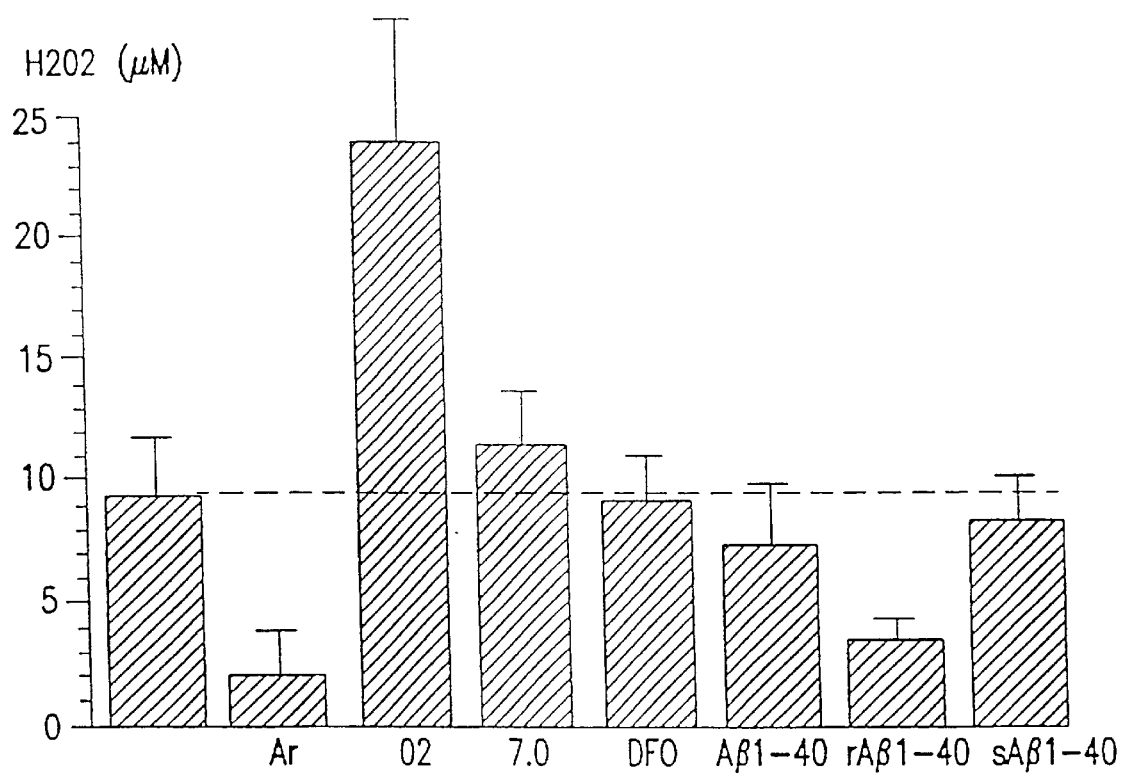
FIG. 11 is a graph showing $H_2O_2$ production by Aβ.

(1) Soluble and precipitated Aβ species possess superoxide dismutase (SOD)-like activity. Superoxide ($O_2^-$), the substrate for the dismutation, is generated both by spillover from mitochondrial respiratory metabolism, and by Aβ itself (FIG. 11). Aβ-mediated dismutation produces hydrogen peroxide ($H_2O_2$), requiring Cu(II) or Fe(III) which are reduced during the reaction.

(2) $H_2O_2$ is relatively stable, freely permeable across cell membranes and contributes to oxidation events at a distance from its generation. Normally, it will be broken down by intercellular catalase and/or glutathione peroxidase into oxygen and water.

(3) However, in aging and AD, levels of $H_2O_2$ are high, and glutathione, catalase and peroxidase activities are low. If $H_2O_2$ is not completely catalyzed, it will react with reduced Cu(I) and Fe(II) in the vicinity of Aβ to generate the ROS, such as the highly reactive hydroxyl radical OH., by Fenton chemistry.

(4) $H_2O_2$/ROS engenders a non-specific stress and inflammatory response in local tissue. Among the neurochemicals that are released from microglia and possibly neurons in this response are Zn(II), Cu(II) and soluble Aβ. Familial AD increases the likelihood that Aβ will be released at this point. Local acidosis is also part of the stress/inflammatory response. These factors combine to make Aβ precipitate and accumulate, presumably so that it may function in situ as a superoxide scavenger, since these factors induce reversible polymerization. Hence, more soluble Aβ species decorate the perimeter of the accumulating plaque deposits.

(5) If Aβ encounters OH., it will covalently crosslink during the oligomerization process, making the accumulation more difficult to resolubilize, and leading to the formation of SDS-resistant oligomers characteristic of plaque amyloid.

(6) If Aβ concentrations rise in the vicinity of a region of oxidative stress, it is likely that the regional concentration of $H_2O_2$ will also rise. If the concentration of $H_2O_2$ becomes too high in proximity to Aβ, then, like SOD1 (Uchida, K. and Kawakishi, S., *J. Biol. Chem.* 269: 2405–2410 (1994); Atwood, C. S., et al., *Soc. Neurosci. Abstr.* 23:1883 (1997)), Aβ will be damaged by $H_2O_2$-mediated oxidation directly or indirectly by Fenton-like chemistry. The damaged peptide may then accumulate, elevating the regional $H_2O_2$ concentrations even further, triggering the release of more Aβ as an antioxidant response, leading to a vicious cycle (Frederikse, P. H., et al., *J. Biol. Chem.* 271:10169–10174 (1996)). The accumulation of damaged Aβ sustains the inappropriate production of hydrogen peroxide from oxygen. The production of abundant free radicals by the accumulating Aβ deposits may further damage many systems and compounds including, but not limited to, metal regulatory proteins, thus compounding the problem. Hence, Aβ deposits could be mixed environments low in superoxide, but high in $H_2O_2$. Thus, Aβ, and particularly $Aβ_{1-42}$, may serve as a quick response Cu/Zn superoxide scavenger that, like SOD1, may become corrupted by its environment leading to neuronal demise.

Importantly, the redox activity of Aβ is not attenuated by precipitation of the peptide, suggesting that, in vivo, Aβ deposits could be capable of generating ROS in situ on an enduring basis. This suggests that the major source of oxidative stress in an AD-affected brain is amyloid deposition which may cause and, in turn, be compounded by, damage to the biometal homeostatic mechanisms in the brain environment. Thus, the accumulation of Aβ in the brain in AD is likely to contribute to oxidative stress in the same way that the accumulation of SOD1 in aggregates may damage the motor neuron in familial amyotrophic lateral sclerosis (Bruijn, L. I., et al., *Neuron* 18: 327–338 (1997)).

Since $Aβ_{1-42}$ appears to be more of an avid scavenger for superoxide than $Aβ_{1-40}$, we predict that the release of a greater proportion of $Aβ_{1-42}$ may reflect a physiological response to a more severe oxidation stress, e.g., apoptosis. The fact that greater amounts of reduced metal and ROS are generated by $Aβ_{1-42}$ than by $Aβ_{1-40}$, when binding Cu(II), reflects the higher binding affinity that $Aβ_{1-42}$ has for Cu(II) (11). Interestingly, familial AD mutations in the presenilins have been associated with both apoptosis and increased $Aβ_{1-42}$ release (Wolozin, B., et al., *Science* 274: 1710–1713 (1996)). This raises the intriguing possibility that increased $Aβ_{1-42}$ generation, e.g., owing to presenilin mutations, is a survival response with, perhaps, deleterious long-term consequences (a possible instance of molecular antagonistic pleiotropy). However, both species of Aβ have the ability to mimic SOD1 as described in Example 3.

Aβ joins SOD1 (Bruijn, L. I., et al., *Neuron* 18(2):327–38 (1997)) and PrP (Brown, D., et al., *Proceedings of International Society for Neurochemistry, Annual Meeting*, Berlin 1999; Brown, D. R., et al., *Biochem. J.* 344: 1–5 (1999)) as copper-binding proteins with superoxide dismutase activities that accumulate in association with a neurodegenerative disease. The homeostasis of Cu and Zn is disregulated in the AD brain (Huang, X., et al., *J. Biol. Chem.* 272:26464–26470 (1997); Atwood, C. S., et al., *Journal of Biological Chemistry* 273:12817–12826 (1998)), and levels of Cu and Zn are markedly elevated in the AD brain parenchyma (Lovell, M. A., et al., *J. Neurol. Sci.* 158(1): 47–52 (1998)). Since the dismutase activity of Aβ is conditioned by Cu and Zn, the abnormal homeostasis of Cu or Zn may impact upon both the function and the aggregation of Aβ (Bush, A. I., et al., *J. Biol. Chem.* 269:12152–12158 (1994); Bush, A. I., et al., *Science* 265:1464–1467 (1994); Huang, X., et al., *J. Biol. Chem.* 272:26464–26470 (1997); Atwood, C. S., et al., *Journal of Biological Chemistry* 273:12817–12826 (1998)) in AD.

Metal Ions and Aβ Deposition

The brain contains high levels of both Zn(II) (approximately 150 μM; Frederickson, C. J. *International Review of Neurobiology* 31:145–237 (1989)) and Cu(II) (approximately 100 μM; Warren, P. J., et al., *Brain* 83:709–717 (1960); Owen, C. A., *Physiological Aspects of Copper*, Noyes Publications, Park Ridge, N.J. (1982), pp. 160–191). Intracellular concentrations of Zn(II) and Cu(II) are approximately 1000 and 100 fold higher, respectively, than extracellular concentrations. This large gradient between intracellular and extracellular concentrations suggests that a highly energy dependent mechanism is required in order to sequester these metals within neurons. Therefore, alterations in energy metabolism or injuries, may affect the uptake of these metal ions, promote their release into the extracellular space and, together with the synergistic effects of decreased pH, induce membrane bound Aβ to aggregate.

Aβ binds copper and zinc at equimolar concentrations simultaneously. However, the affinity of $A\beta_{1-42}$ for Cu(II) is much greater ($2.0\times10^{-17}$ M) than the affinity of $A\beta_{1-40}$ for Cu(II) ($1.5-2.0\times10^{-10}$ M), while the peptides' affinities for Zn(II) are similar (Atwood, C. S., et al., *Soc. Neurosci. Abstr.* 23: 1883 (1997); unpublished observations). The fact that Aβ has such a high affinity for copper and zinc ions suggests that it has evolved to respond to slight changes in the concentration of extracellular metal ions. This is supported by the fact that aggregation in the presence of Cu is approximately 30% at pH 7.1, the pH of the brain (Yates C. M., et al., *J. Neurochem.* 55:1624–1630 (1990)), but 85% at pH 6.8. Taken together, the results indicate that Aβ may have evolved to respond to biochemical changes associated with neuronal damage as part of the locally mediated response to inflammation or cell injury. Thus, it is possible that Cu(II)-mediated Aβ binding and aggregation might be an intentional cellular response to a mildly acidic environment.

In addition, decreased cerebral pH is a complication of aging (Yates CM, et al., *J. Neurochem.* 55:1624–1630 (1990)) which further indicates that Cu- and Zn-mediated Aβ aggregation may be a normal cellular response to an environment of mild acidosis. However, prolonged exposure of Aβ to an environment of lower cerebral pH may promote increased concentrations of free metal ions and reactive oxygen species, and the inappropriate action of $A\beta_{1-42}$ over time promoting the formation of irreversible Aβ oligomers and their subsequent deposition as amyloid in AD. The reversibility of this pH-mediated Cu(II) aggregation does, however, present the potential for therapeutic intervention.

The discovery that Aβ can generate $H_2O_2$ and Cu(I), both of which are associated with neurotoxic effects, offers an explanation for the neurotoxicity of Aβ polymers. These findings suggest that it may be possible to reduce the neurotoxicity of Aβ polymers by controlling factors which alter the concentrations of Cu(I) and ROS generated by accumulated soluble Aβ. It has been discovered that manipulation of factors such as zinc, copper, and pH can result in altered Cu(I) and $H_2O_2$ production by Aβ. Therefore, agents identified as being useful for the adjustment of the pH and levels of zinc and copper in the brain interstitium can be used to adjust the concentration of Cu(I) and $H_2O_2$, and can therefore be used to reduce the neurotoxic burden and thus, to treat Alzheimer's disease.

Screening Assays for Identifying Agents Used to Treat Alzheimer's Disease

To summarize, it has recently been discovered that (i) much of the Aβ aggregation in AD-affected brains is held together by zinc and copper, (ii) Aβ peptides exhibit Fe/Cu-dependent redox activity similar to that of SOD1, (iii) $A\beta_{1-42}$ is especially redox reactive and has the unusual property of reducing $O_2$ to $H_2O_2$, (iv) deregulation of Aβ redox reactivity causes the peptide to polymerize, and (v) Aβ has beneficial antioxidant properties. Since these reactions are implicated in the pathogenetic events of AD, they offer promising targets for therapeutic drug design. Therefore, agents useful in the treatment and/or prevention of AD and/or symptoms thereof include:

(a) agents that reduce the amount of Cu(I) or Fe(II) produced by Aβ;

(b) agents that promote or inhibit the production of hydrogen peroxide by Aβ;

(c) agents that inhibit the production of OH.; and/or (d) agents that do not inhibit the ability of Aβ to function as an anti-oxidant.

Since aggregation and crosslinking of Aβ contribute to its neurotoxicity, agents identified as having at least one of the activities listed above may also be subjected to tests to determine if the agent is capable of inhibiting oligomerization by Aβ. Such agents may also be tested for their ability to reduce the neurotoxicity of both soluble and crosslinked Aβ.

Because the ability of Aβ to generate $H_2O_2$ from $O_2^-$ may, in many instances, be beneficial, the invention relates to a method for identifying an agent that does not inhibit this process to be used in the treatment and/or prevention of AD and/or symptoms thereof. Thus, in one aspect of the invention, a method for identifying an agent comprises two steps. In the first step, the ability of the candidate agent to prevent dissolved oxygen-dependent hydrogen peroxide formation and subsequent ROS production is assessed. If the agent can shut down the "pro-oxidant" activity, then the agent is subjected to the second step wherein the ability of the agent not to inhibit the antioxidant, i.e., SOD-like, activity of Aβ is assessed. If the agent does not inhibit such antioxidant activity, then that agent may be useful in the treatment and/or prevention of AD and/or symptoms thereof.

Thus, the method comprises:

(a) adding an agent to an Aβ-containing sample;

(b) determining whether the agent is capable of inhibiting dissolved oxygen-dependent hydrogen peroxide formation; and (c) determining whether the agent is capable of not inhibiting the superoxide-dependent hydrogen peroxide formation.

In a preferred embodiment, the determination of the ability of the agent to alter the SOD-like activity of Aβ is made by determining whether Aβ is capable of catalytically producing Cu(I), Fe(II) or $H_2O_2$. Methods, besides those which are disclosed elsewhere in this application, for determining if Aβ is capable of catalytically producing Cu(I), Fe(II) or $H_2O_2$ are well known to those of ordinary skill in the art. In particular, the catalytic production of $H_2O_2$ may be determined by using laser flash photolysis, pulse radiolysis or the NBT assay (G. Peters and M. A. J. Rodgers, *Biochim. Biophys. Acta* 637: 43–52 (1981)).

In another aspect, the invention relates to a method for the identification of an agent to be used in the treatment and/or prevention of AD and/or symptoms thereof, wherein the agent is capable of altering, and preferably decreasing, the production of Cu(I) by Aβ, the method comprising:

(a) adding Cu(II) to a first Aβ sample;

(b) allowing the first sample to incubate for an amount of time sufficient to generate Cu(I);

(c) adding Cu(II) to a second Aβ sample, the second sample additionally comprising a candidate pharmacological agent;

(d) allowing the second sample to incubate for the same amount of time as the first sample;

(e) determining the amount of Cu(I) produced by the first and second samples; and (f) comparing the amount of Cu(I) produced by the first sample to the amount of Cu(I) produced by the second sample;

whereby a difference in the amount of Cu(I) produced by the first sample as compared to the second sample indicates that the candidate pharmacological agent has altered the production of Cu(I) by Aβ. Of course, where the amount of Cu(I) is lower in the second sample than in the first sample, this will indicate that the agent has decreased Cu(I) production.

In a preferred embodiment, the amount of Cu(I) present is determined by using a spectrophotometric method. For example, the amount of Cu(I) present in the first and second samples is determined by:
(a) adding a complexing agent to the first and second samples, wherein the complexing agent is capable of combining with Cu(I) to form a complex compound, wherein the complex compound has an optimal visible absorption wavelength;
(b) measuring the absorbencies of the first and second samples; and
(c) calculating the concentration of Cu(I)in the first and second samples using the absorbencies obtained in (b).

In a preferred embodiment, the complexing agent is bathocuproinedisulfonic (BC) anion. See Example 2. The concentration of Cu(I) produced by Aβ may then be calculated on the basis of the absorbencies of the samples from about 478 nm to about 488 nm, more preferably from about 480 to about 486 nm, and most preferably about 483 nm. Since Aβ will produce $H_2O_2$ and Cu(I) almost immediately following the addition of Cu(II) to the reaction mixture, BC may be added to the reaction immediately following the addition of Cu(II). The concentration of BC to be achieved in a sample is between about 10 $\mu$M and about 400 $\mu$M, more preferably between about 75 $\mu$M and about 300 $\mu$M, and still more preferably between about 150 $\mu$M and about 275 $\mu$M. In the most preferred embodiment, the concentration of BC to be achieved in a sample is about 200 $\mu$M. Of course, one of ordinary skill in the art can readily optimize the concentration of BC to be added with no more than routine experimentation.

In a preferred embodiment, the above-described method may be performed in a microtiter plate, and the absorbency measurements performed by a plate reader, thus allowing large numbers of candidate pharmacological compounds to be tested simultaneously.

In another aspect, the invention relates to a method for the identification of an agent to be used in the treatment and/or prevention of AD and/or symptoms thereof, wherein the agent is capable of altering, and preferably decreasing, the production of Fe(II) by Aβ. The method comprises:
(a) adding Fe(III) to a first Aβ sample;
(b) allowing the first sample to incubate for an amount of time sufficient to generate Fe(II);
(c) adding Fe(III) to a second Aβ sample, the second sample additionally comprising a candidate pharmacological agent;
(d) allowing the second sample to incubate for the same amount of time as the first sample;
(e) determining the amount of Fe(II) produced by the first and second samples; and
(f) comparing the amount of Fe(II) present in the first sample to the amount of Fe(II) present in the second sample;
whereby a difference in the amount of Fe(II) present in the first sample as compared to the second sample indicates that the candidate pharmacological agent has altered the production of Fe(II) by Aβ. Of course, where the amount of Fe(II) is lower in the second sample than in the first sample, this will indicate that the agent has decreased Fe(II) production.

Fe(II) may be determined using the spectrophotometric method of Linert et al., *Biochim. Biophys. Acta* 1316:160–168 (1996). Other such methods will be readily apparent to those of ordinary skill in the art.

In a preferred embodiment, the amount of Fe(II) present is determined by using a spectrophotometric method analogous to that used for the determination of Cu(I), above. The preferred complexing agent is batho-phenanthrolinedisulfonic (BP) anion. The concentration of Fe(II)-BP produced by Aβ may then be calculated on the basis of the absorbencies of the samples from about 530 to about 540 nm, more preferably from about 533 nm to about 538 nm, and most preferably at about 535 nm. See Example 2. Since Aβ will produce $H_2O_2$ and Fe(II) almost immediately following the addition of Fe(III) to the reaction mixture, BP may be added to the reaction immediately following the addition of Fe(III). The concentration of BP to be achieved in a sample is between about 10 $\mu$M and about 400 $\mu$M, more preferably between about 75 $\mu$M and about 300 $\mu$M, and still more preferably between about 150 $\mu$M and about 275 $\mu$M. In the most preferred embodiment, the concentration of BP to be achieved in a sample is about 200 $\mu$M. Of course, one of ordinary skill in the art can readily optimize the concentration of BP to be added with no more than routine experimentation.

In a preferred embodiment, the above-described method may be performed in a microtiter plate, and the absorbency measurements performed by a plate reader, thus allowing large numbers of candidate pharmacological compounds to be tested simultaneously.

In yet another aspect, the invention relates to a method for the identification of an agent to be used in the treatment and/or prevention of AD and/or symptoms thereof, wherein the agent is capable of altering the production of $H_2O_2$ by Aβ, the method comprising:
(a) adding Cu(II) or Fe(III) to a first Aβ sample;
(b) allowing the first sample to incubate for an amount of time sufficient to generate $H_2O_2$;
(c) adding Cu(II) or Fe(III) to a second Aβ sample, the second sample additionally comprising a candidate pharmacological agent;
(d) allowing the second sample to incubate for the same amount of time as the first sample;
(e) determining the amount of $H_2O_2$ produced by the first and second samples; and
(f) comparing the amount of $H_2O_2$ present in the first sample to the amount of $H_2O_2$ present in the second sample;
whereby a difference in the amount of $H_2O_2$ present in the first sample as compared to the second sample indicates that the candidate pharmacological agent has altered the production of $H_2O_2$ by Aβ. As will be understood by one of ordinary skill in the art, this method may be used to detect agents which decrease the amount of $H_2O_2$ produced (in which case the amount of $H_2O_2$ will be lower in the second sample than in the first sample).

The amount of $H_2O_2$ produced may be determined using, for example, the PeroXOquant Quantitative Peroxide Assay (Pierce, Rockford, Ill.).

In a preferred embodiment, the determination of the amount of $H_2O_2$ present in the first and second samples is determined by a method comprising:
(a) adding catalase to a first aliquot of the first sample in an amount sufficient to break down the $H_2O_2$ generated by the sample;
(b) adding TCEP to
(i) a first aliquot of the first sample; <(ii) a second aliquot of the first sample; and
(iii) the second sample;

(c) incubating the samples obtained in (b) for an amount of time sufficient to allow the TCEP to capture all of the $H_2O_2$;

(d) adding DTNB to the samples obtained in (c);

(e) incubating the samples obtained in (d) for an amount of time sufficient to generate TMB;

(f) measuring the absorbencies of the samples obtained in (e); and (g) calculating the concentration of $H_2O_2$ in the first and second samples using the absorbencies obtained in (f).

In a preferred embodiment, the absorbency of TMB is measured from about 407 to about 417 nm. In a more preferred embodiment, the absorbency is measured at about 412 nm.

In a preferred embodiment, the above-described method is performed in a microtiter plate, and the absorbency measurements are performed by a plate reader, thus making it possible to screen large numbers of candidate pharmacological agents simultaneously.

In another aspect, the invention relates to a method for the identification of an agent to be used in the treatment and/or prevention of AD and/or symptoms thereof, wherein the agent is capable of inhibiting redox-reactive metal-mediated crosslinking Aβ, the method comprising:

(a) adding a redox-reactive metal to a first Aβ sample;

(b) allowing the first sample to incubate for an amount of time sufficient to allow Aβ crosslinking;

(c) adding the redox-reactive metal to a second AD sample, the second sample additionally comprising a candidate pharmacological agent;

(d) allowing the second sample to incubate for the same amount of time as the first sample;

(e) removing an aliquot from each of the first and second samples; and (f) determining presence or absence of crosslinking in the first and second samples, whereby an absence of Aβ crosslinking in the second sample as compared to the first sample indicates that the candidate pharmacological agent has inhibited Aβ crosslinking.

In a preferred embodiment, at (f), a western blot analysis is performed to determine the presence or absence of crosslinking in the first and second samples.

The six assays described above may be practiced in any order and combination to effectively identify agents useful in the treatment and/or prevention of AD and/or symptoms thereof.

In another aspect, candidate pharmacological agents which have been identified by one or more of the above screening assays can undergo further screening to determine if the agents are capable of altering, and preferably reducing or eliminating, Aβ-mediated toxicity in cell culture. Such assays include, but are not limited to, the MTT assay, which measures the reduction of 3-(4,5-dimethylthiazol-2-yl)-2,5, diphenyl tetrazolium bromide (MTT) to a colored formnazon (Hansen et al., 1989). Although alternatives have not been ruled out (Burdon et al., 1993), the major site of MTT reduction is thought to be at two stages of electron transport, the cytochrome oxidase and ubiquinone of mitochondria (Slater et al., 1963).

An alternative assay measures the release of lactic dehydrogenase (LDH) from cells, a measurement routinely used to quantitate cytotoxicity in cultured CNS cells (Choi, 1987). While MTT measures primarily early redox changes within the cell reflecting the integrity of the electron transport chain, the release of LDH is thought to be through cell lysis. A third assay is directed to visual counting in conjunction with trypan blue exclusion. Other commercially available assays for neurotoxicity, including the Live/Dead Euko Light Viability/Cytotoxicity Assay (Molecular Probes, Inc. Eugene, Oreg.) may also be used to determine if a candidate compound which alters Cu(I), Fe(II), $H_2O_2$, OH. and $O_2^-$ production or alters copper-induced, pH-dependent aggregation and crosslinking of Aβ, is also capable of reducing the neurotoxicity of Aβ. Cells types which may be used in the neurotoxicity assays include, but are not limited to, cancer cells and primary cells, such as rat primary frontal neuronal cells.

Thus, the invention further relates to a method for identifying an agent to be used in the treatment and/or prevention of AD and/or symptoms thereof, wherein the agent is capable of reducing the toxicity of Aβ, the method comprising:

(a) adding AD to a first cell culture;

(b) adding Aβ to a second cell culture, the second cell culture additionally containing a candidate pharmacological agent;

(c) determining the level of neurotoxicity of Aβ in the first and second samples; and (d) comparing the level of neurotoxicity of Aβ in the first sample to the level of neurotoxicity of Aβ in the second sample;

whereby a lower neurotoxicity level in the second sample as compared to the first sample indicates that the candidate pharmacological agent has reduced the neurotoxicity of Aβ, and is thereby capable of being used to treat and/or prevent AD and/or symptoms thereof.

Candidate pharmacological agents to be tested in any of the above-described methods will be broad-ranging. Such agents include, but are not limited to, agents which modify the availability of zinc or copper for interaction with Aβ such as chelating agents, such as desferrioxamine, and amino acids such as histidine and cysteine which bind free zinc and are thought to be involved in bringing zinc from plasma across the blood-brain barrier (BBB). These agents include, but are not limited to, all classes of specific zinc chelating agents, and combinations of non-specific chelating agents capable of chelating zinc such as EDTA (edetic acid, N,N'-1,2-ethane diylbis(N-(carboxymethyl)glycine) or (ethylenedinitrilo)tetraacetic acid, entry 3490 in *The Merck Index*, 10th edition) and all salts of EDTA, and/or phytic acid (myo-Inositol hexakis(dihydrogen phosphate), entry 7269 in *The Merck Index*, 10th edition) and phytate salts. Preferred candidate agents within this class include bathocuproine and bathophenanthroline. Additional agents include, but are not limited to, compounds which may have access to the brain such as dye compounds, heparin, heparan sulfate, and antioxidants, e.g., ascorbate, trolox and tocopherols.

The pH of the various reaction mixtures is preferably close to neutral. The pH, therefore, may range from about 6.6 to about 8, preferably from about 6.6 to about 7.8. The most preferred pH is about 7.4.

The present invention may be practiced at a temperature ranging from about 25° C. to about 40° C. The preferred temperature range is from about 30° C. to about 40° C. The most preferred temperature for the practice of the present invention is about 37° C., i.e., human body temperature.

Buffers which may be used in the methods of the invention include, but are not limited to, PBS, Tris-chloride and Tris-base, MOPS, HEPES, bicarbonate, Krebs and Tyrode's. The concentration of the buffer is between about 10 mM and about 500 mM. Because of the nature of the assays which are included in the methods of the invention, when choosing a buffer, it must be borne in mind that spontaneous free radical production within a given buffer might interfere with the reactions. For this reason, PBS is the preferred buffer for use in the methods of the invention, although other buffers may be used provided that proper controls are used to correct for the above-mentioned potential free radical formation.

Cu(II) must be present in the reaction mixture for Aβ to produce Cu(I). Any salt of Cu(II) may be used to satisfy this requirement, including, but not limited to, $CuCl_2$, $Cu(NO_3)_2$, etc. Concentrations of copper range from at least about 1 μM to about 50 μM. Preferably, a copper concentration of about 10 μM is included in the reaction mixture.

Fe(III) must be present in the reaction mixture for Aβ to produce Fe(II). Any salt of Fe(III) may be used to satisfy this requirement, including, but not limited to, $FeCl_3$, etc. Concentrations of iron range from at least about 1 μM to about 50 μM. Preferably, an iron concentration of about 10 μM is included in the reaction mixture.

A redox active metal such as Cu(II) or Fe(III) must be present in the reaction mixture for Aβ to catalytically produce $H_2O_2$. Any salt of Cu(II) may be used to satisfy this requirement, including, but not limited to, $CuCl_2$, $Cu(NO_3)_2$, etc. Similarly, any salt of Fe(III) may be used in accordance with the invention, such as $FeCl_3$. Concentrations of copper or iron range from at least about 1 μM to about 50 μM. Preferably, a copper or iron concentration of about 10 μM is included in the reaction mixture.

The production of Cu(I) and $H_2O_2$ by Aβ occurs at near-instantaneous rate. Hence, the measurement of the concentration of Cu(I) or $H_2O_2$ produced may be performed substantially immediately after the addition of Cu(II) to Aβ.

Similarly, Aβ will produce $H_2O_2$ and Fe(II) almost immediately following the addition of Fe(III) and, optionally, Zn(II) to the reaction mixture. Hence, the measurement of the concentration of Fe(II) or $H_2O_2$ produced may be performed substantially immediately after the addition of Fe(III) to Aβ. However, if desired, the reaction may be allowed to proceed longer. In an alternative embodiment of the invention, the reaction is carried out for about 30 minutes.

The invention may also be carried out in the presence of biological fluids, such as the biological fluid, CSF, to closely simulate actual physiological conditions. Of course, such fluids will already contain Aβ, thus where the methods of the invention are to be carried out using a biological fluid such as CSF, it is not necessary to add Aβ to the samples. The biological fluid may be used directly or diluted from about 1:1,000 to about 1:5 fold.

Each of the assays of the present invention is ideally suited for the preparation of a kit. Such a kit may comprise a carrier means being compartmentalized to receive in close confinement therein one or more container means, such as vials, tubes and the like, each of the container means comprising one of the separate elements of the assay to be used in the method. For example, there may be provided a container means containing a standard solution of the Aβ peptide or lyophilized Aβ peptide and a container means containing a standard solution or varying amounts of a salt of a redox active metal, such as Cu(II) or Fe(III), in any form, i.e., in solution or dried, soluble or insoluble, in addition to further carrier means containing varying concentrations of reagents used in the present methods. For example, solutions to be used for the determination of Cu(I) or Fe(II) as described in Example 2 may include BC anion and BP anion, respectively. Similarly, solutions to be used for the determination of $H_2O_2$ as described in Example 2 may include TCEP and DTNB, as well as catalase (about 10 U/ml). Standard solutions of Aβ peptide preferably have concentrations above about 10 μM, more preferably from about 10 to about 25 μM, or, if the peptide is provided in its lyophilized form, may be provided in an amount which can be solubilized to these concentrations by adding an aqueous buffer or physiological solution thereto. Standard solutions of analytes may be used to prepare control mixtures and test reaction mixtures for comparison according to the methods of the present invention.

Treatment of Alzheimer's Disease and/or Symptoms Thereof

The agent(s) identified by any one or a combination of the above-described screening assays may be administered by any route that delivers efficacious levels of the agent, e.g., by injection, infusion, orally, intranasally, parenterally, intravenously, subcutaneously, intramuscularly, intraperitoneally, rectally, by implantation, transdermally, by slow release, intrabuccally, or intracerebrally to reduce the degree and severity of AD and/or symptoms thereof. In other words, the agent will be administered in a therapeutically effective amount using any suitable physical method. For parenteral administration, preparations containing the agent may be provided to a patient in need of such treatment in combination with a physiologically acceptable carrier, such as salt or buffer or pharmaceutically acceptable sterile aqueous or non-aqueous solvents, suspensions, dispersion media or emulsions. Examples of non-aqueous solvents are propylene glycol, polyethylene glycol, vegetable oil such as olive oil, and injectable organic esters such as ethyl oleate. Aqueous carriers include water, physiological saline, water-alcohol solutions, Ringer's dextrose solution, dextrose plus sodium chloride solution, Ringer's solution containing lactose, and fixed oils. Other ingredients that may be included are those that improve the efficacy of the composition. Carriers or occlusive dressings can be used to increase skin permeability and enhance antigen absorption. Examples of materials suitable for use in preparing pharmaceutical compositions are provided in numerous sources including *Remington's Pharmaceutical Sciences*, Osol, A., ed., 18th Edition, 1990, Mack Publishing Co., Easton, Pa.

For injections, sterile aqueous solutions (where water soluble) are generally used or, alternatively, sterile powders for the extemporaneous preparation of sterile injectable solutions may be used. The pharmaceutical compositions must be stable under the conditions of manufacture and storage and must be preserved against the contaminating action of microorganisms such as bacteria and fungi. Preventing the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the agent in the required amount in the appropriate solvent with various of the other ingredients enumerated above, as required, followed by sterilization by, for example, filtration or irradiation.

In the case of sterile powders for the preparation of sterile injectable solutions, the preferred methods of preparation are vacuum drying and the freeze-drying technique which yield a powder of the active agent plus any additional desired ingredient from previously sterile-filtered solution(s) thereof.

When the active agents are suitably protected they may be orally administered, for example, with an inert diluent or with an assimilable edible carrier, or they may be enclosed in a hard or soft shell gelatin capsule, compressed into tablets, or incorporated directly with food in the diet. For oral therapeutic administration, the active agent may be incorporated with excipients and used in the form of ingestible tablets, buccal tablets, troches, capsules, elixirs, suspensions, syrups, wafers, and the like. Such compositions and preparations should contain at least about 1% by weight of the agent identified by the screening assay(s). The percentage of the compositions and preparations may, of course, be varied and may conveniently be between about 5 to about 80% of the weight of the unit. The active agent may be compounded for convenient and effective administration in effective amounts with a suitable pharmaceutically acceptable carrier in dosage unit form. The dosage will depend upon factors such as the patient's age, health and weight, the dosage form used, concurrent treatment, if any, desired effect, and the specific agent employed. Additional information related to dosages and the administration of drugs can be found in numerous sources including *Remington's Pharmaceutical Sciences*, Osol, A., ed., 18th Edition, 1990, Mack Publishing Co., Easton, Pa. The dosage of the various compositions can be modified by comparing the relative in vivo potencies of the drugs and the bioavailability using no more than routine experimentation.

Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active agent and the particular therapeutic effect to be achieved, and (b) the limitations inherent in the art of compounding such an active material for the treatment of disease in living subjects having a diseased condition in which bodily health is impaired as herein disclosed in detail.

The tablets, troches, pills, capsules and the like may also contain other components such as listed hereafter: a binder such as gum, acacia, corn starch or gelatin; an excipient such as dicalcium phosphate; a disintegrating agent such as corn starch, potato starch, alginic acid and the like; a lubricant such as magnesium stearate; and a sweetening agent such a sucrose, lactose or saccharin may be added and/or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active agent, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active agent may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or ingredient is incompatible with the active agent, use thereof in the therapeutic compositions is contemplated. Supplementary active agents can also be incorporated into the compositions.

The pharmaceutical compositions of the invention may be administered to any animal which may experience the beneficial effects of the agents identified by from the screening assay(s) of the invention. Foremost among such animals are mammals, e.g., humans, although the invention is not intended to be so limited.

The following examples are provided by way of illustration to further describe certain preferred embodiments of the invention and are not intended to be limiting of the present invention, unless so specified.

EXAMPLES

Example 1

Copper-Induced, pH-Dependent Aggregation of Aβ

Materials and Methods a) Preparation of Aβ Stock

Human $A\beta_{1-40}$ peptide was synthesized, purified and characterized by HPLC analysis, amino acid analysis and mass spectroscopy by the W. M. Keck Foundation Biotechnology Resource Laboratory (Yale University, New Haven, Conn.). Synthetic Aβ peptide solutions were dissolved in trifluoroethanol (30% in Milli-Q water (Millipore Corporation, Milford, Mass.)) or 20 mM HEPES (pH 8.5) at a concentration of 0.5–1.0 g/ml and centrifuged for 20 minutes at 10,000 g. The resulting supernatant (stock $A\beta_{1-40}$) was used for subsequent aggregation assays on the day of the experiment. The concentration of stock $A\beta_{1-40}$ was determined by UV spectroscopy at 214 nm or by Micro BCA protein assay (Pierce, Rockford, Ill.). The Micro BCA assay was performed by adding 10 µl of stock $A\beta_{1-40}$ (or bovine serum albumin standard) to 140 µl of distilled water, and then adding an equal volume of supernatant (150 µl) to a 96-well plate and measuring the absorbance at 562 nm. BSA is used as a standard for calibrating the assay. The concentration of $A\beta_{1-40}$ was determined from the BSA standard curve. Prior to use, all buffers and stock solutions of metal ions were filtered though a 0.22 µm filter (Gelan Sciences, Ann Arbor, Mich.) to remove any particulate matter. All metal ions were the chloride salt, except lead nitrate.

Aggregation Assays $A\beta_{1-40}$ stock was diluted to 2.5 µM in 150 mM NaCl and 20 mM glycine (pH 3–4.5), mes (pH 5–6.2) or HEPES (pH 6.4–8.8), with or without metal ions, incubated (30 minutes, 37° C.), and centrifuged (20 minutes, 10,000 g). The amount of protein in the supernatant was determined by the Micro BCA protein assay as described above.

c) Turbidometric Assays

Zn(II) mediated $A\beta_{1-40}$ aggregation is reversible whereas $A\beta_{1-40}$ aggregation induced by pH 5.5 is irreversible, thus experiments were performed to determine whether Cu(II)/pH-mediated $A\beta_{1-40}$ aggregation is reversible. Cu(II)-induced $A\beta_{1-40}$ aggregation at pH 7.4 is reversible following EDTA chelation, although for each new aggregation cycle, complete resolubilization of the aggregates required a longer incubation. This result suggests that a more complex aggregate is formed during each subsequent aggregation cycle, preventing the chelator access to the peptide to remove Cu(II). This is supported by the fact that complete resolubilization occurs with time, and Aβ is not adopting a structural conformation that is insensitive to Cu(II)-induced aggregation/EDTA-resolubilization.

To investigate the reversibility of Cu(II)-induced Aβ aggregation, 25 µM $A\beta_{1-40}$ and 25 µM Cu(II) were mixed in 67 mM phosphate buffer, 150 mM NaCl (pH 7.4) and turbidity measurements were taken at four 1 minute intervals. Subsequently, 20 μl aliquots of 10 mM EDTA or 10 mM Cu(II) were added to the wells alternatively, and, following a 2 minute delay, a further four readings were taken at 1 minute intervals. After the final EDTA addition and turbidity reading, the mixtures were incubated for an additional 30 minutes before taking final readings. Turbidity measurements were performed as described by Huang et al., J. Biol. Chem. (submitted), except $A\beta_{1-40}$ stock was brought to 10 μM (300 μl) in 20 mM HEPES buffer, 150 mM NaCl (pH 6.6, 6.8 or 7.4), with or without metal ions, prior to incubation (30 minutes, 37° C.).

The reversibility of pH potentiated Cu(II)-induced $A\beta_{1-40}$ aggregation was studied by turbidometry using a pH range of 7.5 to 6.6 representing $H^+$ concentration extremes that might be found in vivo (FIGS. 5A and 5B). 10 μM $A\beta_{1-40}$ and 30 μM Cu(II) were mixed in 67 mM phosphate buffer, 150 mM NaCl (pH 7.4) and an initial turbidity measurement taken. Subsequently, the pH of the solution was successively decreased to 6.6 and then increased back to 7.4. The pH of the reaction was monitored with a microprobe (Lazar Research Laboratories Inc., Los Angeles, Calif.) and the turbidity read at 5 minute intervals for up to 30 minutes. This cycle was repeated three times.

Figure 5A:
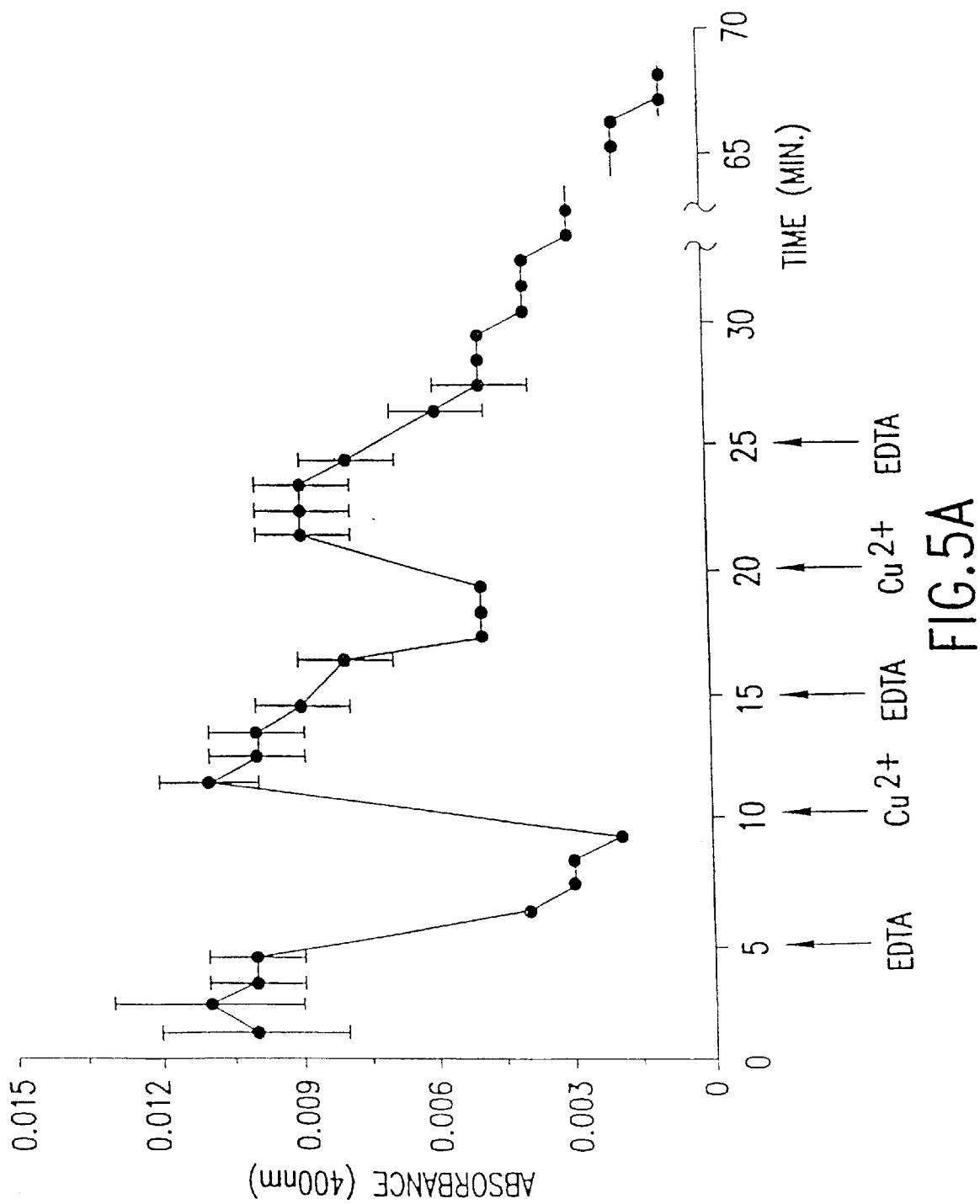
FIGS. 5A and 5B.
Figure 5B:
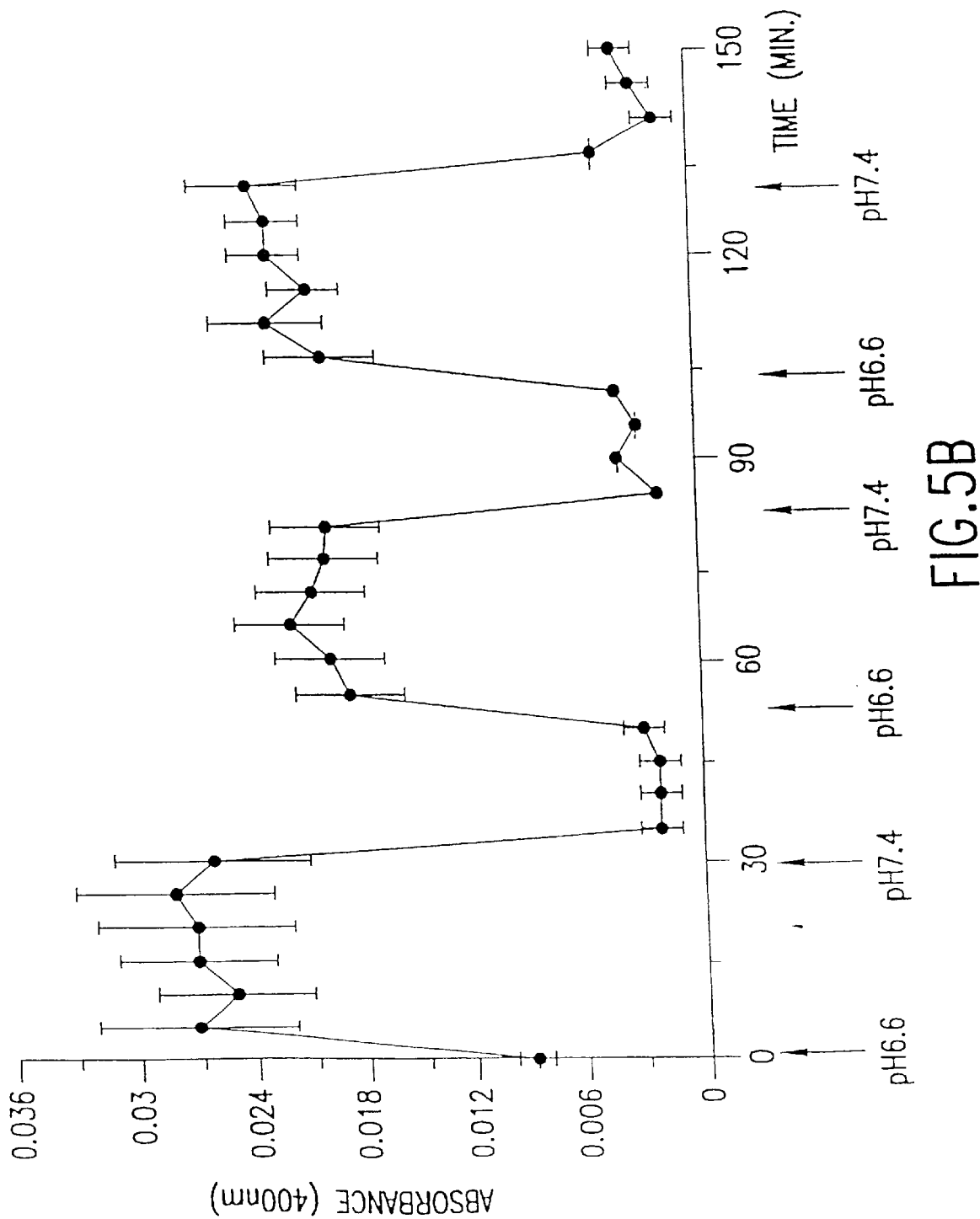

Unlike the irreversible aggregation of $A\beta_{1-40}$ observed at pH 5.5, Cu(II)-induced $A\beta_{1-40}$ aggregation was fully reversible as the pH oscillated between pH 7.4 and 6.6. FIG. 5A shows the turbidometric analysis of Cu(II)-induced $A\beta_{1-40}$ aggregation at pH 7.4 reversed by successive cycles of chelator (EDTA). FIG. 5B shows turbidometric analysis of the reversibility of Cu(II)-induced $A\beta_{1-40}$ as the pH cycles between 7.4 and 6.6. Thus, subtle conformational changes within the peptide, induced by changing $[H^+]$ within a narrow pH window (corresponding to physiologically plausible $[H^+]$), allow the aggregation or resolubilization of the peptide in the presence of Cu(II). The present data suggest that Cu(II)-binding and aggregation of Aβ will occur when the pH of the microenvironment rises. This conclusion can be based on the finding that the reaction is $[H^+]$- and Cu(II)-dependent and reversible within a narrow, physiologically plausible, pH window. This is further supported by the specificity and high affinity of Cu(II) binding under mildly acidic conditions compared to the constant Zn(II)-induced aggregation (and binding) of $A\beta_{1-40}$ over a wide pH range (6.2–8.5) (Bush, A. I., et al., J. Biol. Chem. 269:12152 (1994)).

d) Immunofiltration Detection of Low Concentrations of $A\beta_{1-40}$ Aggregate Physiological concentrations of $A\beta_{1-40}$ (8 nm) were added to 150 mM NaCl, 20 mM HEPES (pH 6.6 or 7.4), 100 nm BSA with $CuCl_2$ (0, 0.1, 0.2. 0.5 and 2 μM) and incubated (30 minutes, 37° C.). The reaction mixtures (200 μl) were then placed into a 96-well Easy-Titer® ELIFA® system (Pierce, Rockford, Ill.) and filtered through a 0.22 μm cellulose acetate filter (MSI, Westboro, Mass.). Aggregated particles were fixed to the membrane (0.1% glutaraldehyde, 15 minutes), washed thoroughly and then probed with the anti-Aβ mAB 6E10 (Senetek, Maryland Heights, Mich.). Blots were washed and exposed to film in the presence of ECL chemiluminescence reagents (Amersham, Buckinghamshire, England). Immunoreactivity was quantified by transmittance analysis of ECL film from the immunoblots.

e) Aβ Metal-capture ELISA

Figure 3:
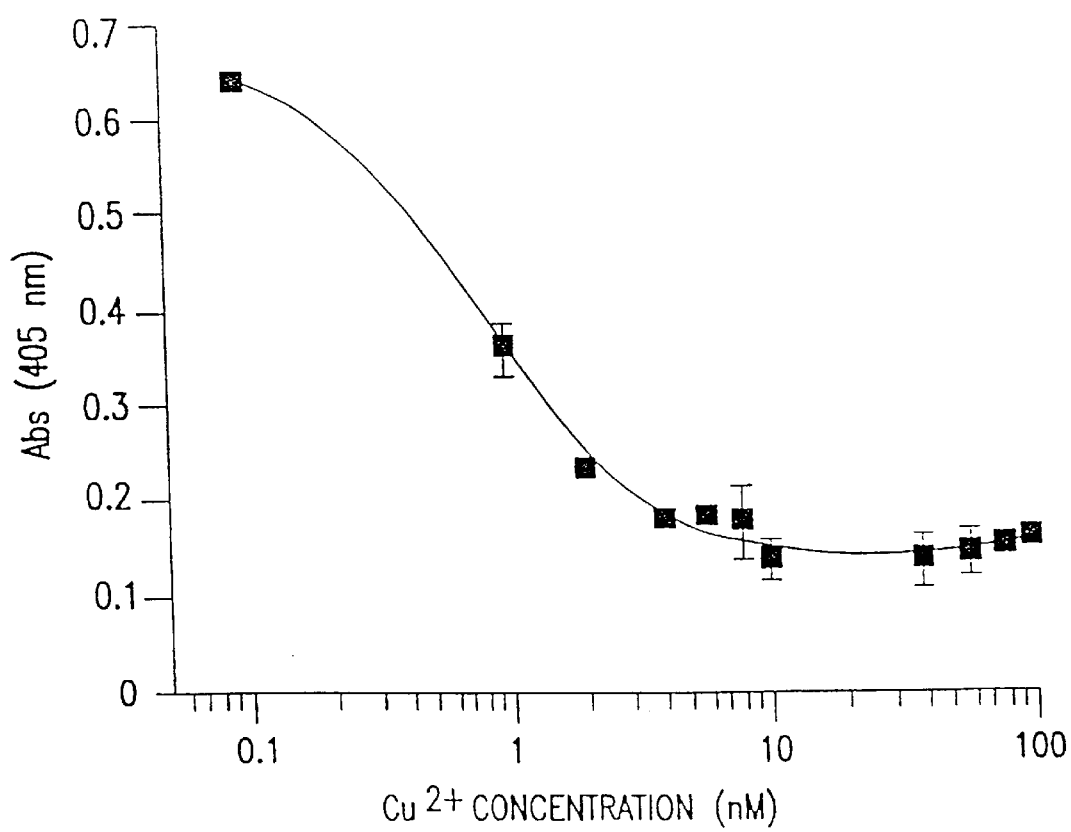
FIG. 3 is a graph showing a competition analysis of $Aβ_{1-40}$ binding to Cu(II).

Since $^{64}Cu$ is impractically short-lived (t1/2=13 hours), a metal-capture ELISA assay was used to perform competition analysis of $A\beta_{1-40}$ binding to a microtiter plate impregnated with Cu(II). $A\beta_{1-40}$ (1.5 ng/well) was incubated (2 hours, 37° C.) in the wells of Cu(II) coated microtiter plates (Xenopore, Hawthorne, N.J.) with increasing concentrations of Cu(II) (1–100 nm) as described by Moir et al., J. Biol. Chem. (submitted). Remaining ligand binding sites on well surfaces were blocked with 2% gelatin in tris-buffered saline (TBS) (3 hours, 37° C.) prior to overnight incubation at room temperature with the anti-Aβ mAb 6E10 (Senetek, Maryland Heights, Mich.). Anti-mouse IgG coupled to horseradish peroxidase was then added to each well and incubated for 3 hours at 37° C. Bound antibodies were detected by a 30 minute incubation with stable peroxidase substrate buffer/3,3',5,5'-tetramethyl benzidine (SPSB/TMB) buffer, followed by the addition of 2 M sulfuric acid. The increase in absorbance was measured at 450 nm. Results are shown in FIG. 3. All assays were performed in triplicate and have means±SD, n=3.

Competition analysis revealed that $A\beta_{1-40}$ has at least one high affinity, saturable Cu(II) binding site with a Kd=900 pM at pH 7.4 (FIG. 3). Since Cu(II) does not decrease Zn(II)-induced aggregation (Bush, A. I., et al., J. Biol. Chem. 269:12152 (1994)), indicating Cu(II) does not displace bound Zn(II), there are likely to be two separate metal binding sites. This is supported by the fact that there is both a pH sensitive and insensitive interaction with different metal ions as described above in section"c" and below in section "h."

f) Extraction of Aβ from Post-mortem Brain Tissue

Figure 8:
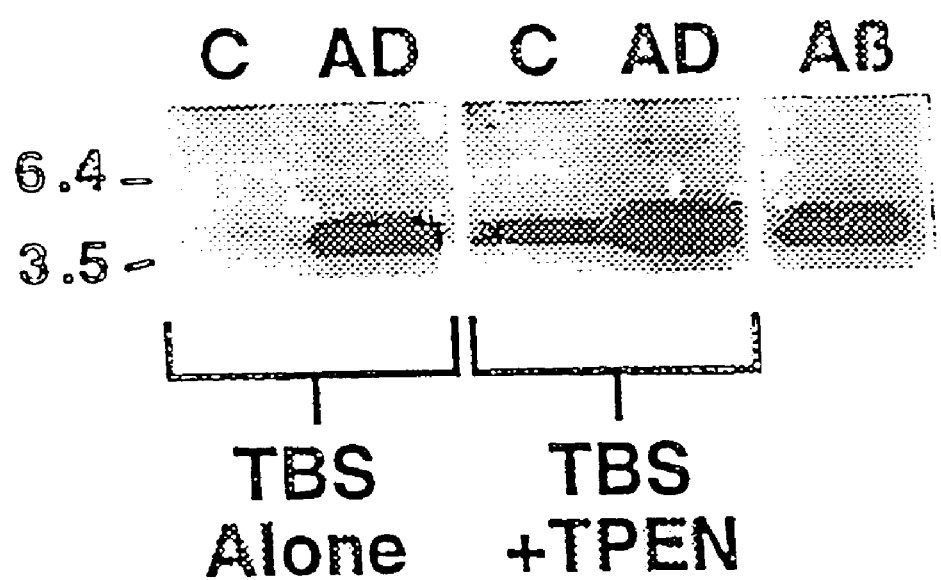
FIG. 8 is a western blot showing the extraction of Aβ from post-mortem brain tissue.

Identical regions of frontal cortex (0.5 g) from post-mortem brains of individuals with AD, as well as non-AD conditions, were homogenized in TBS, pH 4.7, with and without metal chelators. The homogenate was centrifuged and samples of the soluble supernatant as well as the pellet were extracted into SDS sample buffer and assayed for Aβ content by western blotting using the monoclonal antibody (mAb) WO2. The data shows a typical result comparing the amount of Aβ extracted into the supernatant phase in AD samples compared to control (young adult) samples (n=12 comparisons). N,N,N',N'-tetrakis(2-pyridyl-methyl) ethylenediamine (TPEN) (5 μM) allows the visualization of a population of pelletable Aβ that had not previously been recognized in unaffected brain samples (FIG. 8).

Roher and colleagues have recently shown that much of the Aβ that deposits in the AD-affected cortex can be solubilized in water (Roher, A. E, et al., J. Biol. Chem. 271:20631 (1996)). Supporting the clinical relevance of in vitro findings, it has recently been demonstrated that metal chelators increase the amount of Aβ extracted by Roher's technique (in neutral saline buffer) because the chelator employed has a high affinity for zinc or copper (FIG. 8). Hence, TPEN is highly efficient in extracting Aβ, as are TETA, and bathocuproine, whereas EGTA and EDTA are less efficient, requiring higher concentrations to achieve the same level of recovery. Zinc and copper ions (5–50 μM) added back to the extracting solution abolish the recovery of Aβ (which is subsequently extracted by the SDS sample buffer in the pellet fraction of the centrifuged brain homogenate suspension), but Ca(II) and Mg(II) added back to the chelator-mediated extracts of Aβ cannot abolish Aβ resolubilization from AD-affected tissue even when these metal ions are present in millimolar concentrations.

Importantly, atomic absorption spectrophotometry assays of the metal content of the chelator-mediated extracts confirm that Cu and Zn are co-released with Aβ by the chelators. These data strongly indicate that Aβ deposits (probably of the amorphous type) are held together by Cu and Zn and may also contain Fe. Interestingly, Aβ is not extractable from the control brain without the use of chelators. This suggests that metal-assembled Aβ deposits may be the earliest step in the evolution of Aβ plaque pathology.

g) Aβ Crosslinking by Copper

Figure 9:
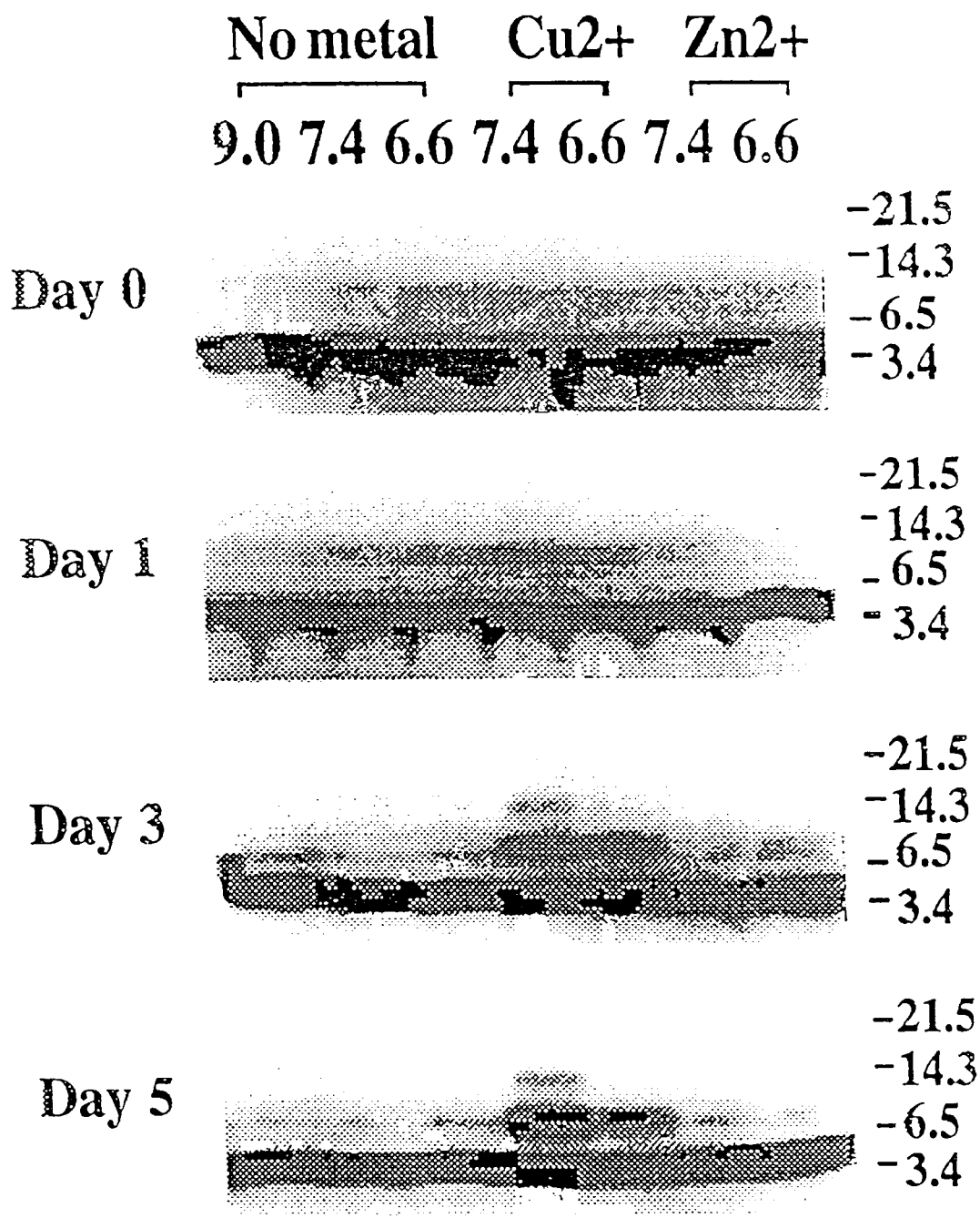
FIG. 9 is a western blot showing Aβ crosslinking by copper.
Figure 10:
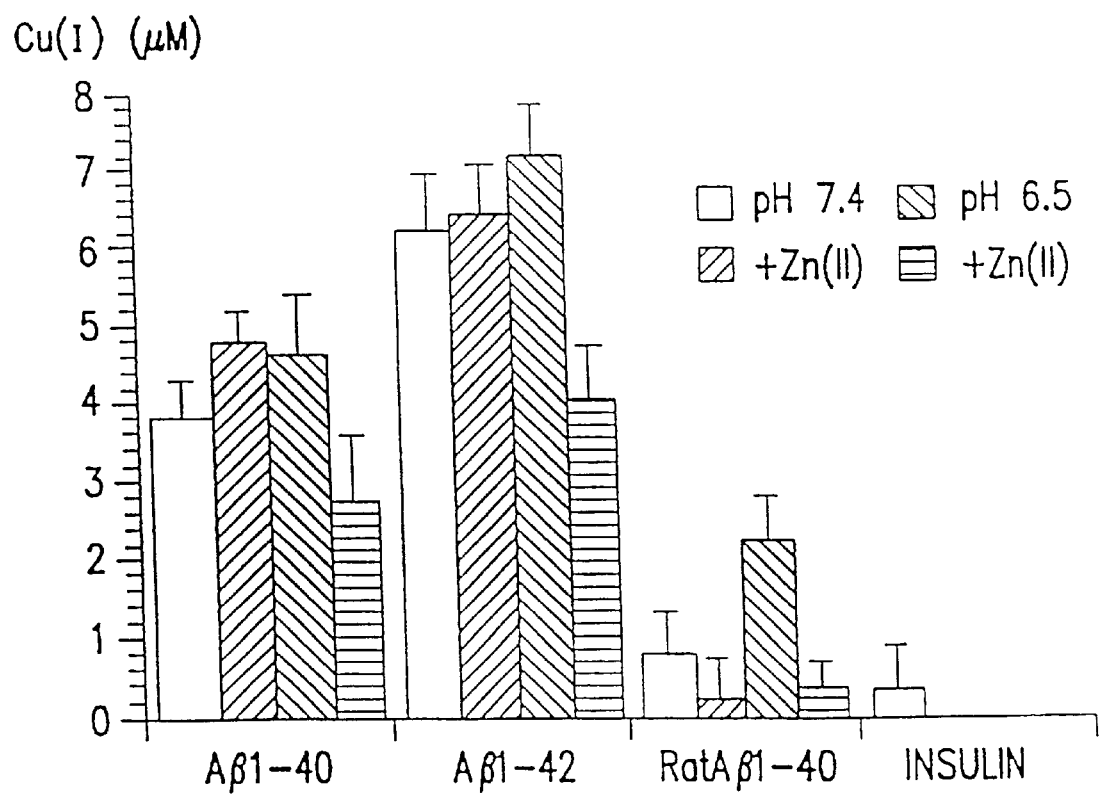
FIG. 10 is a graph showing Cu(I) generation by Aβ.

Cu(II)-induced SDS-resistant oligomerization of Aβ: $A\beta_{1-40}$ (2.5 μM), 150 mM NaCl and 20 mM HEPES (pH 6.6, 7.4 and 9), with or without $ZnCl_2$ or $CuCl_2$, were incubated at 37° C. for 30 minutes. Following incubation, aliquots of each reaction (2 ng peptide) were collected at day 0, 1, 3 and 5 and western blotted using the anti-Aβ monoclonal antibody 6F10. The dimer formed under these conditions has been found to be covalently linked. More specifically, Cu(II) (2–30 μM) has been found to induce covalent oligomerization of Aβ. Co-incubation with similar concentrations of Zn(II) accelerates the bridging, but zinc alone has no effect. The antioxidant sodium metabisulphite moderately attenuates the reaction, while ascorbic acid dramatically accelerates Aβ bridging. This suggests reduction of Cu(II) to Cu(I) with the latter mediating covalent bridging of Aβ. However, mannitol abolishes crosslinking, suggesting that the bridging is mediated by the generation of the hydroxyl radical by a Fenton reaction that recruits Cu(I) (FIG. 9). It should be noted that other means of visualizing and/or determining the presence or absence of crosslinking other than western blot analysis may be used. Such other means include, but are not limited to, density sedimentation by centrifugation.

The precipitating effects on Aβ by Zn(II) and Cu(II) were found to be qualitatively different. Zn-mediated aggregation is reversible with chelation and is not associated with neurotoxicity in primary neuronal cell cultures, whereas Cu-mediated aggregation is accompanied by the slow formation of covalently-bonded SDS-resistant dimers and by the induction of neurotoxicity. These neurotoxic SDS-resistant dimers are similar to those described by Roher, et al., *J. Biol. Chem.* 271:20631 (1996).

h) Biometal- and pH-dependent Aβ Aggregation

To accurately quantitate the effects of different metals and of pH on Aβ solubility, synthetic human $A\beta_{1-40}$ (2.5 μM) was incubated (37° C.) in the presence of metal ions at various pH for 30 minutes. The resultant aggregated particles were sedimented by centrifugation to permit determination of soluble $A\beta_{1-40}$ in the supernatant. To determine the centrifugation time required to completely sediment the aggregated particles generated under these conditions, $A\beta_{1-40}$ was incubated for 30 minutes at 37° C. with no metal, with Zn(II) (100 μM), with Cu(II) (100 μM) and at a pH of 5.5. Reaction mixtures were centrifuged at 10,000 g for different times, or ultracentrifuged at 100,000 g for 1 hour. FIG. 1 shows the proportion of soluble $A\beta_{1-40}$ remaining following centrifugation of reaction mixtures. All data points are means±SD, n=3.

Conformational changes within the N-terminal domain of Aβ are induced by modulating [H$^+$] (Soto, C., et al., *J. Neurochem.* 63:1191–1198 (1994)), and there is a metal (Zn(II)) binding domain in the same region, thus experiments were designed to determine whether there is a synergistic effect of pH on metal ion-induced Aβ aggregation. $A\beta_{1-40}$ was incubated with different bioessential metal ions at pH 6.6, 6.8 and 7.4, and subjected to centrifugation (20 minutes, 10,000 g). The results are shown in FIG. 2B, where "all metals" indicates incubation with a combination containing each metal ion at the nominated concentrations.

Figure 2A:
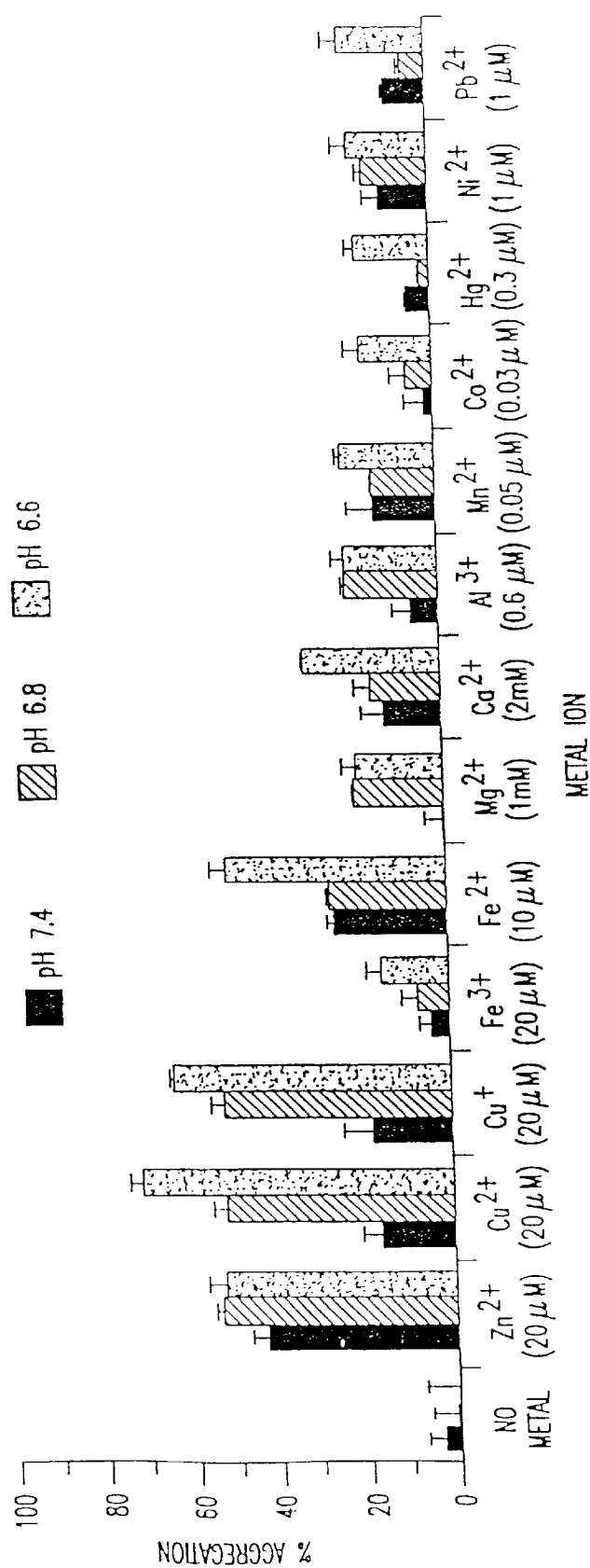
FIGS. 2A, 2B and 2C.
Figure 2B:
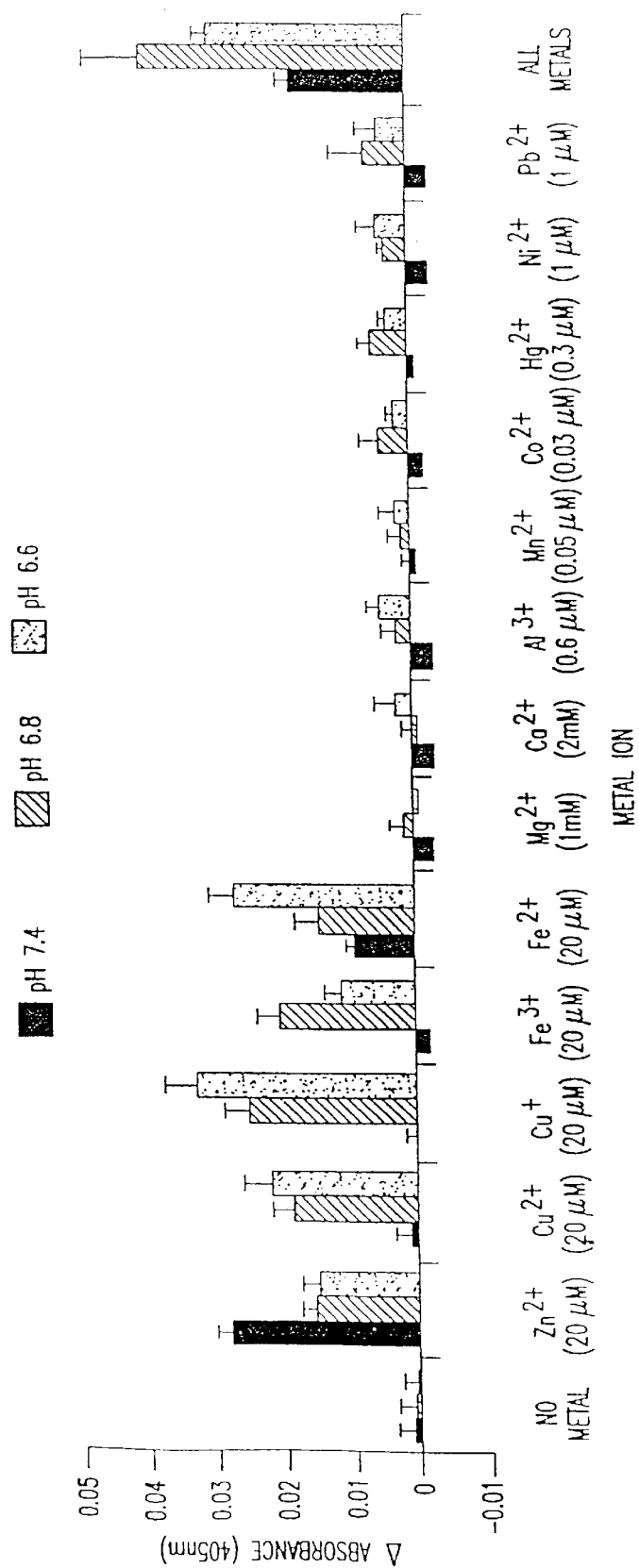
Figure 2C:
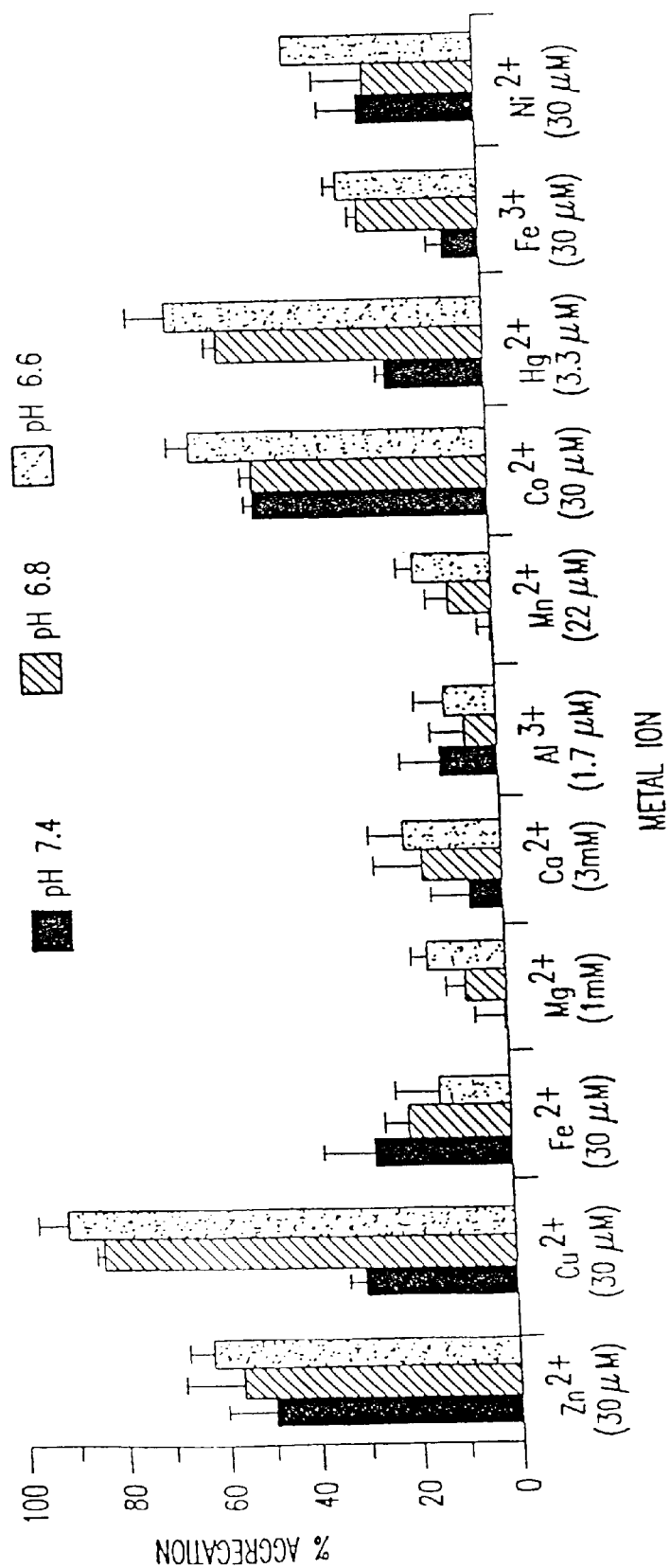

The results obtained using turbidometry as an index of aggregation are set forth in FIGS. 2A and 2C. The data indicate that the absorbency changes between reaction mixtures with and without metal ions at pH 6.6, 6.8 and 7.4.

Thus, $A\beta_{1-40}$ has both a pH insensitive and a pH sensitive metal binding site.

The present data indicate that pH alone dramatically affects Aβ solubility, inducing aggregation when the pH of the incubation approaches the pH of the peptide (pH about 5–6). Zinc induces 40–50% of the peptide to precipitate when the pH is greater than 6.2. However, when the pH is equal to or greater than 5.0, Zn(II) has little effect upon Aβ solubility. Between pH 6.2 and 5.0, the precipitating effects of Zn(II) and [H$^+$] are not summative.

The present data further indicate that, under very slightly acidic conditions, such as in the lactic acidotic AD brain, Cu(II) strikingly induces the aggregation of Aβ through an unknown conformational shift. Cu(II) is more effective than Zn(II) in precipitating Aβ and even induces aggregation at the physiologically relevant pH 6–7. Copper-induced aggregation of Aβ occurs as the pH falls below 7.0, comparable with conditions of acidosis in the AD brain (Yates, C. M., et a., *J. Neurochem.* 55:1624 (1990)). Investigation of the precipitating effects of most other metal ions in this system indicated that metal ion aggregation of Aβ is limited to copper and zinc, as illustrated above, although Fe(II) possesses a partial capacity to induce precipitation (Bush, A. I., et al., *Science* 268:1921 (1995)).

These results further suggest that subtle conformational changes in Aβ induced by [H$^+$] promote the interaction of $A\beta_{1-40}$ with metal ions, in particular Cu(II), allowing self-aggregation or resolubilization depending on the [H$^+$]. For example, a decrease in pH below 7.0 increases the β-sheet conformation (Soto, C., et al., *J. Neurochem.* 63:1191–1198 (1994)). This may allow Cu(II) to bind to soluble Aβ which could further alter the conformation of Aβ allowing for self-aggregation, or for the assembly of molecules to form aggregates. Conversely, increasing the pH above 7.0 promotes the α-helical conformation (Soto, C., et al., *J. Neurochem.* 63:1191–1198 (1994)). This may alter the conformational state of dimeric aggregated Aβ, releasing copper and thereby destabilizing the aggregate with the resultant release of Aβ into solution. Thus, in the presence of Cu(II), Aβ oscillates between an aggregated state and a soluble state depending upon the [H$^+$].

The biphasic relationship of Aβ solubility and pH mirrors the conformational changes previously observed in CD spectra within the N-terminal fragment (residues 1–28) of Aβ (Soto, C., et al., *J. Neurochem.* 63:1191–1198 (1994)), i.e., α-helical between pH about 1–4 and greater than about 7 and β-sheet between pH about 4–7. The formation of irreversible Aβ aggregates at pH about 5.5 supports the hypothesis that the β-sheet conformation is a pathway for Aβ aggregation into amyloid. Since aggregates produced by Zn(II) and Cu(II) under mildly acidic conditions (FIGS. 5A and 5B) are chelator/pH reversible, their conformation may be the higher energy α-helical conformation.

Figure 4A:
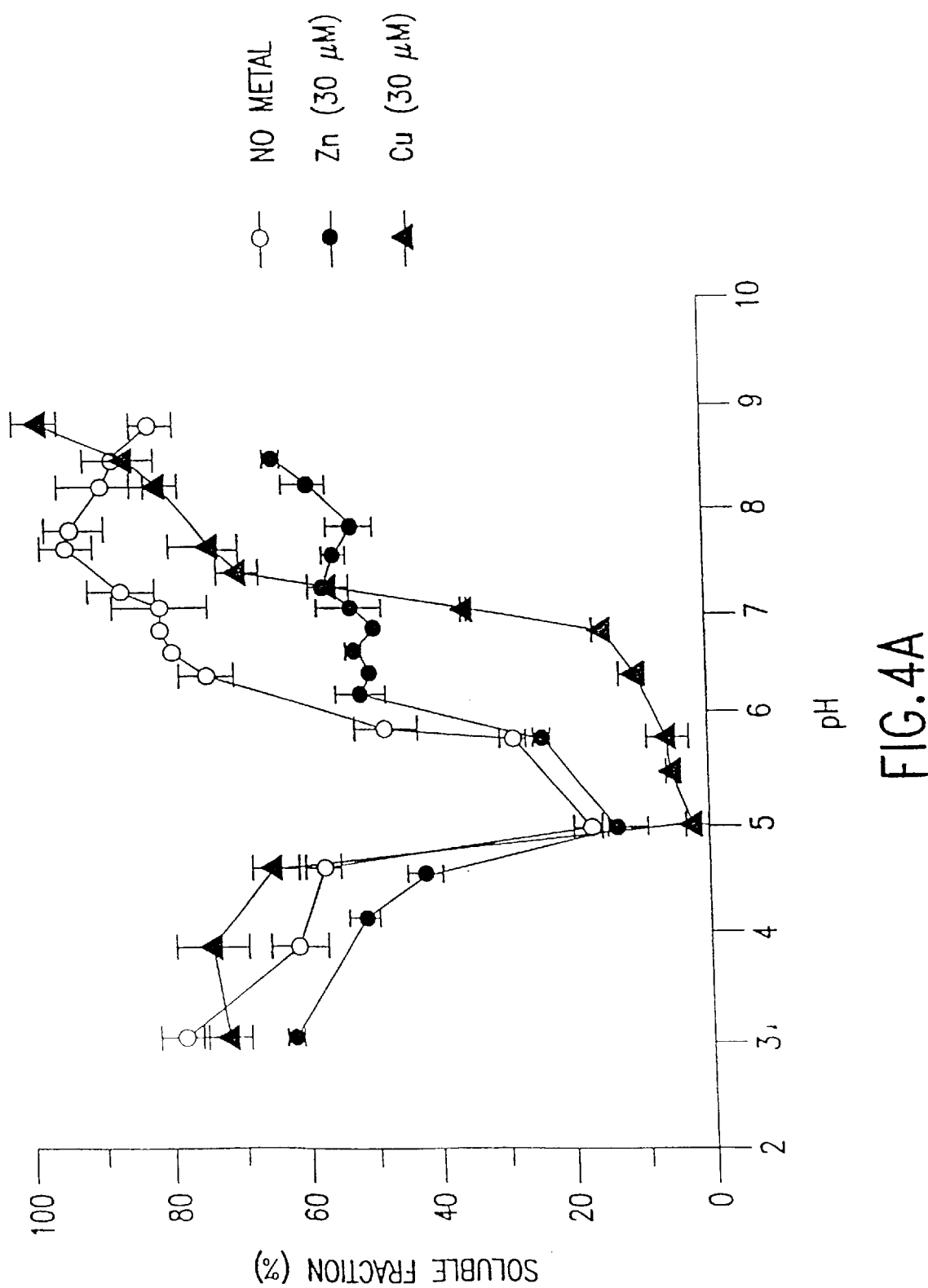
FIGS. 4A, 4B and 4C.
Figure 4B:
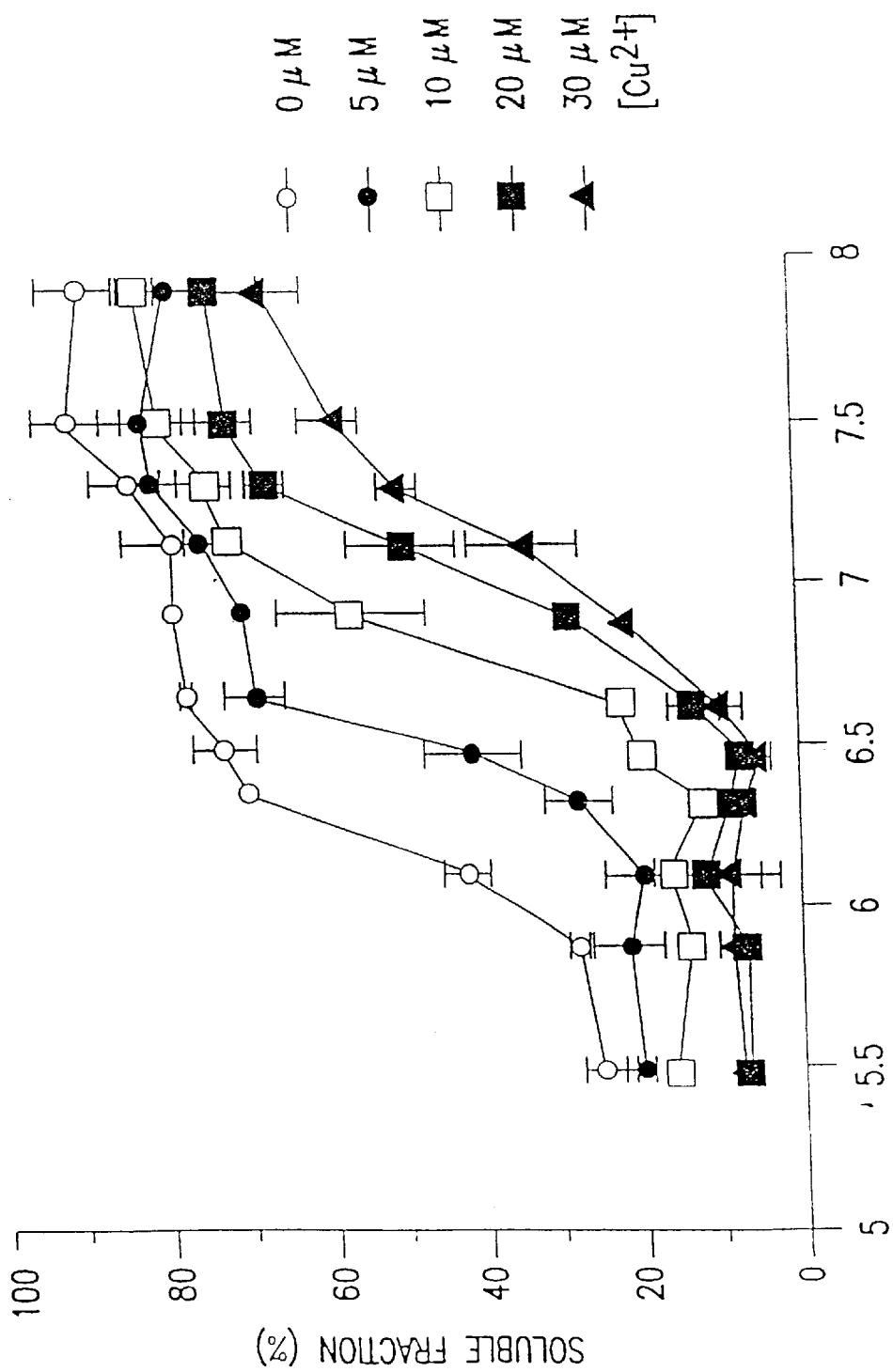
Figure 4C:
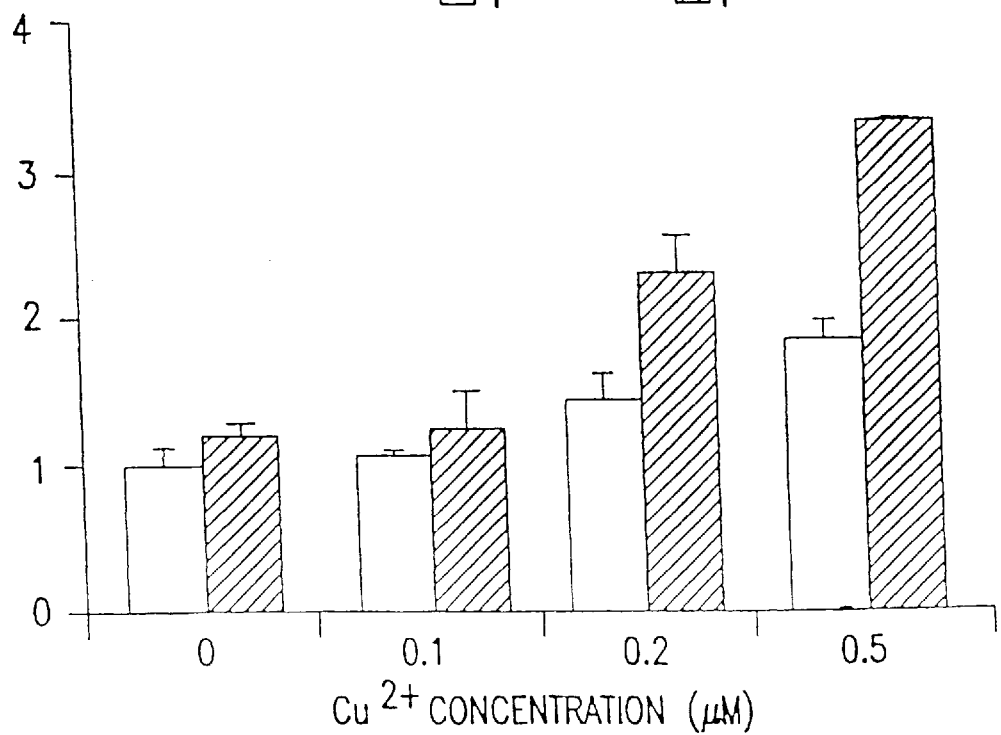

Since the conformational state and solubility of Aβ are altered at different pH (Soto, C., et al., *J. Neurochem.* 63:1191–1198 (1994)), the effects of [H$^+$] on Zn(II)- and Cu(II)-induced $A\beta_{1-40}$ aggregation were further studied. Results are shown in FIGS. 4A, 4B and 4C. FIG. 4A shows the proportion of soluble $A\beta_{1-40}$ remaining in the supernatant following incubation (30 minutes, 37° C.) at pH 3.0–8.8 in buffered saline±Zn(II) (30 μM) or Cu(II) (30 μM) and centrifugation (10,000 g, 20 minutes), expressed as a percentage of starting peptide. All data points are means±SD, n=3. [H$^+$] alone precipitates $A\beta_{1-40}$ (2.5 μM) as the solution is lowered below pH 7.4, and dramatically once the pH falls below about 6.3 (FIG. 4A). At pH 5.0, 80% of the peptide is precipitated, but the peptide is not aggregated by acidic environments below pH 5.0, confirming and extending earlier reports on the effect of pH on Aβ solubility (Burdick, D., *J. Biol. Chem.* 267:546–554 (1992)). Zn(II) (30 μM) induced a constant level (~50%) of aggregation between pH 6.2–8.5, while below pH 6.0, aggregation could be explained solely by the effect of [H$^+$].

Figure 7:
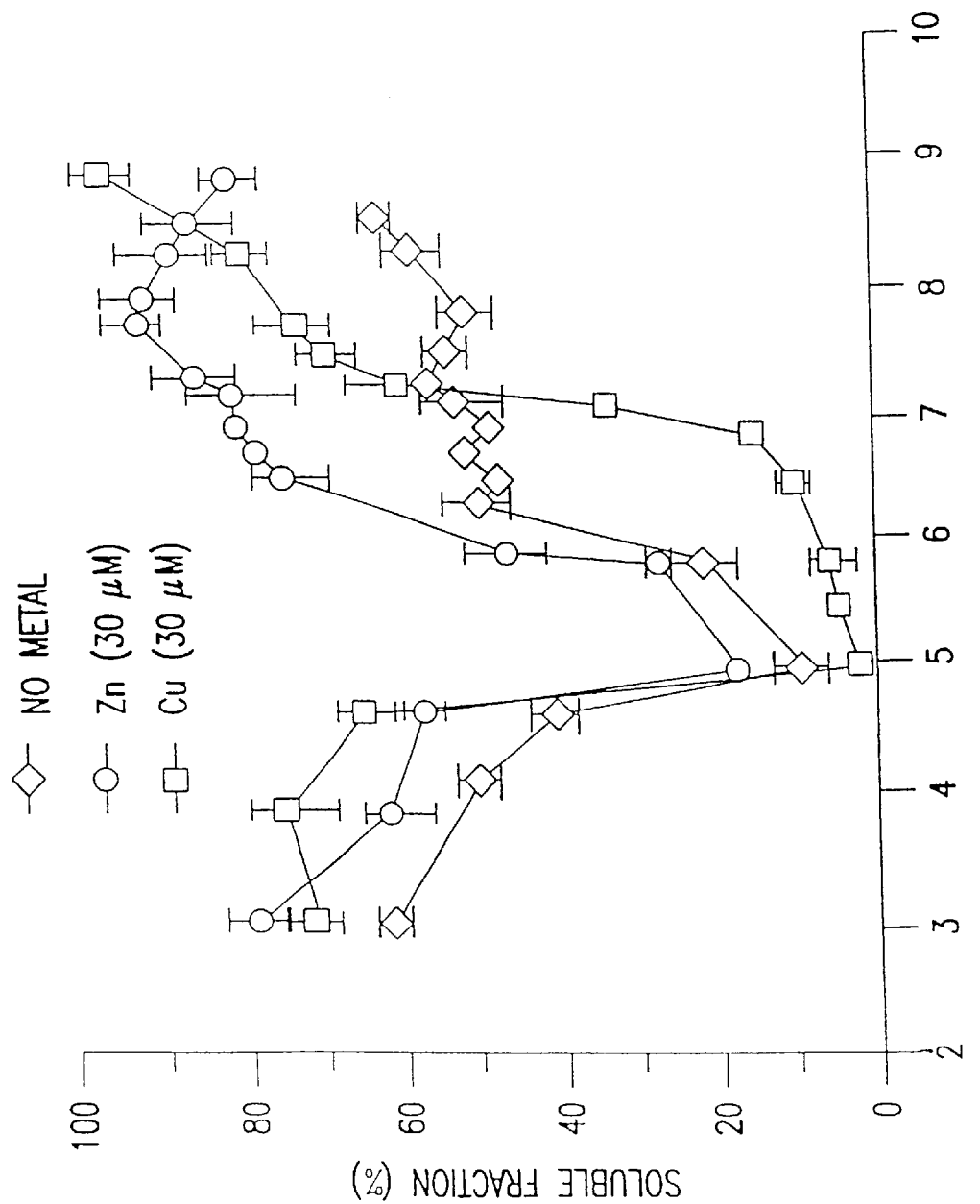
FIG. 7 is a graph showing the effects of pH, Zn(II) and Cu(II) upon Aβ formation.

In the presence of Cu(II) (30 μM), a decrease in pH from 8.8 to 7.4 induced a marked drop in Aβ$_{1-40}$ solubility, while a slight decrease below pH 7.4 strikingly potentiated the effect of Cu(II) on the peptide's aggregation. See FIG. 7. Surprisingly, Cu(II) caused more than 85% of the available peptide to aggregate at a pH of 6.8, a pH which plausibly represents a mildly acidotic environment. Thus, conformational changes in Aβ brought about by small increases in [H$^+$] result in the unmasking of a second metal binding site that leads to the rapid self-aggregation of Aβ. Below pH 5.0, the ability of both Zn(II) and Cu(II) to aggregate Aβ was diminished, consistent with the fact that Zn binding to Aβ is abolished below pH 6.0 (Bush, A. I., et al., *J. Biol. Chem.* 269:12152 (1994)), probably due to protonation of histidine residues.

The relationship between pH and Cu(II) on Aβ$_{1-40}$ solubility was then further defined by the following experiments: the proportion of soluble Aβ$_{1-40}$ remaining in the supernatant after incubation (30 minutes, 37° C.) at pH 5.4–7.8 with different Cu(II) concentrations (0, 5, 10, 20 and 30 μM), and centrifugation (10,000 g, 20 minutes), was measured and expressed as a percentage of starting peptide. All data points are means±SD, n=3 (FIG. 4B). At pH 7.4, Cu(II)-induced Aβ aggregation was 50% less than that induced by Zn(II) over the same concentration range, consistent with earlier reports (Bush, A. I., et al., *J. Biol. Chem.* 269:12152 (1994)). There was a potentiating relationship between [H$^+$] and Cu(II) in producing Aβ aggregation, i.e., as the pH fell, less Cu(II) was required to induce the same level of aggregation, suggesting that [H$^+$] is controlling Cu(II) induced Aβ$_{1-40}$ aggregation.

To confirm that this reaction occurs at physiological concentrations of Aβ$_{1-40}$ and Cu(II), a novel filtration immnunodetection system was employed. This technique enabled the determination of the relative amount of Aβ$_{1-40}$ aggregation in the presence of different concentrations of H$^+$ and Cu(II) (FIG. 4C). Specifically, the relative aggregation of run concentrations of Aβ$_{1-40}$ at pH 7.4 and pH 6.6 in the presence of different Cu(II) concentrations (0, 0.1, 0.2 and 0.5 μM) were determined by this method. Data represent mean reflectance values of immunoblot densitometry expressed as a ratio of the signal obtained when the peptide is treated in the absence of Cu(II). All data points are means±SD, n=2. This sensitive technique confirmed that physiological concentrations of Aβ$_{1-40}$ are aggregated under mildly acidic conditions and that aggregation is greatly enhanced by the presence of Cu(II) at concentrations as low as about 200 nm. Furthermore, as previously observed at higher Aβ$_{1-40}$ concentrations, a decrease in pH from 7.4 to 6.6 potentiated the effect of Cu(II) on aggregation of physiological concentrations of Aβ$_{1-40}$. Thus, Aβ$_{1-40}$ aggregation is concentration independent down to 8 nm when Cu(II) is available.

The rapid appearance, within days of Aβ deposits and APP immunoreactivity following head injury (Roberts, G. W., et al., *Lancet.* 338:1422–1423 (1991); Pierce, J. E. S., et al., *Journal of Neuroscience* 16:1083–1090 (1996)), rather than the more gradual accumulation of Aβ into more dense core amyloid plaques over months or years in AD may be compatible with the release of Zn(II), Cu(II) and mild acidosis in this time frame. Thus, pH/metal ion-mediated aggregation may form the basis for the amorphous Aβ deposits observed in the aging brain and following head injury, allowing the maintenance of endothelial and neuronal integrity while limiting the oxidative stress associated with injury that may lead to a diminishment of structural function.

Discussion

These results indicate that there are three physiologically plausible conditions which could aggregate Aβ: pH (Fraser, P. E., et al., *Biophys. J.* 60:1190–1201 (1991); Barrow, C. J. and Zagorski, M. G., *Science* 253:179–182 (1991); Burdick, D., *J. Biol. Chem.* 267:546–554 (1992); Barrow, C. J., et al., *J. Mol. Biol.* 225:1075–1093 (1992); Zagorski, M. G. and Barrow, C. J., *Biochemistry* 31:5621–5631 (1992); Kirshenbaum, K. and Daggett, V., *Biochemistry* 34:7629–7639 (1995); Wood, S. J., et al., *J. Mol. Biol.* 256:870–877 (1996)), the concentration of Zn(II) (Bush, A. I., et al., *J. Biol. Chem.* 269:12152 (1994); Bush, A. I., et al., *Science* 265:1464 (1994); Bush, A. I., et al., *Science* 268:1921 (1995); Wood, S. J., et al., *J. Mol. Biol.* 256:870–877 (1996)) and, under mildly acidic conditions, the concentration of Cu(II).

Interestingly, changes in metal ion concentrations and pH are common features of the inflammatory response to injury. Therefore, the binding of Cu(II) and Zn(II) to Aβ may be of particular importance during inflammatory processes, since local sites of inflammation can become acidic (Trehauf, P. S. and McCarty, D. J., *Arthr. Rheum.* 14:475–484 (1971); Menkin, V., *Am. J. Pathol.* 10:193–210 (1934)) and both Zn(II) and Cu(II) are rapidly mobilized in response to inflammation (Lindeman, R. D., et al., *J. Lab. Clin. Med.* 81:194–204 (1973); Terhune, M. W. and Sandstead, H. H., *Science* 177:68–69 (1972); Hsu, J. M., et al., *J. Nutrition* 99:425–432 (1969); Haley, J. V., *J. Surg. Res.* 27:168–174 (1979); Milaninio, R., et al., *Advances in Inflammation Research* 1:281–291 (1979); Frieden, E., in *Inflammatory Diseases and Copper*, Sorenson, J. R. J., ed., Humana Press, New Jersey (1980), pp. 159–169).

Serum copper levels increase during inflammation associated with increases in ceruloplasmin, a Cu(II) transporting protein that may donate Cu(II) to enzymes active in processes of basic metabolism and wound healing such as cytochrome oxidase and lysyl oxidase (Giampaolo, V., et al., in *Inflammatory Diseases and Copper*, Sorenson, J. R. J., ed., Humana Press, New Jersey (1980), pp. 329–345; Peacock, E. E. and van winkle, W., in *Wound Repair*, W. B. Saunders Co., Philadelphia (1976), pp. 145–155). Since the release of Cu(II) from ceruloplasmin is greatly facilitated by acidic environments where the cupric ion is reduced to its cuprous form (Owen, C. A., Jr., *Proc. Soc. Exp. Biol. Med.* 149:681–682 (1975)), periods of mild acidosis may promote an environment of increased free Cu(II). Similarly, aggregation of another amyloid protein, the acute phase reactant serum amyloid P component (SAP) to the cell wall polysaccharide, zymosan, has been observed with Cu(II) at acidic pH (Potempa, L. A., et al., *Journal of Biological Chemistry* 260:12142–12147 (1985)). Thus, exchange of Cu(II) to Aβ$_{1-40}$ during times of decreased pH may provide a mechanism for altering the biochemical reactivity of the protein required by the cell under mildly acidic conditions. Such a function may involve alterations in the aggregation/adhesive properties (FIGS. 1–5B) or oxidative functions of Aβ at local sites of inflammation.

Example 2

Free Radical Formation and SOD-like Activity of Alzheimer's Aβ Peptides a) Determination of Cu(I) and Fe(II)

This method is modified from a protocol assaying serum copper and iron (Landers, J. W. and Zak, B., *Chim. Acta.* 29:590 (1958)). It is based on the fact that there are optimal visible absorption wavelengths of 483 nm and 535 nm for Cu(I) complexed with bathocuproinedisulfonic (BC) anion and Fe(II) complexed with bathophenanthrolinedisulfonic (BP) anion, respectively. Determining molar absorption of these two complexes was accomplished essentially as follows: an aliquot of 500 $\mu$l of each complex (500 $\mu$M, in PBS, pH 7.4, with BC and BP ligands in excess) was pipetted into 1 cm-pathlength quartz cuvette, and their absorbencies were measured. Molar absorbencies were determined based on Beer-Lambert's Law. Cu(I)-BC has a molar absorbency of 2762 $M^{-1}$ $cm^{-1}$, while Fe(II)-BP has a molar absorbency of 7124 $M^{-1}$ $cm^{-1}$.

Determining the equivalent vertical pathlength for Cu(I)-BC and Fe(II)-BP in a 96-well plate was carried out essentially as follows: absorbencies of the two complexes with a 500 $\mu$M, 100 $\mu$M, 50 $\mu$M or 10 $\mu$M concentration of relevant metal ions (Cu(I) and Fe(II)) were determined by a 96-well plate reader (300 $\mu$l) and UV-vis spectrometer (500 $\mu$l), with PBS, pH 7.4, as the control blank. The resulting absorbencies from the plate reader regress against absorbencies by a UV-vis spectrometer. The slope k from the linear regression line is equivalent to the vertical pathlength if the measurement is carried out on a plate. The results are shown below:

|          | k(cm) | $r^2$ |
|----------|-------|-------|
| Cu(I)-BC | 1.049 | 0.998 |
| Fe(II)-BP | 0.856 | 0.999 |

With molar absorbency and equivalent vertical pathlength in hand, the concentrations ($\mu$M) of Cu(I) or Fe(II) could be deduced based on Beer-Lambert's Law using proper buffers as controls as follows:

$$\text{for } Cu^2 \ [Cu^2](\mu M) = \frac{\Delta A(483 \text{ nm})}{(2762 \times 1.049)} \times 10^6$$

$$\text{for } Fe^2 \ [Fe^2](\mu M) = \frac{\Delta A(535 \text{ nm})}{(7124 \times 0.856)} \times 10^6$$

where $\Delta A$ is the absorbency difference between sample and control blank.

b) Determination of $H_2O_2$

This method is modified from a $H_2O_2$ assay reported by Han, J. C. et al., (*Anal. Biochem.* 234:107 (1996)). The advantages of this modified $H_2O_2$ assay on a 96-well plate include high throughput, excellent sensitivity (~1 $\mu$M) and the elimination of the need for a standard curve of $H_2O_2$ which is problematic due to the labile chemical property of $H_2O_2$.

Aβ peptides were co-incubated with an $H_2O_2$-trapping reagent (Tris(2-carboxyethyl)-phosphine hydrochloride) (TCEP) (100 $\mu$M) in PBS (pH 7.4 or 7.0) at 37° C. for 30 minutes. Then 5,5'-dithio-bis(2-nitrobenzoic acid) (DBTNB) (100 $\mu$M) was added to react with remaining TCEP. The product of this reaction has a characteristic absorbency maximum of 412 nm. The assay was adapted to a 96-well format using a standard absorbency range. As shown in FIG. 11, Aβ$_{1-42}$ (10 $\mu$M) was incubated for 1 hour at 37° C., pH 7.4, in ambient air (first bar), with continuous argon purging (Ar), with continuous oxygen enrichment ($O_2$) at pH 7.0 (7.0) or in the presence of the iron chelator desferrioxamine (DFO) (220 $\mu$M). Variant Aβ species (10 $\mu$M) were also tested. Aβ$_{1-40}$, rat Aβ$_{1-40}$ (rAβ$_{1-40}$) and scrambled Aβ$_{1-40}$ (sAβ$_{1-40}$) were incubated for 1 hour at 37° C., pH 7.4, in ambient air. Values (mean±SD, n=3) represent triplicate samples minus values derived from control samples run under identical conditions in the presence of catalase (10 U/ml).

The chemical schemes for this novel method are:

Scheme I:

(TCEP) [Tris (2-carboxethyl) phosphine]

Scheme II:

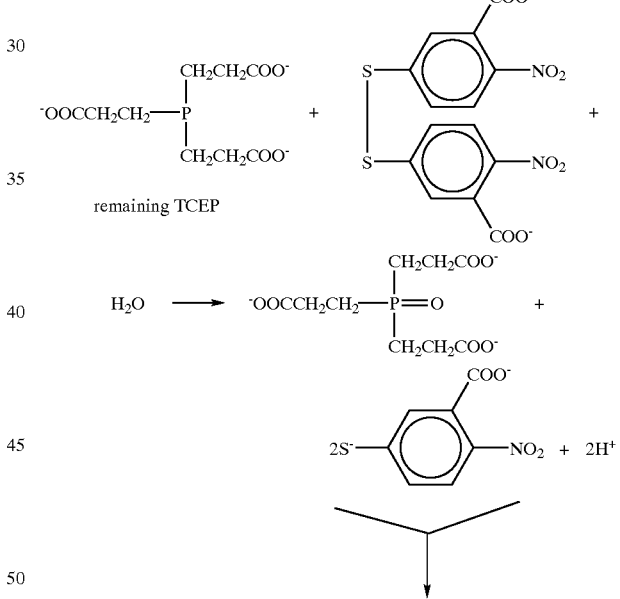

has characteristic optimal absorption peak at 412 nm with 14,150 $M^{-1}$ $cm^{-1}$ molar extinction coefficient TCEP.HCl was synthesized by hydrolyzing tris(2-cynoethyi)phosphine (purchased from Johnson-Mathey (Waydhill, Mass.)), in refluxing aqueous HCl (Burns, J. A. et al., *J. Org. Chem.* 56:2648 (1991)) as shown below:

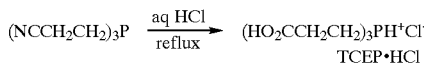

In order to carry out the above-described assay in a 96-well plate, it was necessary to calculate the equivalent vertical pathlength of 2-nitro-5-thiobenzoic acid (TMB) in a 96-well plate. This determination was carried out essentially as described for Cu(I)-BC and Fe(II)-BP above. The resulting absorbencies from the plate reader regress against absorbencies by a UV-vis spectrometer. The slope k from the linear regression line is equivalent to the vertical pathlength if the measurement is carried out on a plate. The results for TMB are as follows:

| k | r2 |
|---|---|
| 0.875 | 1 |

The concentration of $H_2O_2$ can then be deduced from the difference in absorbency between the sample and the control (sample plus 1000 U/μl catalase) as indicated below:

$$[H_2O_2](\mu M) = \frac{\Delta A(412\ nm)}{(2 \times 0.875 \times 14150)}$$

c) Determination of OH.

Determination of OH. was performed as described in Gutteridge et al. (*Biochim. Biophys. Acta* 759: 38–41 (1983)).

d) Cu(I) Generation by Aβ: Influence of Zn (II) and pH

Aβ (10 μM in PBS, pH 7.4 or 6.8) was incubated for 30 minutes (37° C.) in the presence of Cu(II) (10 μM)±Zn(II) (10 μM). Cu(I) levels (n=3, ±SD) were assayed against a standard curve. These data confirm that the presence of Zn(II) can mediate the reduction of Cu(II) in a mildly acidic environment. The effects of zinc upon the reactions are strongly in evidence, but complex. Since the presence of 10 μM zinc will precipitate the peptide, it is clear that the peptide possesses redox activity even when it is not in the soluble phase, suggesting that cortical Aβ deposits will not be inert in terms of generating these highly reactive products. Cerebral zinc metabolism is deregulated in AD, and therefore levels of interstitial zinc may play an important role in adjusting the Cu(I) and $H_2O_2$ production generated by Aβ.

Results

AβExhibits Metal-dependent and Independent Redox Activity

The bathocuproine and bathophenanthroline reduced metal assay technique employed by Multhaup et al. was used to determine that APP itself possesses a Cu(II) reducing site on its ectodomain (Multhaup, G., et al., *Science* 271:1406 (1996)). Since one of the caveats in using the reduced metals assay is that the detection agents can exaggerate the oxidation potential of Cu(II) or Fe(III), other redox products were explored by assays where no metal ion indicators were necessary. It was discovered that hydrogen peroxide was rapidly formed by Aβ species (FIG. 11). Thus, Aβ produces both $H_2O_2$ and reduced metals whilst also binding zinc. Structurally, this is difficult to envisage for a small peptide, but we have recently shown that Aβ is dimeric in physiological buffers. Since $H_2O_2$ and reduced metal species are produced in the same vicinity, these reaction products are liable to produce the highly toxic hydroxyl radical by Fenton chemistry, and the formation of hydroxyl radicals from these peptides has now been shown with the thiobarbituric acid assay. The formation of hydroxyl radicals correlates with the covalent polymerization of the peptide (FIG. 9) and can be blocked by hydroxyl scavengers. Thus the concentrations of Fe, Cu, Zn and $H^+$ in the brain interstitial milieu could be important in facilitating precipitation and neurotoxicity for Aβ by direct (dimer formation) and indirect (Fe(II)/Cu(I) and $H_2O_2$ formation) mechanisms.

Figure 6:
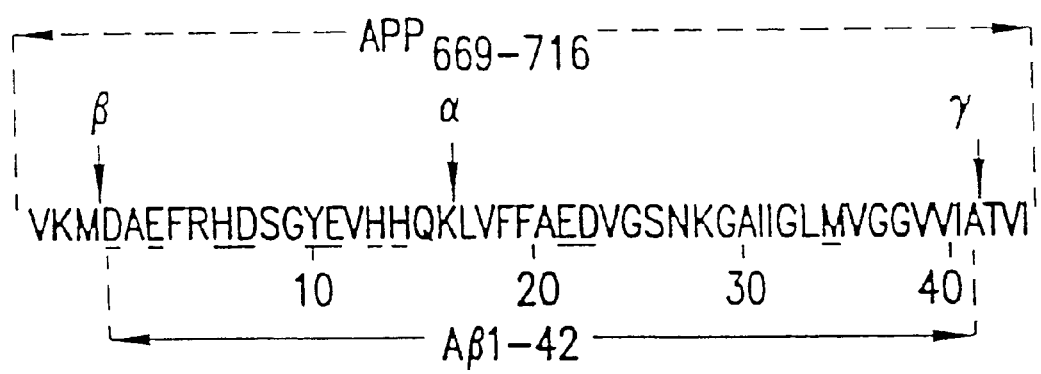
FIG. 6 shows the amino acid sequence (SEQ ID NO:1) of $APP_{669-716}$ near $Aβ_{1-42}$. Rat Aβ is mutated (R5G, Y10F, H13R; bold). Possible metal-binding residues are underlined.

$H_2O_2$ production by Aβ explains the mechanism by which $H_2O_2$ has been described to mediate neurotoxicity (Behl, C., et al., *Cell* 77:827 (1994)), previously thought to be the product of cellular overproduction alone. Interestingly, the scrambled Aβ peptide produces appreciable $H_2O_2$ (FIG. 6), but no hydroxyl radicals. This is because the scrambled Aβ peptide is unable to reduce metal ions. Therefore, we conclude that what makes Aβ such a potent neurotoxin is its capacity to produce both reduced metals and $H_2O_2$ at the same time, producing hydroxyl radicals by the Fenton reaction, especially if the $H_2O_2$ is not rapidly removed from the vicinity of the peptide. Catalase and glutathione peroxidase are the principal means of catabolizing $H_2O_2$, and their levels are low in the brain, especially in AD, perhaps explaining the propensity of Aβ to accumulate in brain tissue as discussed above.

Example 3

(a) Aβ Activity in a Commonly-Used SOD Assay

To establish that the anti-superoxide effects of Aβ are evident in vivo, two transgenic mouse lines were studied that express the carboxyl-terminal 100 amino acids of human APP with (mouse line Tg C100.V717F) and without the familial AD (FAD) mutation (mouse line Tg C100.WT) (Li Q. X., et al., *J. Neurochem.* (1999)). These mice do not display any of the typical neuropathological hallmarks of AD. In addition to overexpressing human Aβ, the Tg C100.V717F mice carry a mutation in the APP gene at residue 717 and consequently produce moderately elevated levels of $A\beta_{1-42}$ (Suzuki, N., et al, *Science* 264. 1336–1340 (1994)).

Methods

Fibroblast cultures. Fibroblasts were harvested from the tails of two Tg C100.WT and two Tg C100.V717F mice. The tissue was minced in 5 ml 0.25% collagenase (w/v) and incubated for 2×30 minutes at 37° C., 5% $CO_2$, with occasional shaking. Following centrifugation for 2 minutes at 1000 g, and 2 washes with PBS, the tissue samples were transferred to culture flasks containing supplemented culture medium (DMEM+10% FCS), and incubated for 3–5 days at 37° C., 5% $CO_2$. The fibroblasts were grown to confluence over 2–3 passages, and then transferred to 48-well plates at 3–5×10⁴ cells/well (xanthine oxidase treatment) or to 6-well plates at 0.5×10⁶ cells/well (glutathione assay).

Dose response with xanthtine/xanthtine oxidase. Fibroblasts in multi-well plates were treated with 75 μM xanthine and increasing concentrations of xanthine oxidase (0, 0.2, 0.5 and 1 U/ml). Control cells were incubated in the absence of xanthine and/or xanthine oxidase. Triplicate wells were employed for each treatment. Following an overnight incubation at 37° C., 5% $CO_2$, cell viability was assayed using the MTT assay.

Treatment with synthetic $A\beta_{1-42}$ and SOD1. Tg C100.WT fibroblasts were cultured in 48-well plates at 1×10⁴ cells/well and treated with 50 μM xanthine and 0.2 U/ml xanthine oxidase. Control cells were incubated in the absence of xanthine oxidase. Six wells were employed for each treatment. In addition, some fibroblasts were treated with freshly-prepared synthetic $A\beta_{1-42}$ (0.1–10 nm) or 50 U/ml SOD1. Following an overnight incubation at 37° C., 5% $CO_2$, cell viability was assayed using the MTT assay.

SOD1, Aβ peptides, insulin and amylin (r=rat, h=human) were added (0.5 μM) to a mixture of xanthine (1 mM) and xanthine oxidase (0.015 U/ml) in PBS and EDTA (0.1 mM), pH 7.4, with Nitro Blue Tetrazolium (NBT, 0.1 mM) serving as the $O_2^-$ detection agent. Absorbency changes (560 nm) were monitored over a 3 minute period for the purple formazan formation which indicates $O_2^-$ reactivity towards NBT. Percentage inhibition of $O_2^-$ reactivity towards NBT with reference to the inhibition caused by 0.5 μM SOD1 (100%) was used for comparing the SOD-like activities of the Aβ peptides. See FIG. 1.

Results

Figure 14A:
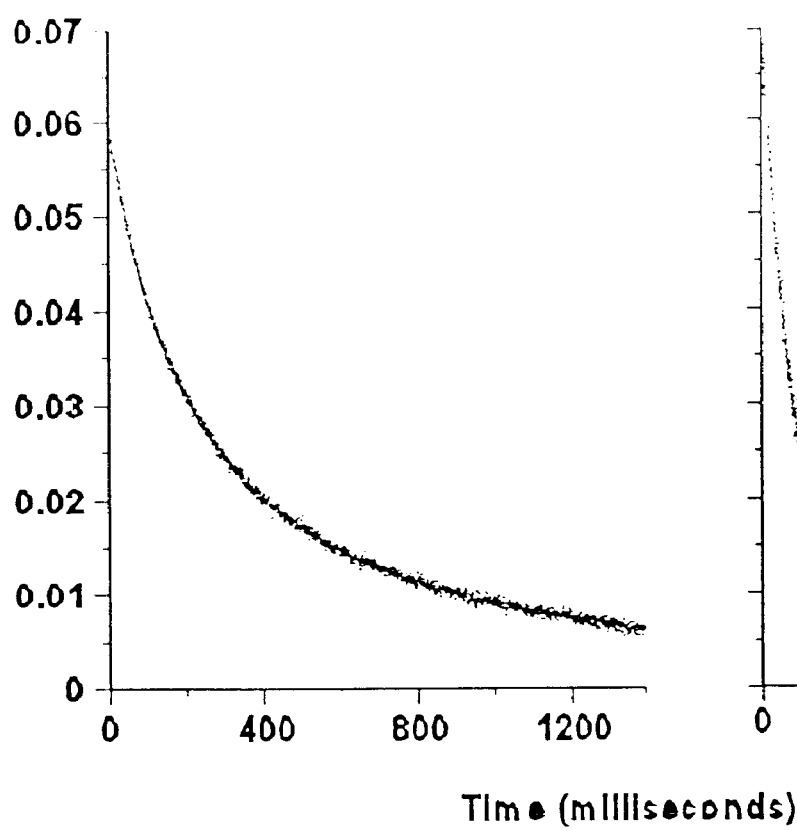
FIGS. 14A and 14B are two examples of spectrophotometric records of the decay of superoxide generated by pulse radiolysis in the presence of $CuZn-Aβ_{1-42}$ (right panel) (FIG. 14A) exhibiting first-order kinetics, or in the presence of $Zn-Aβ_{1-42}$ (left panel) (FIG. 14B) exhibiting second-order kinetics (note the different time-intervals on the x-axes) for the catalysis of superoxide dismutation by major Aβ species.
Figure 14B:
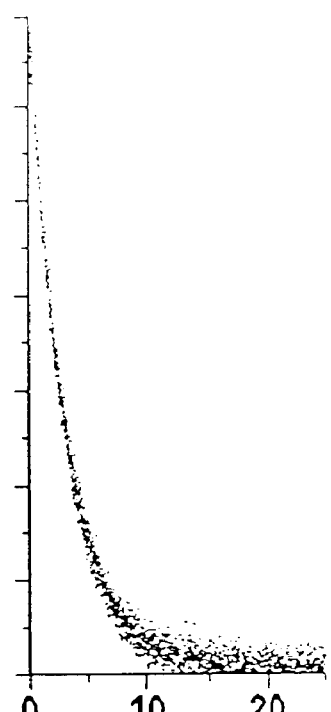

To test the hypothesis that moderately increased levels of $Aβ_{1-42}$ in vivo confer an increased antioxidant capacity, fibroblasts were cultured from the C100 transgenic mice and exposed to a xanthine/xanthine oxidase-mediated $O_2^-$ challenge. $Aβ_{142}$ overexpressing cells (Tg C100.V717F) were less susceptible to superoxide damage than the non-overexpressing cells (Tg C100.WT), as assessed by viability assays (FIG. 14A). To test whether $Aβ_{1-42}$ in overexpressing cells protects in a superoxide dismutase (SOD)-like fashion, WT fibroblasts were rescued with exogenous synthetic $Aβ_{1-42}$ and SOD1. Nanomolar concentrations of freshly-prepared human $Aβ_{1-42}$ increased the resistance of Tg C100.WT fibroblasts to superoxide damage (FIG. 14B). This effect was comparable to treatment with 50 U/ml SOD1, suggesting that $Aβ_{1-42}$ can act as a SOD1 mimic.

The data support the hypothesis that Aβ may be purposively released as an antioxidant. The release of the peptide as a response to oxidative stress, e.g., superoxide stress, may explain why the peptide concentrates as diffuse deposits in neurological events associated with oxidative stress, such as following head injury (Roberts, G. W., et al., *Lancet* 338.1422–1423 (1991)), why the peptide has been observed to be released when cells are oxidatively stressed (Frederikse, P. H., et al., *J. Biol. Chem.* 271: 10169–10174 (1996)), and how the peptide acts to inhibit lipid peroxidation of brain membranes in vitro (Andorn, A. C. and Kalaria, R. N., *Neurobiol. Aging* 19(4S): S40 (1998)). Although neurotoxic at micromolar concentrations, $Aβ_{1-40}$ was originally reported to exhibit neurotrophic activity in cell cultures at low nanomolar concentrations (Yankner, B. A., et al., *Science* 250: 279–282 (1990)) compatible with antioxidant properties.

(b) A screening Test to Determine which Drugs will Inhibit the Anti-superoxide Function of Aβ

The test compound is added to the Aβ solution and SOD-like activity is measured by any means that measures such activity, e.g., pulse radiolysis, or in the high-throughput system, NBT assay, (FIG. 12). A test compound that does not inhibit the ability of antioxidant Aβ to scavenge superoxide generated in the system (usually by xanthine/xanthine oxidase), may be predicted not to inhibit the antioxidant function of Aβ in vivo.

(c) Tests to Determine the use of $O_2$ for the Production of $H_2O_2$ and Whether Aβ Catalyzes the Dismutationi of Superoxide It was suspected that use of $O_2$ for the production of $H_2O_2$ might reflect an error in substrate specificity, and that Aβ may also catalyze the dismutation of superoxide. To test these possibilities, the decay of superoxide generated by pulse radiolysis in the presence of synthetic $Aβ_{1-40}$ and $Aβ_{1-42}$ that had been metallated according to procedures previously developed for the study of SOD1 catalytic activity was studied (Goto, J. J., et al., *J. Biol Chem* 273(46): 30104–9 (1998)).

Methods

Synthetic peptides. Aβ peptides 1–40 and 1–42 were synthesized by the W. Keck Laboratory, Yale University, New Haven, Conn. Confirmatory data were obtained by reproducing experiments with Aβ peptides synthesized and obtained from other sources: U.S. Peptides, Bachem (Torrance, Calif.), and Sigma. Aβ peptide stock solutions were prepared in Chelex-100 resin (BioRad, Calif.) treated water and quantified, according to published procedures (Atwood, C. S., et al., *Journal of Biological Chemistry* 273:12817–12826 (1998)). To prepare metallated peptide, Aβ (60 μM) was co-incubated with Cu(II)-glycine, Zn(II)-glycine (13) (300 μM), or both, in PBS (66 mM phosphate, 150 mM NaCl, pH 7.4) for 24 hours at 37° C. As expected (Bush, A. I., et al., *Science* 265:1464–1467 (1994); Atwood, C. S., et al., *Journal of Biological Chemistry* 273:12817–12826 (1998)), Cu and Zn immediately caused Aβ to precipitate, and the peptide-metal ion preparations were handled as suspensions for the experimental studies. The metallated peptide mixtures were exhaustively dialyzed (3.5 kD cut-off. Pierce) against Chelex-100 treated doubly-distilled water (5×2 h×1 liter exchanges) to remove unbound, and low-affinity bound metal. This treatment caused much of the peptide aggregate to resolubilize, since the Zn- and Cu-mediated aggregation of Aβ is reversible (Huang, X., et al., *J. Biol. Chem.* 272:26464–26470 (1997); Atwood, C. S., et al., *Journal of Biological Chemistry* 273:12817–12826 (1998)). Samples of the unmetallated and metallated peptide products, as well as the experimental buffers, were measured for metal content or contamination by inductively-coupled plasma mass spectrometry (Varian Ultramass 700, Melbourne, Australia) and atomic absorption spectroscopy.

Pulse radiolysis. Determinations of SOD activities were performed by pulse radiolysis (Cabelli, D. E., et al., *J. Am. Chem. Soc.* 109(12):3665–3669 (1987)) using a 2 Mev Van de Graaff electron accelerator and kinetic UV/VIS spectroscopy system (Department of Chemistry, Brookhaven National Laboratory, Upton, N.Y.). Pulses of 1.8 MeV electrons (>>500-ns pulse duration) were delivered to a quartz cell (2-cm optical path length) containing Aβ peptide (1–20 μM) in air-saturated PBS, pH 7.4, containing 10 mM formate at 25° C. Dosimetry was established using the KSCN dosimeter, assuming that (SCN) has a G value of 6.13 and a molar absorptivity of 7950 $M^{-1}cm^{-1}$ at 472 nm. Irradiation of water by the electron beam generates the primary radicals, .OH, $e_{aq}^-$ and .H. These radicals are efficiently converted into $O_2^-$ in the presence of formate and oxygen via the following reactions: $.OH + HCO_2.^- \rightarrow CO_2.^- + H_2O$ followed by $CO_2.^- + O_2 \rightarrow CO_2 + O_2^-$, $e_{aq}^- + O_2^-$ and $.H + O_2 \rightarrow HO_2.$, where $HO_2. = H^+ + O_2^-$. The decay of $O_2^-$ was monitored at 250–270 nm and the first order rate for the catalytic dismutation of $O^2$ ($k_{cat}$) in the presence of metallated protein was then extracted from the observed change in absorbance ($k_{obs}$ at 260 nm) with respect to time and molar protein concentration.

Results

To test the individual contribution of Cu and Zn to the activities of Aβ, four preparations of Aβ ($Aβ_{1-40}$ and $Aβ_{1-42}$) were made: Aβ treated with Zn (Zn-Aβ), Aβ treated with Cu (Cu-Aβ), Aβ treated simultaneously with Cu and Zn (CuZn-Aβ), and Aβ that was not treated with either metal ion. After treatment, the peptide preparations were exhaustively dialyzed to remove unbound metal ions and studied for their respective influence on the first order decay of superoxide generated by pulse radiolysis.

Figure 15A:
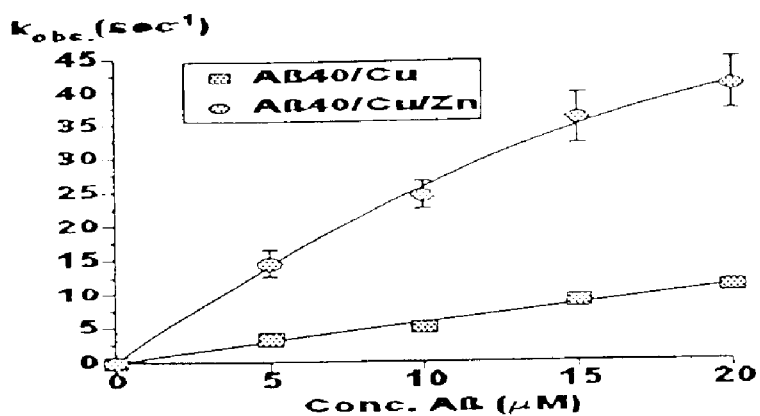
FIGS. 15A–15C are graphs showing the observed increase in the decay of $O_2^-$ ($k_{obs}$) above the decay expected from spontaneous disproportionation.
Figure 15B:
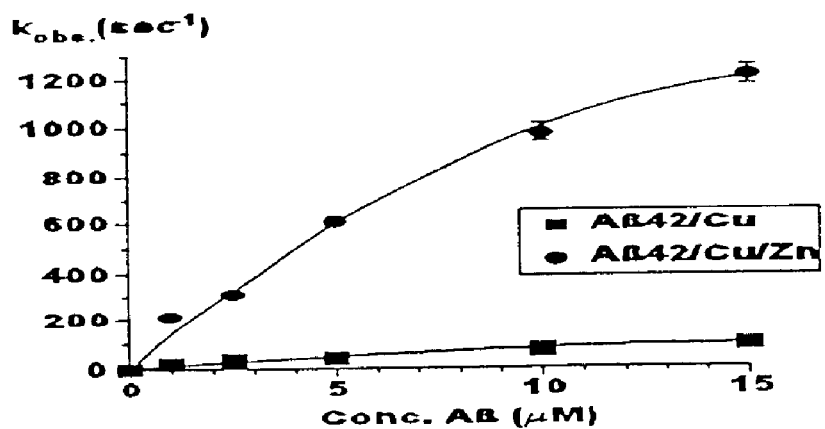

It was found that unmetallated Aβ (Table 1) and Zn-Aβ (FIGS. 14A and 14B, Table 1) had no effect on the spontaneous disproportionation of superoxide. However, significant catalytic activity was observed for Cu-treated Aβ preparations (FIGS. 14–15, Table 1). Cu-Aβ$_{1-42}$ dismutase activity (2.24×10$^7$ M$^{-1}$ sec$^{-1}$, Table 1, FIG. 15B) was much greater than that of Cu-Aβ$_{1-40}$ (6.4×10$^5$ M$^{-1}$ sec$^{-1}$, Table 1, FIG. 15A), and the SOD-like activities of both Cu-treated Aβ preparations were greatly enhanced by co-treatment with Zn(II). The activity of CuZn-Aβ$_{1-42}$ (2.1×10$^8$ M$^{-1}$ sec$^{-1}$, Table 1, FIG. 15B) was also much greater than CuZn-Aβ$_{1-40}$ (2.90×10$^6$ M$^{-1}$sec$^{-1}$, Table 1, FIG. 15A). In parallel experiments, mass spectroscopy and polyacrylamide gel electrophoresis found no modifications of CuZnAβ$_{1-42}$ incubated for five minutes with 30 μM KO$_2$ in PBS, pH 7.4, suggesting that the peptide is not consumed upon scavenging superoxide. The k$_{cat}$ of CuZn-Aβ preparations decreased as the peptide concentration rose (FIGS. 15A and 15B), suggesting that the peptide becomes less efficient at catalyzing dismutation at higher concentrations, possibly because of aggregation.

Measurement of the metal bound to the peptide preparations revealed that Aβ possessed catalytic activity only where it had bound Cu. Cu-Aβ$_{1-40}$ and CuZn-Aβ$_{1-40}$ bound 0.3 and 0.4 mole equivalents of Cu, respectively (Table 1). Cu-Aβ$_{1-42}$ bound 0.7 mole equivalents of Cu per subunit, but CuZn-Aβ$_{1-42}$ bound 1.4 mole equivalents of Cu indicating that co-incubation with Zn potentiated the loading of Cu onto the peptide. Zn was not detected bound to any of these peptide preparations.

The dismutase activity (k$_{cat}$) of Aβ (1–40 or 1–42) rose exponentially per mole of Cu bound (FIG. 15C), indicating that the k$_{cat}$ is enhanced by peptide-mediated factors, and is not simply proportional to bound Cu equivalents. Since Aβ$_{1-40}$ and Aβ$_{1-42}$ can bind up to 2 mole equivalents of Cu per subunit at pH 7.4 (Atwood et al., unpublished observations), sufficient Cu binding with the metallation and dialysis procedures to maximize the enzymic activity of Aβ may not have been achieved. Therefore, it is possible that the k$_{cat}$ of metallated Aβ$_{1-40}$ may approach that of Aβ$_{1-42}$ when binding equal Cu per peptide subunit. A Cu-dependent saturation analysis of Aβ$_{1-40}$ and Aβ$_{1-42}$ activities awaits the development of procedures that optimize metallation of the synthetic peptide or procedures that allow the non-denaturing purification of milligram quantities of the native peptide from a biological source.

Since free Cu(II) catalyzes superoxide dismutation at pH 7.4 (k$_{cat}$=1×10$^9$ M$^{-1}$ sec$^{-1}$) (Cabelli, D. E., et al., *J. Am. Chem. Soc.* 109(12):3665–3669 (1987)), it was considered whether, by preparing the peptide with excess Cu(II), it may have been possible for a small amount of Cu(II) to have contaminated the study. Despite the attempt to remove all free Cu(II) by exhaustive dialysis of the Cu-treated peptide solutions, free contaminating Cu in the buffer itself was found to be 60 nm. To determine whether the dismutase catalysis observed was a product of free contaminating Cu(II), the activity of CuZn-Aβ$_{1-42}$ (5 μM) in the presence of arginine (40 μM) was measured, and it was found that the presence of arginine did not decrease the k$_{obs}$. Arginine chelates Cu(II) (logK$_{app}$=5.9), but has insufficient affinity at micromolar concentrations to remove Cu(II) from Aβ$_{1-42}$ (Atwood et al., submitted). Free Cu(II) catalyzes superoxide dismutation at pH 7.4 with a greater k$_{cat}$ (1×10$^9$ M$^{-1}$ sec$^{-1}$) than Arg-Cu(II) (2×10$^8$ M$^{-1}$ sec$^{-1}$) (Cabelli, D. E., et al., *J. Am. Chem. Soc.* 109(12):3665–3669 (1987)). Therefore, if free contaminating Cu(II) was responsible for the apparent catalytic activity of the CuZn-Aβ$_{1-42}$ preparation, the arginine would have decreased the apparent rate of dismutation.

Figure 15C:
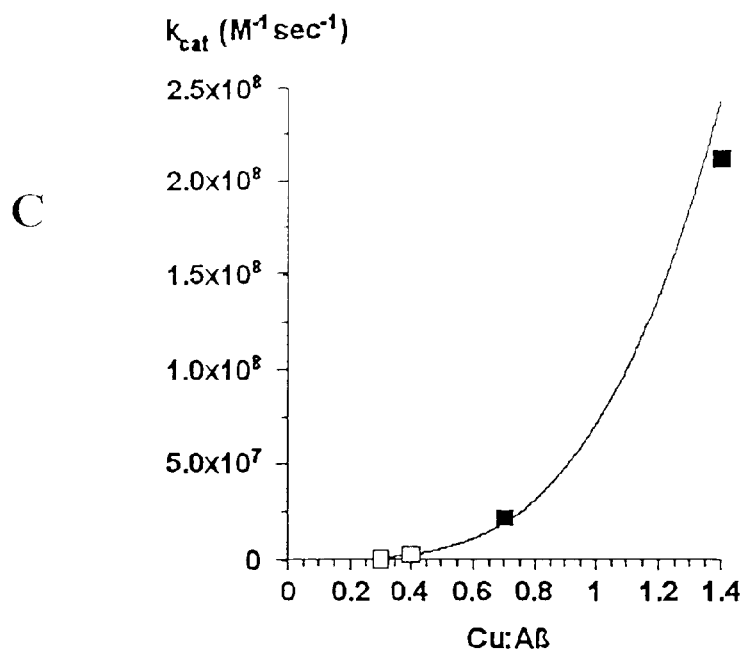

A second line of evidence that the SOD-like activity observed for Cu-Aβ was due to the peptide-Cu complex and not due to free contaminating Cu(II) is that the k$_{cat}$ rose exponentially as a product of (apparently bound) Cu(II) concentration (FIG. 15C). This means that the Cu-dependent activities observed are promoted by interaction with the peptide, and are not merely a product of the total Cu concentration. If the SOD activities observed were merely due to trace Cu(II) contamination introduced by the peptide preparation, then the k$_{cat}$ values would be constant at 1×10$^9$ M$^{-1}$ sec$^{-1}$ (Cabelli, D. E., et al., *J. Am. Chem. Soc.* 109(12): 3665–3669 (1987)) despite the increasing total Cu concentration (FIG. 15C).

A third line of evidence that the SOD-like activity observed for Cu-Aβ was due to the peptide-Cu complex and not due to free contaminating Cu(II) is that the activity was markedly increased by treatment of the peptide-Cu complex with Zn(II) prior to the exhaustive removal of unbound metals by dialysis (FIGS. 15A and 15B, Table 1). Since competition with Zn(II) during the metal-loading phase of the preparation would, if anything, be expected to decrease Cu(II) binding to the peptide, the observation that Zn(II) pretreatment increases activity is not likely to be explained by the presence of increased free Cu(II) in the samples that were analyzed after dialysis.

TABLE 1

|  | k$_{cat}$(M$^{-1}$sec$^{-1}$) | Cu:Aβ ratio | Zn:Aβ ratio |
| --- | --- | --- | --- |
| Aβ40 or Zn-Aβ40 | 0.0 | 0.0 | 0.0 |
| Aβ42 or Zn-Aβ42 | 0.0 | 0.0 | 0.0 |
| Cu-Aβ40 | 0.64 × 10$^6$ | 0.3 | 0.0 |
| CuZn-Aβ40 | 2.90 × 10$^6$ | 0.4 | 0.0 |
| Cu-Aβ42 | 2.24 × 10$^7$ | 0.7 | 0.0 |
| CuZn-Aβ42 | 2.11 × 10$^8$ | 1.4 | 0.0 |
| SOD1 | 2 × 10$^9$ | 2 | 2 |

Table 1. Rate Constants (k$_{cat}$) for Dismutation of HO$_2$/O$_2^-$ Catalyzed by Aβ-metal Complexes. Because dismutase activity decreased as the Aβ concentration increased (FIGS. 15A and 15B), k$_{cat}$ was calculated as the slope of curve (k$_{obs}$ vs peptide concentration) at the lowest peptide concentration tested. Representative peptide samples were measured for metal content. The k$_{cat}$ for SOD1 obtained under the same conditions is indicated for comparison.

These observations indicate that metallated Aβ possesses significant SOD-like catalytic activity. Although the data were obtained with micromolar concentrations (1 to 20 μM) of peptide, the k$_{cat}$ of metallated Aβ (in SOD activity units of M$^{-1}$ sec$^{-1}$) would not be expected to decrease at lower concentrations. Nevertheless, recent observations have measured the total concentrations of Aβ in the AD-affected brain at approximately 10 μM of which approximately 200 nm is soluble (Cherny, R. A., et al., *Journal of Biological Chemistry*, In press (1999)), and protein-bound plasma Aβ$_{1-42}$ levels are at micromolar concentrations (Kuo, Y. M., et al., *Biochem. Biophys. Res. Commnun.* 257(3):787–91 (1999)). Therefore, these observations suggest that the Aβ pools could contribute significant SOD-like activity in vivo, if they are metallated.

The activity of SOD1 was originally purified from erythrocytes (McCord, J. M., and Fridovich, I., *J. Biol. Chem.* 244(22):6049–55 (1969)), and therefore had the native proportion of Cu and Zn bound to the protein, as do commercially available SOD1 preparations. It is not yet known whether Aβ is a metalloprotein in vivo, although its co-precipitation with Cu and Zn (Lovell, M. A., et al., *J. Neurol. Sci.* 158(1):47–52 (1998)) in plaque deposits, and the ability of Cu- and Zn- selective chelators to dissolve Aβ aggregates from post-mortem AD brain specimens (Cherny, R. A., et al., *Journal of Biological Chemistry*, In press (1999)), suggest that metallation of brain Aβ with Cu and Zn is likely in AD. There is no free pool of intracellular Cu (Rae, T. D., et al., *Science* 284(5415):805–8(1999)), meaning that Aβ would probably need to be metallated with Cu in the endoplasmic reticulum by a loading mechanism like the CCS mechanism for SOD if it were to have activity before it is released. However, much less is known about the pool of extracellular Cu. Cu is released (approximately 15 $\mu$M) during synaptic transmission (Hartter, D. E., and Barnea, A., *J. Biol. Chem.* 263:799–805 (1998)), and acidotic conditions such as those expected in the AD-affected brain will promote the binding of Cu(II) to Aβ (Atwood, C. S., et al., *Journal of Biological Chemistry* 273:12817–12826 (1998)). In light of this background, the current in vitro observations are highly likely to reflect Aβ SOD-like activity in vivo, at least in AD.

The data also confirm that the affinity of Aβ for Cu(II) is remarkably high since extensive dialysis was not able to remove the bound Cu(II) from the peptide. Further, it was recently found that the affinities of $A\beta_{1-40}$ and $A\beta_{1-42}$ for Zn(II) are identical at two sites, $K_d$=100 nm and 13 $\mu$M (Bush, A. I., et al., *J. Biol. Chem.* 269:12152–12158 (1994); Atwood et al., unpublished observations), that the affinity of Aβ for Cu(II) at its high affinity binding site is greater than for Zn(II), and that the affinity of $A\beta_{1-42}$ for Cu(II) is much greater than the affinity of $A\beta_{1-40}$ for Cu(II) (Atwood, C. S., et al., *Journal of Biological Chemistry* 273:12817–12826 (1998)). The measured affinities are in agreement with the current findings since markedly more Cu(II) bound to $A\beta_{1-42}$ than to $A\beta_{1-40}$ preparations under the same incubation conditions, yet the affinity of Zn(II) for $A\beta_{1-40}$ and $A\beta_{1-42}$ was apparently not sufficiently high to prevent Zn(II) from being removed by the extensive dialysis (Table 1). Co-incubation with Zn(II) might have either facilitated the binding of Cu(II) (cooperativity), or permanently conditioned a structural configuration of the peptide promoting dismutase activity that remained stabilized after the Zn(II) had dissociated. The conformational factors that allow Zn(II) to promote Cu(II) binding and the activity of $A\beta_{1-42}$ more than $A\beta_{1-40}$ are not yet clear. It has been previously reported that Zn(II) binding to Aβ appears to promote the α-helical structure in the peptide (Huang, X., et al., *J. Biol Chem.* 272:26464–26470(1997)), which suggests that this structural feature may mediate Cu(II) binding and activity.

Having now fully described this invention, it will be understood by those of ordinary skill in the art that it can be performed within a wide range of equivalent modes of operation and/or using other parameters without affecting the scope of the invention or any embodiment thereof.

All patents and publications cited in the present specification are incorporated by reference herein in their entirety.

---

---

What is claimed is:

1. A method for identifying an agent that inhibits oxygen-dependent hydrogen peroxide formation activity, but does not inhibit the superoxide-dependent hydrogen peroxide formation, the method comprising:

(a) adding a candidate agent to an amyloid β (Aβ)-containing sample;

(b) determining whether said candidate agent inhibits dissolved oxygen-dependent hydrogen peroxide formation; and (c) determining whether said candidate agent does not inhibit the superoxide-dependent hydrogen peroxide formation.

2. The method of claim 1, wherein the method of determining whether said candidate agent does not inhibit the superoxide-dependent hydrogen peroxide formation is conducted using pulse radiolysis or the Nitro Blue Tetrazolium (NBT) assay.

3. The method of claim 1, wherein the method of determining whether said candidate agent does not inhibit the superoxide-dependent hydrogen peroxide formation is conducted by determining whether Aβ is capable of catalytically producing Cu(I), Fe(II) or $H_2O_2$.

4. A method for identifying an agent that alters the production of $H_2O_2$ by A$\beta$, said method comprising:

(a) adding Cu(II) or Fe(III) to a first A$\beta$ sample;

(b) allowing said first sample to incubate for an amount of time sufficient to generate $H_2O_2$;

(c) adding Cu(II) or Fe(III) to a second A$\beta$ sample, said second sample additionally comprising a candidate pharmacological agent;

(d) allowing said second sample to incubate for the same amount of time as said first sample;

(e) determining the amount of $H_2O_2$ produced by said first sample and second sample; and (f) comparing the amount of $H_2O_2$ present in said first sample to the amount of $H_2O_2$ present in said second sample;

whereby a difference in the amount of $H_2O_2$ present in said first sample as compared to said second sample indicates that said candidate pharmacological agent has altered the production of $H_2O_2$ by A$\beta$.

5. The method of claim 4, wherein the A$\beta$ samples of (a) and (b) are a biological fluid.

6. The method of claimed 5, wherein said biological fluid is cerebrospinal fluid (CSF).

7. The method of claimed 4, wherein the determination of the amount of $H_2O_2$ present in said first and second samples is determined by (a) adding catalase to a first aliquot of said first sample in an amount sufficient to break down all of the $H_2O_2$ generated by said sample;

(b) adding tris(2-carboxyethyl)-phosphine hydrochloride (TCEP), in an amount sufficient to capture all of the $H_2O_2$ generated by said samples, to (i) a first aliquot of said first sample;

(ii) a second aliquot of said first sample; and (iii) said second sample;

(c) incubating the samples obtained in (b) for an amount of time sufficient to allow the TCEP to capture all of the $H_2O_2$;

(d) adding 5,5'-dithio-bis(2-nitrobenzoic acid) (DTNB) to said samples obtained in (c);

(e) incubating said samples obtained in (d) for an amount of time sufficient to generate 2-nitro-5-thiobenzoic acid (TMB);

(f) measuring the absorbencies at 412 nm of said samples obtained in (e); and (g) calculating the concentration of $H_2O_2$ in said first and second samples using the absorbencies obtained in (f).

8. The method of claim 4, wherein said method is performed in a microtiter plate, and the absorbency measurements are performed by a plate reader.

9. The method of claim 4, wherein two or more different test candidate agents are simultaneously evaluated for an ability to alter the production of $H_2O_2$ by A$\beta$.

* * * * *